(12) United States Patent
Odom

(10) Patent No.: US 7,254,512 B2
(45) Date of Patent: Aug. 7, 2007

(54) PROGRAMMABLE HARDWARE ELEMENT WITH CARTRIDGE CONTROLLERS FOR CONTROLLING MODULAR MEASUREMENT CARTRIDGES THAT CONVEY INTERFACE INFORMATION

(75) Inventor: Brian Keith Odom, Georgetown, TX (US)

(73) Assignee: National Instruments Corporation, Austin, TX (US)

( * ) Notice: Subject to any disclaimer, the term of this patent is extended or adjusted under 35 U.S.C. 154(b) by 0 days.

(21) Appl. No.: 11/402,470

(22) Filed: Apr. 12, 2006

(65) Prior Publication Data

US 2006/0190209 A1    Aug. 24, 2006

Related U.S. Application Data

(63) Continuation of application No. 10/195,051, filed on Jul. 12, 2002.

(60) Provisional application No. 60/312,254, filed on Aug. 14, 2001.

(51) Int. Cl.
*G06F 3/00* (2006.01)

(52) U.S. Cl. .................. 702/127; 702/188; 710/100; 717/124; 717/149

(58) Field of Classification Search ........ 702/127–128, 702/57, 188; 717/124, 106, 149, 151; 703/2, 703/22; 716/4, 11, 18
See application file for complete search history.

(56) References Cited

U.S. PATENT DOCUMENTS

| 5,603,043 | A | * | 2/1997 | Taylor et al. ............... 712/1 |
| 6,073,160 | A | | 6/2000 | Grantham et al. |
| 6,081,533 | A | | 6/2000 | Laubach et al. |
| 6,219,153 | B1 | | 4/2001 | Kawanabe et al. |
| 6,219,628 | B1 | * | 4/2001 | Kodosky et al. ............... 703/2 |
| 6,584,601 | B1 | * | 6/2003 | Kodosky et al. ............... 716/4 |

(Continued)

OTHER PUBLICATIONS

U.S. Appl. No. 11/403,167, entitled "Adapting a plurality of measurement cartridges using cartridge controllers", by Brian Keith Odom, Jeffrey J. Kellam, Rafael Castro, and Kyle Bryson, filed on Apr. 12, 2006.

(Continued)

*Primary Examiner*—Michael P. Nghiem
*Assistant Examiner*—Hien Vo
(74) *Attorney, Agent, or Firm*—Meyertons Hood Kivlin Kowert & Goetzel, P.C.; Jeffrey C. Hood

(57) ABSTRACT

System and method for measurement, DAQ, and control operations which uses small form-factor measurement modules or cartridges with a re-configurable carrier unit, sensors, and a computer system to provide modular, efficient, cost-effective measurement solutions. The measurement module includes measurement circuitry, e.g., signal conditioner and/or signal conversion circuitry, and interface circuitry for communicating with the carrier unit. The module communicates interface information to the carrier unit, which informs the computer system how to program or configure a functional unit on the carrier unit to implement the communicated interface, or sends the information directly to the computer system. The computer system programs the carrier unit with the interface, and the programmed carrier unit and measurement module together function as a DAQ, measurement, and/or control device. The carrier unit may receive multiple cartridges, each having a respective interface protocol, where the carrier unit is configurable to support the respective protocols sequentially and/or in parallel.

25 Claims, 48 Drawing Sheets

U.S. PATENT DOCUMENTS

| | | |
|---|---|---|
| 6,823,283 B2 | 11/2004 | Steger et al. |
| 7,165,005 B2 | 1/2007 | Steger et al. |
| 2003/0074489 A1 | 4/2003 | Steger et al. |
| 2005/0137653 A1 | 6/2005 | Friedman et al. |
| 2006/0010199 A1 | 1/2006 | Brailean et al. |
| 2006/0184335 A1 | 8/2006 | Odom |

OTHER PUBLICATIONS

U.S. Appl. No. 11/684,749, entitled "Generating a data stream from cartridge controllers using a plurality of measurement cartridges", by Brian Keith Odom, Jeffrey J. Kellam, Rafael Castro, and Kyle Bryson, filed on Mar. 12, 2007.

* cited by examiner

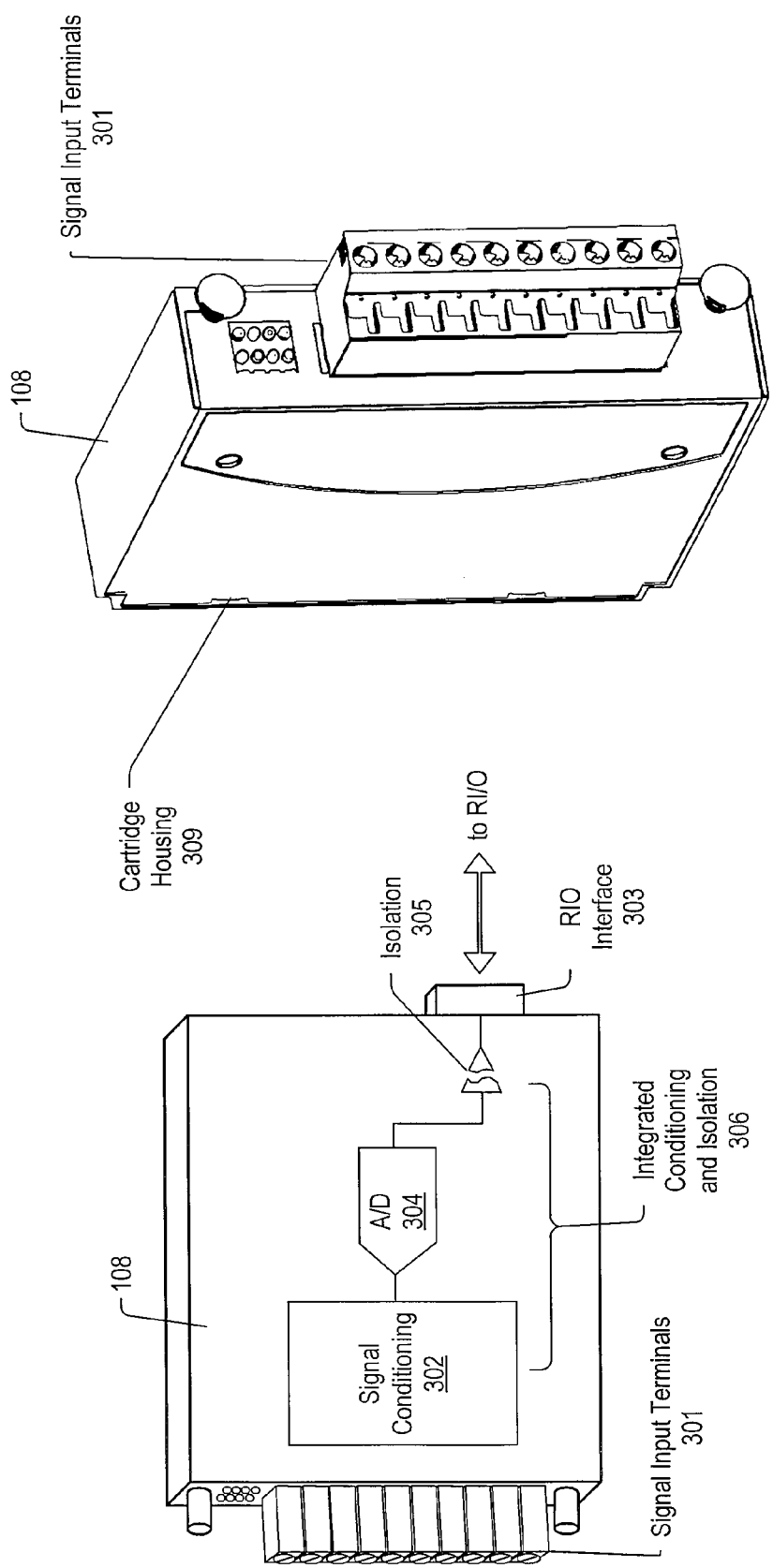

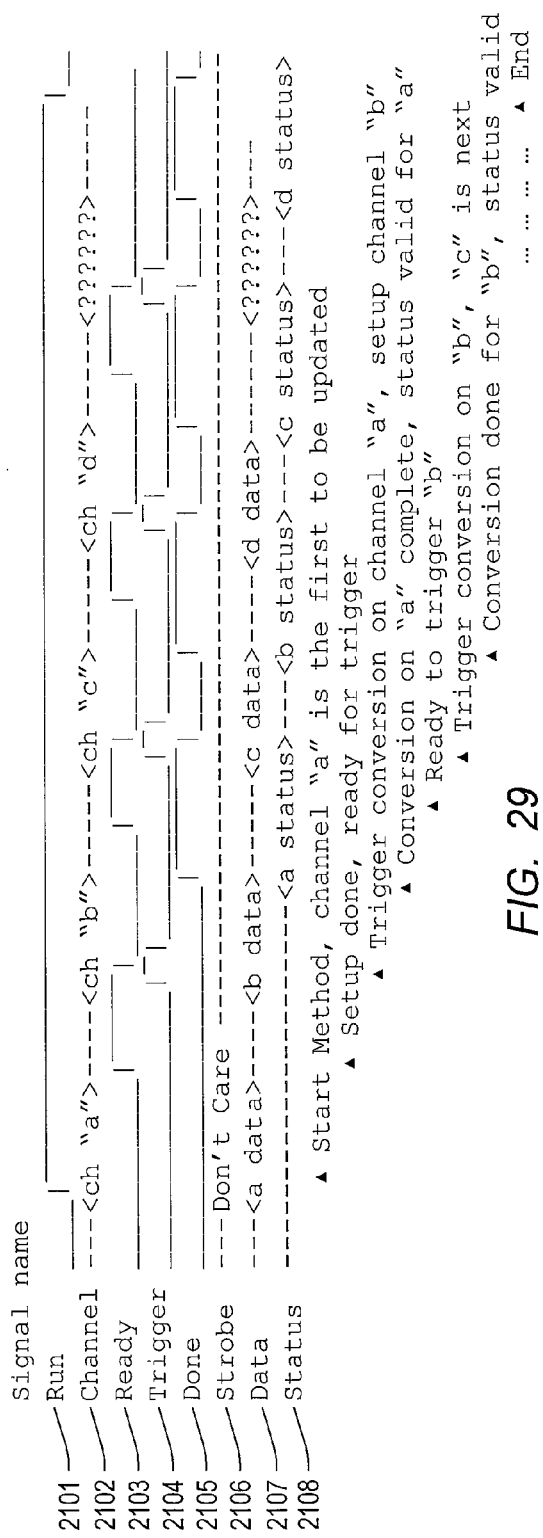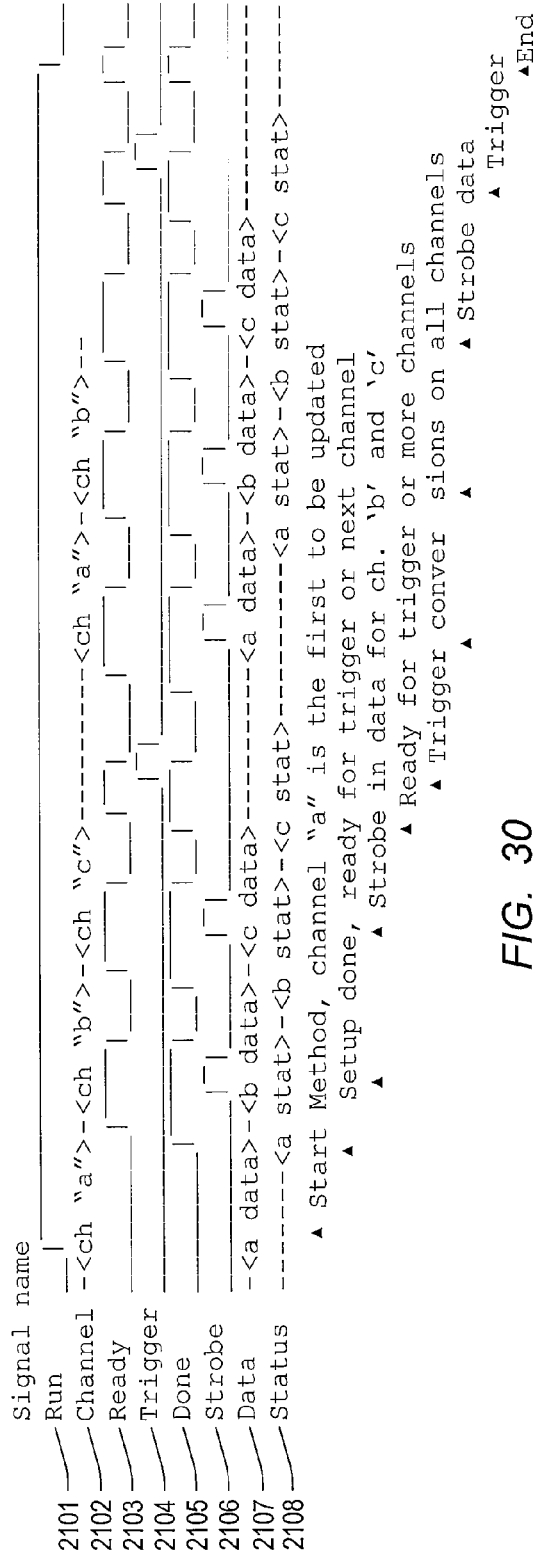
FIG. 29
FIG. 30

| | Signal | SPI Mode | ID Mode | DIO Mode |
|---|---|---|---|---|
| 14 | GND | Signal/Power ground | | |
| 4 | Power | +5 Vdc ± 5%, ≤100 mA | | |
| 8 | Sleep | put module into sleep mode (if supported by the module) | | |
| 1 | ID Select | | ID line: indicates presence of module, put module into ID mode | |
| 11 | SPI_CLK | SPI serial clock | | |
| 6 | MOSI | SPI slave data in | | DIO7 |
| 12 | MISO | SPI slave data out | | DIO6 |
| 2 | SPI_CS | Cartridge select/frame synch. | Unused | DIO5 |
| 7 | SPI_FUNC | SPI Function | EEPROM/1451.4 select | DIO4 |
| 9 | Convert | Convert/latch/load | Unused | DIO3 |
| 15 | Busy | Conversion/Load in progress | | DIO2 |
| 5 | Trig_Out | Generic trigger signal provided by the cartridge | | DIO1 |
| 10 | Oversample Clock | Over-sampling clock | | DIO0 |
| 3 | | Reserved | | |
| 13 | | | | |

FIG. 31

|         | Channel 0 |       |         |          | Channel 1 |      |       |
|---------|-----------|-------|---------|----------|-----------|------|-------|
| SPI in  | Setup     |       | Command |          | Setup     | Cmd. |       |
| SPI out |           |       |         | Response |           |      | Resp. |
| Convert |           |       |         |          |           |      |       |
| Busy    | ...       |       |         |          | ...       |      |       |

*FIG. 34A*

|         |       | Channel 0 |       | Channel 1 |       | Channel 2 |       |
|---------|-------|-----------|-------|-----------|-------|-----------|-------|
| SPI in  | Setup | Cmd.      |       | Cmd.      |       | Cmd.      |       |
| SPI out |       |           | Resp. |           | Resp. |           | Resp. |
| Convert |       |           |       |           |       |           |       |
| Busy    | ...   |           |       |           |       |           |       |

*FIG. 34B*

|         |       | Channel 0 |       |       |       | Channel 2 |       |       |       |
|---------|-------|-----------|-------|-------|-------|-----------|-------|-------|-------|
| SPI in  | Setup | Cmd.      |       | Cmd.  |       | Cmd.      |       | Cmd.  |       |
| SPI out |       |           | Resp. |       | Resp. |           | Resp. |       | Resp. |
| Convert |       |           |       |       |       |           |       |       |       |
| Busy    | ...   |           |       |       |       |           |       |       |       |

*FIG. 34C*

|         | Channel 0 |     | Channel 1 |     | Channel 2 |     | Channel 3 |     |
|---------|-----------|-----|-----------|-----|-----------|-----|-----------|-----|
| SPI in  | Data      |     | Data      |     | Data      |     | Data      |     |
| SPI out |           |     |           |     |           |     |           |     |
| Convert |           |     |           |     |           |     |           |     |
| Busy    | ...       |     | ...       |     | ...       |     | ...       |     |

*FIG. 34D*

| SPI in  | Setup ch0 |     | Setup ch1 |     | Setup ch2 |     | Setup ch3 |
|---------|-----------|-----|-----------|-----|-----------|-----|-----------|
| SPI out |           |     | Data ch0  |     | Data ch1  |     | Data ch2  |
| Convert |           |     |           |     |           |     |           |
| Busy    | ...       |     | ...       |     | ...       |     |           |

*FIG. 34E*

| Code | Command |
|---|---|
| 0000 0000 | End Sequence |
| 0000 0001 | |
| 0000 0010 | Wait for Cartridge Interface Busy line to be Low |
| 0000 0011 | Wait for Cartridge Interface Busy line to be high |
| 0000 0100 | De-assert ID_Select |
| 0000 0101 | Assert ID_Select |
| 0000 0110 | De-assert SPI_CS |
| 0000 0111 | Assert SPI_CS |
| 0000 1000 | Set Function code low |
| 0000 1001 | Set Function code high |
| 0000 1010 | Set Convert line low |
| 0000 1011 | Set Convert line high |
| 0000 1100 | |
| 0000 1101 | |
| 0000 1110 | Send/Receive SPI byte Least Significant Bit first |
| 0000 1111 | Send/Receive SPI byte Most Significant Bit first |
| 0001 00nn | Send Data/Status byte 'n' to SPI register |
| 0001 01nn | Send SPI register to Data/Status byte 'n' |
| 0001 1nnn | Send Scratchpad byte 'n' to SPI register |
| 0010 0nnn | Send SPI register to Scratchpad byte 'n' |
| 0010 1xxx | |
| 0011 nnnn | Send Config. register byte (channel*16)+n to SPI register |
| 010x xxxx | Set SPI Rate to 'x' (to be defined) |
| 0110 0001 | Drive Cartridge Interface 'Convert' with Std. mDAQ Interface 'Trigger' |
| 0110 0011 | Drive Convert line with inverse of Trigger line |
| 0110 0101 | Pulse Convert high on rising edge of Trigger line |
| 0110 0111 | Pulse Convert low on rising edge of Trigger line |
| 0110 0xx0 | Don't drive Convert line with Trigger line (drive with Sequencer) |
| 0110 1001 | Drive Std. mDAQ Interface Done line with Cartridge Interface Busy line |
| 0110 1011 | Drive Done line with inverse of Busy line |
| 0110 1101 | Assert Done for the rest of the phase on rising edge of Busy line |
| 0110 1111 | Assert Done for the rest of the phase on falling edge of Busy line |
| 0110 1xx0 | Don't drive Done line with Busy line (drive with Sequencer) |
| 0111 0001 | Drive Std. mDAQ Interface Ready line with Cartridge Interface Busy line |
| 0111 0011 | Drive Ready line with inverse of Busy line |
| 0111 0101 | Assert Ready for the rest of the phase on rising edge of Busy line |
| 0111 0111 | Assert Ready for the rest of the phase on falling edge of Busy line |
| 0111 0xx0 | Don't drive Ready line with Busy line (drive with Sequencer) |
| 0111 1xxx | (reserved) |
| 1xxx xxxx | (reserved) |

*FIG. 36*

| Code | τ (ns) | Code | τ (μs) |
|---|---|---|---|
| 0 | 45 | 16 | 0.73 |
| 1 | 55 | 17 | 0.86 |
| 2 | 65 | 18 | 1.0 |
| 3 | 80 | 19 | 1.2 |
| 4 | 95 | 20 | 1.4 |
| 5 | 110 | 21 | 1.7 |
| 6 | 130 | 22 | 2.0 |
| 7 | 150 | 23 | 2.4 |
| 8 | 180 | 24 | 2.8 |
| 9 | 220 | 25 | 3.4 |
| 10 | 260 | 26 | 4.0 |
| 11 | 310 | 27 | 4.8 |
| 12 | 370 | 28 | 5.6 |
| 13 | 440 | 29 | 6.7 |
| 14 | 520 | 30 | 8.0 |
| 15 | 610 | 31 | 9.5 |

FIG. 37

| Attribute | Bytes |
|---|---|
| Number of methods supported | 1 |
|   Method ID | 1 |
|     Number of Channels supporting this method | 1 |
|       Channel Number | 1 |
|       Setup phase sequence list index | 1 |
|       Strobe phase sequence list index | 1 |
|       Trigger phase sequence list index | 1 |
| Sequence Commands Revision | 1 |
| Number of sequence lists | 1 |
|   Sequence list length (=N) | 1 (?) |
|   Sequence list | N |
| Checksum (or CRC for easier HW implementation?) | 2 (?) |

FIG. 38

PROGRAMMABLE HARDWARE ELEMENT WITH CARTRIDGE CONTROLLERS FOR CONTROLLING MODULAR MEASUREMENT CARTRIDGES THAT CONVEY INTERFACE INFORMATION

PRIORITY CLAIM

This Application is a Continuation of U.S. application Ser. No. 10/195,051 titled "Measurement System with Modular Measurement Modules That Convey Interface Information" filed on Jul. 12, 2002, whose inventors are Perry Steger, Garritt W. Foote, David Potter, James J. Truchard, and Brian Keith Odom, which in turns claim benefit of priority to U.S. Provisional Application Ser. No. 60/312,254 titled "Measurement System with Modular Measurement Modules That Convey Interface Information" filed on Aug. 14, 2001, whose inventors are Perry Steger, Garritt W. Foote, David Potter and James J. Truchard.

FIELD OF THE INVENTION

The present invention relates to measurement, data acquisition, and control, and particularly to measurement devices with adaptive interfaces and modular signal conditioning and conversion devices which convey interface information.

DESCRIPTION OF THE RELATED ART

Scientists and engineers often use measurement or instrumentation systems to perform a variety of functions, including laboratory research, process monitoring and control, data logging, analytical chemistry, test and analysis of physical phenomena, and control of mechanical or electrical machinery, to name a few examples. An instrumentation system typically includes transducers and other detecting means for providing "field" electrical signals representing a process, physical phenomena, equipment being monitored or measured, etc. For example, detectors and/or sensors are used to sense the on/off state of power circuits, proximity switches, pushbutton switches, thermostats, relays or even the presence of positive or negative digital logic-level signals. The instrumentation system typically also includes interface hardware for receiving the measured field signals and providing them to a processing system, such as a personal computer. The processing system typically performs data analysis and presentation for appropriately analyzing and displaying the measured data.

Often, the field signals may be coupled to high common-mode voltages, ground loops, or voltage spikes that often occur in industrial or research environments which could damage the computer system. In that case, the instrumentation system typically includes isolation circuitry such as opto-couplers for eliminating ground-loop problems and isolating the computer from potentially damaging voltages. Input modules are typically provided for conditioning the raw field voltage signals by amplifying, isolating, filtering or otherwise converting the signals to the appropriate digital signals for the computer system. As one example, the digital signals are then provided to a plug-in data acquisition (DAQ) input/output (I/O) board, or a computer-based instrument which is plugged into one of the I/O slots of a computer system. Generally, the computer system has an I/O bus and connectors or slots for receiving I/O boards. Various computer systems and I/O buses may be used to implement a processing system.

Typical DAQ, measurement, and control modules include circuitry or components to provide a standard interface to external systems, such as PCI or PXI boards. The inclusion of these standard interface components on each module may be expensive, and may also substantially increase the size of a given module. Additionally, when multiple modules are used in a single system, such as a PXI based system fielding multiple sensors, the inclusion of PXI interface circuitry on each sensor is redundant and inefficient. Finally, if multiple communication interfaces are desired for the modules, the expense and size of the modules may increase dramatically with the inclusion of each additional interface card.

Therefore, improved measurement systems are desired which reduce cost and enhance efficiency and flexibility.

SUMMARY

Various embodiments of a system and method for measurement, DAQ, and control operations are described. The system may use small form-factor measurement modules in conjunction with a re-configurable carrier unit, sensors and a computer system to provide modular, efficient, cost-effective measurement solutions. In one embodiment, the measurement module is operable to communicate interface information to the carrier, which in turn informs the computer system how to program the carrier to implement the communicated interface, i.e., how to "talk" to the measurement module. In another embodiment, the carrier itself may include a processor and memory which receives the interface information from the module and programs reconfigurable hardware on the carrier to implement the interface.

This "adaptive interface" approach allows the measurement module to include only components necessary for providing the required functionality, i.e., the measurement module does not have to include hardware and software implementing standard interfaces for communication with external systems. Said another way, much of the interface responsibilities of the measurement module are assumed by the carrier, which itself is programmed by the computer system, thus the measurement module may be smaller and cheaper than typical functional modules. In the preferred embodiment, the measurement module has a small form factor. For example, in one embodiment, the measurement module may have dimensions less than or equal to approximately 1 inch by 2 inches by 3 inches. In one embodiment, the measurement module may have dimensions of approximately 0.2 inches by 1 inch by 1 inch or more. Thus, in a preferred embodiment, the measurement module has a compact form factor which may enable deployment in a variety of devices or carriers with minimal space requirements.

A typical measurement system using this approach includes a computer system coupled to a measurement or data acquisition (DAQ) device, which may include a carrier and one or more measurement modules. As used herein, the term "measurement device" is intended to include any of various types of devices that are operable to acquire and/or store data, and which may optionally be further operable to analyze or process the acquired or stored data. Examples of a measurement device include various types of instruments, such as oscilloscopes, multimeters a data acquisition device or card, a device external to a computer that operates similarly to a data acquisition card, a smart sensor, one or more DAQ or measurement modules in a chassis, and other similar types of devices. The computer system may couple to the measurement device through a serial bus, such as a USB (Universal Serial Bus), or any other medium including Ethernet, wireless media such as IEEE 802.11 (Wireless Ethernet) Bluetooth, a network, such as a Control Area Network (CAN) or the Internet, serial or parallel buses, or any other transmission means.

The host computer may comprise a CPU, a display screen, memory, and one or more input devices such as a mouse or keyboard, and may operate with the measurement device to analyze or measure data from the sensor/measurement device or to control the sensor and/or device. Alternatively, the computer may be used only to configure or program the measurement device, i.e., the carrier, as described below.

In one embodiment, the measurement module may include measurement circuitry which is operable to perform signal conditioning and/or signal conversion, e.g., a signal conditioner and/or a signal converter, such as an analog to digital converter (ADC) or a digital to analog converter. The measurement module may also include interface circuitry which is operable to provide an interface for the measurement circuitry, and which may also be operable to communicate an interface protocol to the carrier unit describing the interface, as mentioned above. The measurement module may also include additional transmission lines and/or buses for operation, e.g., a trigger line coupled to the ADC which may receive trigger signals from an external source, such as the computer system, and a power line for supplying power to the measurement module.

The measurement module may be further operable to couple to a sensor or actuator. The sensor may receive signals from a device or unit under test (UUT) and may send sensor signals to the measurement module for one or more of signal conditioning and signal conversion. For example, the sensor may measure a phenomenon, such as temperature, pressure, voltage, current, or any other phenomenon, and send signals to the measurement module. The signal conditioner comprised in the measurement module may then perform signal conditioning on the signals, where signal conditioning may include one or more of protection, isolation, filtering, amplification, and excitation, or other signal conditioning operations. The conditioned signals may then be processed by the signal converter, also comprised in the measurement module, which may be operable to perform one or more of analog to digital (A/D) conversion and digital to analog (D/A) conversion of the signal, depending on whether the signal is analog or digital. The conditioned, converted signals may then be transmitted by the interface circuitry to the carrier using the specified interface protocol. In other words, the measurement module may transmit the conditioned, converted signals to the carrier over the serial transmission medium SPI. The carrier may then further analyze the signals or transmit the signals to an external system, such as computer system.

In a preferred embodiment, the carrier includes a functional unit, e.g., a processor and memory or a programmable hardware element, which may be programmed by the computer system, or in other embodiments, by a processor and memory on the carrier. As used herein, the term "processor" is intended to include any of types of processors, CPUs, microcontrollers, or other devices capable of executing software instructions. As used herein, the term "programmable hardware element" is intended to include various types of programmable hardware, reconfigurable hardware, programmable logic, or field-programmable devices (FPDs), such as one or more FPGAs (Field Programmable Gate Arrays), or one or more PLDs (Programmable Logic Devices), such as one or more Simple PLDs (SPLDs) or one or more Complex PLDs (CPLDs), or other types of programmable hardware.

As mentioned above, the carrier unit is operable to receive interface protocol information from the measurement module specifying how to operate or interface with the measurement module. In one embodiment, the carrier unit may then communicate the interface protocol information to the computer system. Alternatively, the measurement module may communicate the interface protocol information directly to the computer system. Based on the interface protocol information, the computer system may program or configure the functional unit on the carrier unit to implement the interface as specified by the measurement module. In other words, the measurement module may tell the carrier how to "talk" with it, and the carrier may then tell the computer system how to program the carrier to communicate with the measurement module accordingly (or the measurement module may tell the computer system directly how to program the carrier). The computer system may then program the carrier (i.e., the carrier's functional unit), thereby implementing the interface specified in the interface protocol information communicated by the measurement module.

As noted above, in another embodiment, the carrier unit may be operable to receive the interface protocol information from the measurement module, and a processor and memory on the carrier unit may then program or configure the functional unit on the carrier unit to implement the interface as specified by the measurement module. In other words, the measurement module may communicate its interface protocol to the carrier, and the carrier may program itself (i.e., a processor/memory on the carrier may program a programmable hardware element) to communicate with the measurement module accordingly, thereby implementing the interface specified in the interface protocol information communicated by the measurement module.

This process may be referred to as initialization of the measurement module/carrier. The configured carrier and the measurement module may then be operable to perform measurement and data acquisition operations using the sensor and/or the computer system. In other words, the measurement module and the programmed carrier unit together may be operable to perform a measurement device (including a DAQ device), and/or a control device.

In one embodiment, the computer system may also store a program implementing one or more measurement functions, i.e., a measurement program. The measurement program may be a graphical program implementing the one or more measurement functions. The computer system may be operable to execute the measurement program to perform the one or more measurement functions, preferably in conjunction with operation of the carrier and/or measurement module, including analysis of data or signals received from the carrier, control of carrier and/or measurement module operations, and user interface functions, among others.

In another embodiment, the computer system may be operable to deploy the measurement program onto the functional unit of the carrier unit. In other words, in addition to, or instead of, programming the carrier unit to implement the interface, the computer system may download the measurement program onto the functional unit of the carrier, after which the carrier may be operable to execute the measurement program to perform the one or more measurement functions, preferably in conjunction with operation of the measurement module, and possibly the computer system. The configured carrier and the measurement module may then be operable to perform measurement and data acquisition operations using the sensor and/or the computer system.

In one embodiment, the carrier may also process and/or analyze the signals, and send the results of the processing or analysis to the computer system for storage and/or further analysis.

In various embodiments, the measurement module may also include a functional unit, e.g., a processor (or microprocessor) and memory, or a programmable hardware element (e.g., an FPGA), which may be operable to implement the module side of the specified interface and/or control module operations. Thus, the measurement module may include measurement circuitry, e.g., the signal conditioner and/or the signal converter (e.g., ADC or DAC), which may be operable to perform one or more of signal conditioning and signal conversion, as well as interface circuitry (including the functional unit) which is operable to provide an interface for the measurement circuitry. More specifically, the functional unit of the measurement module may retrieve the interface protocol information from memory and communicate the interface protocol information to the carrier.

In one embodiment, the measurement module may include signal input terminals for receiving analog inputs, e.g., from a sensor, and for optionally receiving a Transducer Electronic Data Sheet (TEDS) describing the functionality of the transducer (e.g., sensor) in machine-readable form. The measurement module may further include isolation circuitry which may be operable to protect the components of the measurement module from spurious signals, signal noise, harmful voltage and/or current surges, impedance mismatches, and the like.

The measurement module may also include terminals for communicating with external systems such as the computer system, including SPI, trigger line(s), power and ground lines, among others.

In one embodiment, the measurement module may be in the form of a measurement cartridge and the carrier in the form of a cartridge carrier which is operable to receive one or more of the measurement cartridges. For example, the carrier unit may comprise a chassis, a backplane comprised in the chassis providing for electrical communication, and one or more slots comprised in the chassis. Each of the one or more slots may include a connector that is coupled to the backplane, where each of the one or more slots may be adapted for receiving a measurement module. Thus, the carrier may host a plurality of measurement cartridges, each of which may provide measurement and/or control functionality for a measurement or control operation or task. The carrier may be operable to communicate with each measurement cartridge (i.e., module) and be programmed or configured (e.g., by the computer system or by a processor on the carrier) to implement the respective interface of each measurement cartridge. In this manner a suite of sensors may be fielded, each of which feeds signals to a respective measurement cartridge which in turn communicates through a respective interface (protocol) with the cartridge carrier. The cartridge carrier may in turn couple to a computer system. Thus, the carrier may support a heterogeneous plurality of interfaces without having to include a heterogeneous set of interface hardware components.

In a preferred embodiment, the measurement modules (or cartridges) may be easily removed, added, and replaced. In other words, measurement modules may be exchanged to change the configuration or capabilities of the measurement system. In one embodiment, the measurement module may be replaced without powering down the measurement system, i.e., the measurement module may be "hot-plugged" into the carrier, where the measurement module may communicate the interface protocol information to the carrier upon attachment, and the carrier is programmed in response, as described above. In another embodiment, the measurement module and/or carrier may require a reboot or reset after attachment to perform the described initialization. Thus, the interface circuitry (i.e., the measurement module) may be operable to communicate the interface protocol to the carrier unit upon one or more of attachment of the measurement module to the carrier unit, reset of the measurement module, reset of the carrier unit, reboot of the measurement module, and reboot of the carrier unit.

In one embodiment, the carrier may comprise a PXI card, i.e., may be implemented on a PXI card. The PXI card may be operable to plug into a PXI chassis or a suitably equipped computer system, and may implement the carrier functionality described above, i.e., the PXI card may include (in addition to PXI interface circuitry, memory, etc.) a functional unit which is programmable or configurable to implement an interface based on interface protocol information transmitted from a coupled measurement module, as described above. It should be noted that other card based implementations besides the PXI card implementation are also contemplated, for example, PCI, VXI, Infiniband, or other protocols or platforms may be used to implement a carrier, the PXI card embodiment being but one example.

In one embodiment, the carrier unit may comprise or be coupled to a Personal Digital Assistant (PDA). Thus the PDA may comprise the carrier unit and include one or more slots for measurement modules. Alternatively, the carrier unit may be in the form of an optionally detachable carrier module, which may in turn couple to a measurement module. The measurement module may in turn be operable to couple to a sensor or actuator, as described above. In one embodiment, the PDA may be operable to program the carrier (i.e., the carrier unit's functional unit) with the interface protocol information provided by the measurement module, as described in detail above, and may be further operable to provide functionality related to a measurement, and/or control task or operation. In another embodiment, the PDA may be used as an interface to another computer system. For example, a suitably equipped PDA may provide wireless communication for the carrier/measurement module.

In one embodiment, the measurement system may include a measurement module coupled to a "RIO" Reconfigurable I/O carrier, also referred to as a generalized carrier. As used herein, the term "RIO" carrier refers to a carrier which includes reconfigurable hardware which is configurable with respective interface protocols for one or more cartridges. In other words, a RIO carrier with multiple cartridge slots may be configured with multiple interfaces for inserted cartridges, such that each cartridge's interface is implemented by the RIO carrier. For example, if three cartridges with three different respective interfaces are inserted in three slots of the RIO carrier, then the RIO carrier may be configured to implement the three interfaces. Similarly, if multiple cartridges are sequentially inserted into and removed from a particular slot, the RIO carrier may be configured respectively for each cartridge, i.e., sequentially. The RIO carrier may further be operable to couple to any of various products or platforms.

In one embodiment, a channel or bus may be provided by the RIO carrier for each cartridge/interface protocol. In other words, each slot may have an associated dedicated bus for that slot, with a corresponding portion of the RIO carrier's reconfigurable hardware configurable to implement the interface for a cartridge inserted into the slot. In another embodiment, the RIO carrier may include a shared bus or backplane common to a plurality of the slots, where inserted cartridges may communicate through the common bus or backplane with the reconfigurable hardware of the RIO carrier in accordance with the respective interface protocols implemented on the reconfigurable hardware.

In yet another embodiment, the RIO carrier may be configurable to include not only the adaptive interface functionality described above, but may also include or may be configured to include, one or more measurement and/or control functions. For example, the carrier may perform all or a portion of timing, triggering, and synchronization functions for inserted cartridges or modules.

In one embodiment, the RIO carrier may include the carrier components/functionality described above, and may also include a register set, through which communication with the products/platforms may be effected. In various embodiments, the RIO carrier may provide additional functions which may include I/O scanning, timing and triggering, power-on states, logic, digital I/O timing/counting, data transfer and support for parallel and scanned backplanes, among others. Various products and platforms may provide means for the carrier to communicate with external systems. For example, an Application Programming Interface (API) may allow external systems to read and/or write to the registers in the register set to communicate and/or control the measurement system. For another example, a processor, e.g., a micro-controller, and a network interface card may couple the registers to a network through which communications with external systems may be facilitated.

In one embodiment, RIO based systems, i.e., a RIO carrier, may be extended with external I/O expansion, i.e., with additional I/O connections for coupling to a plurality of measurement modules. A RIO cartridge or card may provide connectors for analog I/O and/or digital I/O. The digital I/O may be coupled to an I/O expansion device, such as a breakout backplane, which may provide connectivity for a plurality of measurement module cards or cartridges, and may thereby be operable to facilitate external, synchronized, and conditioned I/O for the measurement system.

In another embodiment, the RIO card or device may couple to an addressable backplane, for example, through an SPI with slot select capabilities, and which may provide a plurality of individually addressable slots for a plurality of measurement modules or cartridges, which may each be individually targeted for communication by the carrier. Additionally, the addressable backplane may be expandable, i.e., additional addressable backplanes may be coupled to the addressable backplane to provide additional slots for additional measurement modules.

In yet another embodiment, the RIO card or device may couple to a "measurement module in the cable", where a measurement module may be comprised in a cable connector. In other words, the features of a measurement module, as described above, may be included in one or both connectors of a cable which may be coupled to the RIO device or to a sensor/actuator, as desired.

Thus, the use of measurement modules in combination with a variety of platforms, carrier units, and computer systems provides a broad range of approaches for efficient and affordable measurement systems, including established platforms such as PCI/PXI and FieldPoint, generalized carriers such as RIO, new USB/Ethernet devices, and small networked measurement nodes (e.g., smart sensors) for highly distributed measurement systems. These systems may provide for efficient, low-cost, modular, data acquisition, control, and integrated signal conditioning and conversion, as well as interfaces to sensors and actuators, including plug and play (PnP) sensors, and may do so using a small form factor.

BRIEF DESCRIPTION OF THE DRAWINGS

A better understanding of the present invention can be obtained when the following detailed description of the preferred embodiment is considered in conjunction with the following drawings, in which:

FIGS. 5A and 5B illustrate a measurement module, according to one embodiment;

FIGS. 21-30 are timing diagrams for defined methods supported by the measurement system, according to one embodiment;

FIG. 31 illustrates one embodiment of a measurement module pinout specification, according to one embodiment;

FIGS. 34A-34E illustrate representations of setup information for various measurement modules, according to one embodiment;

FIG. 36 illustrates a sequence list configuration, according to one embodiment;

FIG. 37 illustrates an SPI rate description format, according to one embodiment;

FIG. 38 illustrates a sequence command list file format, according to one embodiment.

Figure 1A:
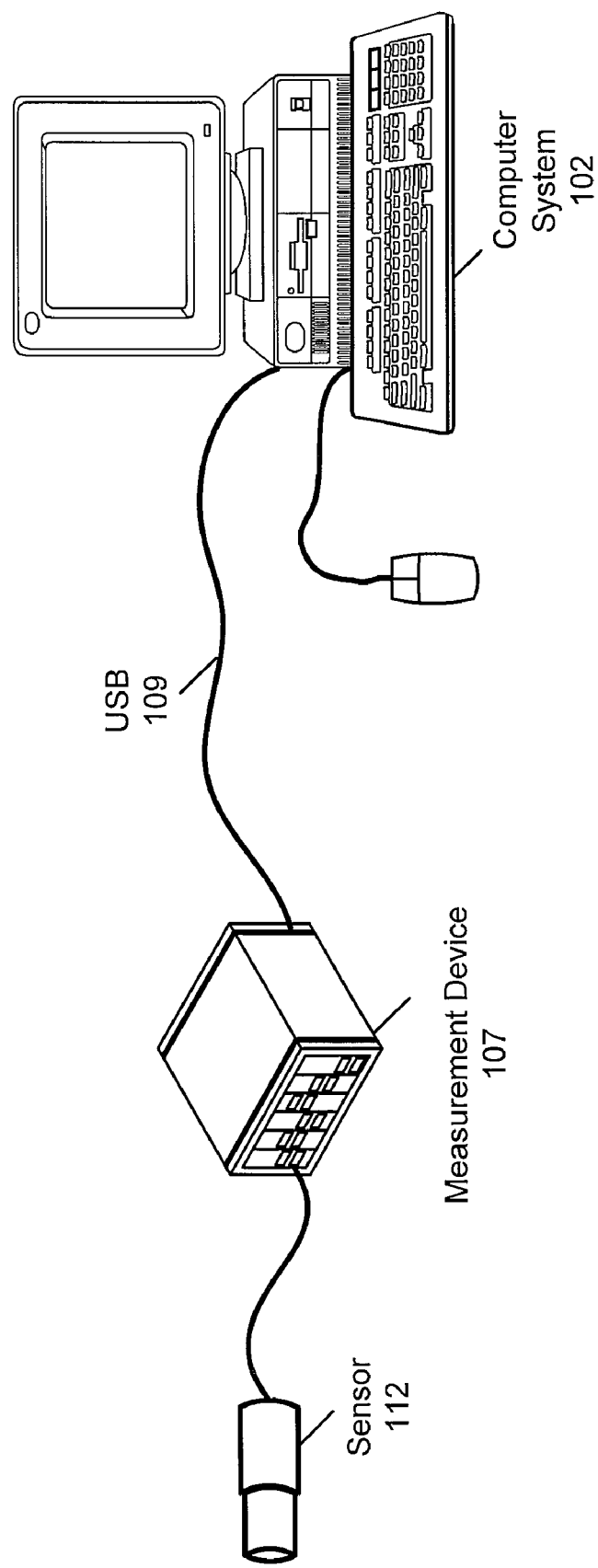
FIG. 1A illustrates a measurement system, according to one embodiment of the invention.

While the invention is susceptible to various modifications and alternative forms specific embodiments are shown by way of example in the drawings and may herein be described in detail. It should be understood however, that drawings and detailed description thereto are not intended to limit the invention to the particular form disclosed. But on the contrary the invention is to cover all modifications, equivalents and alternative following within the spirit and scope of the present invention as defined by the appended claims.

DETAILED DESCRIPTION OF THE EMBODIMENTS

Incorporation by Reference

The following U.S. Patents and patent applications are hereby incorporated by reference in their entirety as though fully and completely set forth herein.

U.S. Pat. No. 4,914,568 titled "Graphical System for Modeling a Process and Associated Method," issued on Apr. 3, 1990.

U.S. Pat. No. 6,219,628 titled "System and Method for Configuring an Instrument to Perform Measurement Functions Utilizing Conversion of Graphical Programs into Hardware Implementations".

U.S. Pat. No. 6,173,438 titled "Embedded Graphical Programming System" filed Aug. 18, 1997, whose inventors are Jeffrey L. Kodosky, Darshan Shah, Samson DeKey, and Steve Rogers.

U.S. Provisional Patent Application Ser. No. 06/312,254 titled "Measurement System with Modular Measurement Modules That Convey Interface Information" filed on Aug. 14, 2001, whose inventors are Perry Steger, Garritt W. Foote, David Potter and James J. Truchard.

U.S. patent application Ser. No. 10/194,927 titled "Measurement Module Interface Protocol Database and Registration System" filed on Jul. 12, 2002, whose inventors are Perry Steger, Garritt W. Foote, David Potter and James J. Truchard.

U.S. patent application Ser. No. 10/194,952 titled "Measurement System Including a Programmable Hardware Element and Measurement Modules that Convey Interface Information" filed on Jul. 12, 2002, whose inventors are Perry Steger, Garritt W. Foote, David Potter and James J. Truchard.

U.S. patent application Ser. No. 09/891,571 titled "System and Method for Configuring an Instrument to Perform Measurement Functions Utilizing Conversion of Graphical Programs into Hardware Implementations" filed on Jun. 25, 2001, whose inventors are Jeffrey L. Kodosky, Hugo Andrade, Brian Keith Odom, Cary Paul Butler, and Kevin L. Schultz.

U.S. patent application Ser. No. 09/745,023 titled "System and Method for Programmatically Generating a Graphical Program in Response to Program Information," filed Dec. 20, 2000, whose inventors are Ram Kudukoli, Robert Dye, Paul F. Austin, Lothar Wenzel and Jeffrey L. Kodosky.

U.S. patent application Ser. No. 09/595,003 titled "System and Method for Automatically Generating a Graphical Program to Implement a Prototype", filed Jun. 13, 2000, whose inventors are Nicolas Vazquez, Jeffrey L. Kodosky, Ram Kudukoli, Kevin L. Schultz, Dinesh Nair, and Christopher Caltagirone.

Figure 1B:
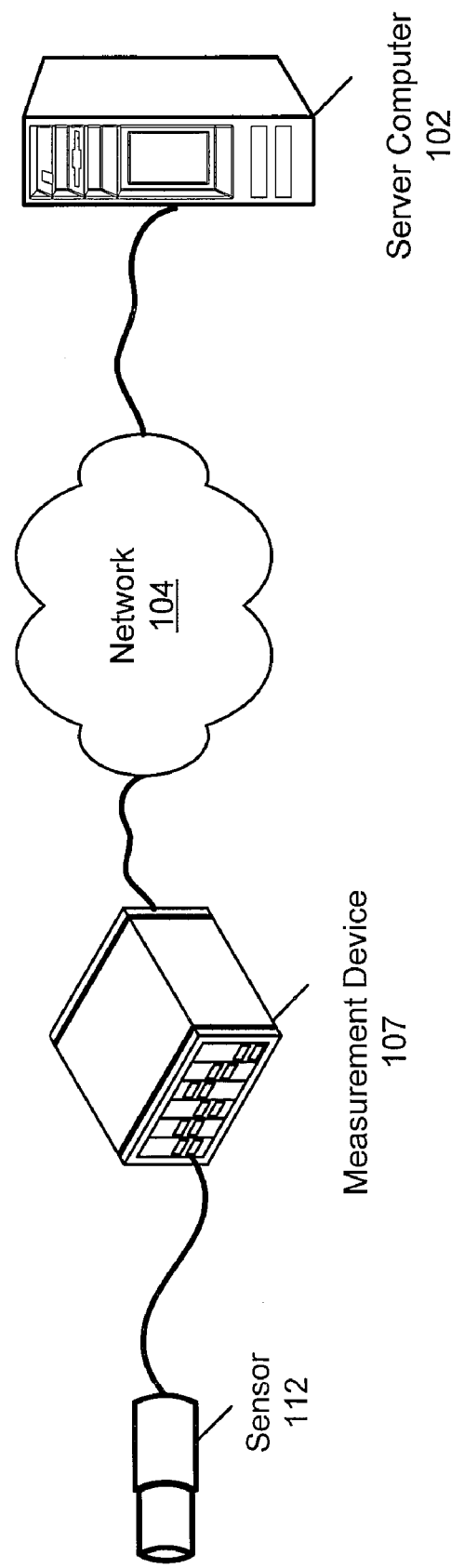
FIG. 1B illustrates a networked measurement system including a server computer system, according to one embodiment of the invention.

FIGS. 1A and 1B—A Measurement System

FIGS. 1A and 1B illustrate embodiments of a computer system 102 coupled to a measurement or data acquisition (DAQ) device 107. As used herein, the term "measurement device" is intended to include instruments, smart sensors, data acquisition devices or boards, and any of various types of devices that are operable to acquire and/or store data. A measurement device may also optionally be further operable to analyze or process the acquired or stored data. Examples of a measurement device include an instrument, such as a computer-based instrument (instrument on a card) an external instrument a data acquisition card, a device external to a computer that operates similarly to a data acquisition card, a smart sensor, one or more DAQ or measurement modules in a chassis, an image acquisition device such as an image acquisition board or smart camera, a motion control device and other similar types of devices. Exemplary instruments include oscilloscopes, multi-meters, and GPIB, PCI, PXI, and VXI instruments, among others.

In the embodiment of FIG. 1A, the computer system 102 may couple to the measurement device through a transmission medium, e.g., a serial bus, such as a USB 109. It should be noted that although a USB 109 is shown in this example, any other transmission medium may be used, including Ethernet, wireless media such as IEEE 802.11 (Wireless Ethernet) or (Bluetooth, a network, such as a fieldbus, a Control Area Network (CAN) or the Internet, serial or parallel buses, or other transmission means. For example, in the embodiment of FIG. 1B, the measurement device 107 is coupled to a server computer system 102 over a network 104, such as the Internet. In one embodiment, the server computer 102 may comprise a measurement module interface protocol (MMIP) server 102A which is operable to store a plurality of MMIPs for use by the measurement device. The MMIP server may be accessed by the measurement device 107 to retrieve the MMIP, as described in more detail below. In another embodiment, the MMIP server may be separate from the computer system 102, and the measurement device 107 (or the computer system 102) may retrieve the MMIP from the server 102A.

Thus, FIGS. 1A and 1B illustrate an exemplary data acquisition or measurement system. As FIGS. 1A and 1B show, the measurement device 107 may in turn couple to or comprise a sensor or actuator 112, such as a pressure or temperature gauge, a thermocouple, an imaging device, (e.g. a camera), or any other type of sensor or actuator. As shown in FIG. 1C, the measurement device 107 may include a measurement module (or multiple measurement modules) comprised in a chassis for performing one or more measurement (including) or processing functions as described below.

The host computer 102 may comprise a CPU, a display screen, memory, and one or more input devices such as a mouse or keyboard as shown. The computer 102 may operate with the measurement device 107 to analyze or measure data from the sensor 112 and/or measurement device 107 or to control the sensor 112 and/or measurement device 107. Alternatively, the computer 102 may be used only to configure or program the measurement device 107, as described below.

Figure 2:
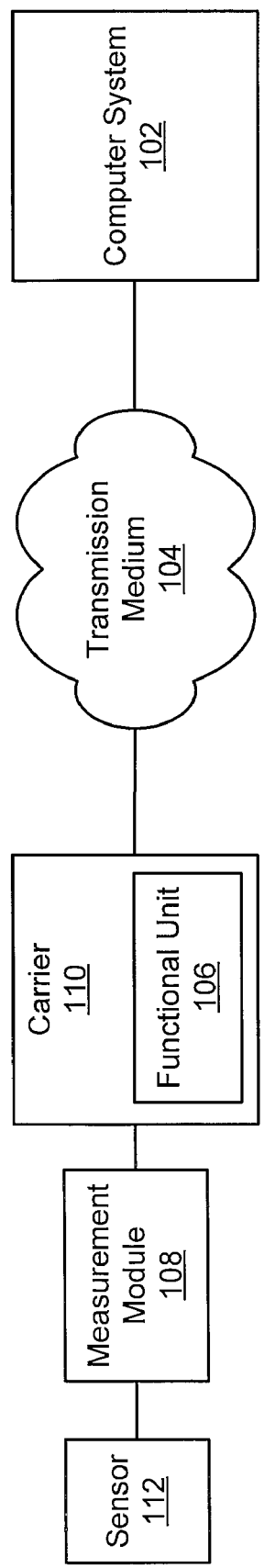
FIG. 2 is a block diagram of a networked measurement system computer system, according to one embodiment of the invention.

FIG. 2—Block Diagram of a Measurement System

FIG. 2 is a block diagram of a measurement system, according to another embodiment of the invention. As FIG. 2 shows, the measurement device 107 may comprise a carrier 110 and a measurement module 108. The sensor 112 may be coupled to the measurement module 108 which may in turn be coupled to the carrier unit 110, also referred to as carrier 110. The carrier 110 may be coupled to computer system 102 via a network (e.g., the Internet) 104 as shown, or, as mentioned above, may be coupled to the computer system 102 by other transmission means, including serial or parallel bus, wireless, and CAN, among others. In an embodiment where the carrier 110 includes a processor and memory, the carrier may operate independent of the computer 102, as describe in more detail below.

The measurement module 108 and the carrier 110 together may provide the functionality of the measurement device 107 of FIG. 1A. For example, in one embodiment, the measurement module 108 may be operable to perform signal conditioning and/or signal conversion on the signals sent by the sensor 112, and to transmit results of such processing on to the carrier 110. In one embodiment, the carrier 110 may be operable to receive data from the measurement module 108 and communicate the data (possibly in a different format or form) to the computer system 102, e.g., over the transmission medium 104. For example, the carrier 110 may receive signal data in a proprietary format from the measurement module 108 and format the data for transmission over wireless Ethernet to the computer system 102.

In the preferred embodiment, the carrier 110 includes a functional unit 106, which may be programmed, for example, by computer system 102 or by a processor/memory comprised in the carrier itself. As used herein, the term "functional unit" may include a processor and memory and/or a programmable hardware element. As used herein, the term "processor" is intended to include any of types of processors, CPUs, microcontrollers, or other devices capable of executing software instructions. As used herein, the term "programmable hardware element" is intended to include various types of programmable hardware, reconfigurable hardware, programmable logic, or field-programmable devices (FPDs), such as one or more FPGAs (Field Programmable Gate Arrays), or one or more PLDs (Programmable Logic Devices), such as one or more Simple PLDs (SPLDs) or one or more Complex PLDs (CPLDs), or other types of programmable hardware. Thus, the carrier unit 110 may be re-configurable, i.e., programmable by an external computer system, such as computer system 102.

More specifically, in the preferred embodiment, the carrier unit 110 may be operable to receive interface protocol information from the measurement module 108 specifying how to operate or interface with the measurement module 108. In one embodiment, the carrier unit 110 may then communicate the interface protocol information to the computer system 102. Alternatively, measurement module may communicate the interface information directly to the computer system. Based on the interface protocol information, the computer system 102 may program or configure the functional unit 106 on the carrier unit 110 to implement the interface as specified by the measurement module 108. In other words, the measurement module 108 may tell the carrier 110 how to "talk" with it, and the carrier 110 may then tell the computer system 102 how to program the carrier 110 to communicate with the measurement module 108 accordingly (or the measurement module may tell the computer system directly how to program the camera. The computer system 102 may then program the carrier 110 (i.e., the carrier's functional unit 106), thereby implementing the interface specified in the interface protocol information communicated by the measurement module 108.

In another embodiment, the carrier unit 110 may be operable to receive the interface protocol information from the measurement module 108, and a processor and memory on the carrier unit 110 may then program or configure the functional unit on the carrier unit 110 to implement the interface as specified by the measurement module. In other words, the measurement module may communicate its interface protocol to the carrier, and the carrier may program itself (i.e., the processor/memory on the carrier 110 may program a programmable hardware element on the carrier 110) to communicate with the measurement module accordingly, thereby implementing the interface specified in the interface protocol information communicated by the measurement module.

This process may be referred to as initialization of the measurement module/carrier. Further details of this process are described below.

Referring again to FIG. 2, the computer 102 may include a memory medium on which computer programs according to the present invention may be stored. As used herein, the term "memory medium" includes a non-volatile medium, e.g., a magnetic media or hard disk, or optical storage; a volatile medium, such as computer system memory, e.g., random access memory (RAM) such as DRAM, SRAM, EDO RAM, RAMBUS RAM, DR DRAM, etc.; or an installation medium, such as a CD-ROM or floppy disks, on which the computer programs according to the present invention may be stored for loading into the computer system. The term "memory medium" may also include other types of memory or combinations thereof.

The memory medium may be comprised in the computer 102 where the programs are executed or may be located on a second computer which is coupled to the computer 102 through a network, such as a local area network (LAN), a wide area network (WAN), or the Internet. In this instance, the second computer operates to provide the program instructions through the network to the computer 102 for execution. Also, the computer system 102 may take various forms, including a personal computer system, mainframe computer system, workstation, network appliance, Internet appliance, personal digital assistant (PDA), television set-top box, instrument, or other device. In general, the term "computer system" can be broadly defined to encompass any device having at least one processor which executes instructions from a memory medium.

Thus, in various embodiments, software programs of the present invention may be stored in a memory medium of the respective computer 102, or in a memory medium of another computer, and executed by the CPU. The CPU executing code and data from the memory medium thus comprises a means for receiving interface protocol information and programming or configuring the carrier 110 to implement the specified interface, as described in more detail below.

In one embodiment, the computer system 102 may also store a program implementing one or more measurement functions, i.e., a measurement program, e.g., a software program, such as a graphical program, implementing the one or more measurement functions. The term "measurement function" may include measurement, data acquisition, and/or control functions, such as displaying received data, analyzing and/or processing received data to generate a result, performing signal processing on received data, or otherwise analyzing and/or processing received data to perform a measurement. Examples of measurement functions include various instrumentation functions or control functions.

In the present application, the term "graphical program" or "block diagram" is intended to include a program comprising graphical code, e.g., two or more nodes or icons interconnected in one or more of a data flow, control flow, or execution flow format, where the interconnected nodes or icons may visually indicates the functionality of the program. Thus the terms "graphical program" or "block diagram" are each intended to include a program comprising a plurality of interconnected nodes or icons which visually indicates the functionality of the program. A graphical program may comprise a block diagram and may also include a user interface portion or front panel portion. The user interface portion may be contained in the block diagram or may be contained in one or more separate panels or windows. A graphical program may be created using any of various types of systems which are used to develop or create graphical code or graphical programs, including LabVIEW, DASYLab, and DiaDem from National Instruments, Visual Designer from Intelligent Instrumentation, Agilent VEE (Visual Engineering Environment), Snap-Master by HEM Data Corporation, SoftWIRE from Measurement Computing, ObjectBench by SES (Scientific and Engineering Software), Simulink from the MathWorks, WiT from Coreco, Vision Program Manager from PPT Vision, Hypersignal, VisiDAQ, VisSim, and Khoros, among others. In the preferred embodiment, the system uses the LabVIEW graphical programming system available from National Instruments.

The computer system 102 may be operable to execute the measurement program to perform the one or more measurement functions, preferably in conjunction with operation of the carrier 110 and/or measurement module 108. For example, the measurement program may be executable to perform one or more of measurement or control functions, including analysis of data or signals received from the carrier, control of carrier and/or measurement module operations, user interface functions, image processing or machine vision functions, and motion control functions, among others.

In another embodiment, the computer system may be operable to deploy the measurement program onto the functional unit 106 of the carrier unit 110. In other words, in addition to, or instead of, programming the carrier unit 110 to implement the interface, the computer system may download the measurement program onto the functional unit of the carrier. After deploying a software program on the functional unit 106 the carrier 110 may be operable to execute the measurement program to perform the one or more measurement functions, preferably in conjunction with operation of the measurement module 108, and possibly the computer system 102.

The configured carrier 110 and the measurement module 108 may then be operable to perform measurement operations using the sensor 112 and/or the computer system 102.

Figure 3A:
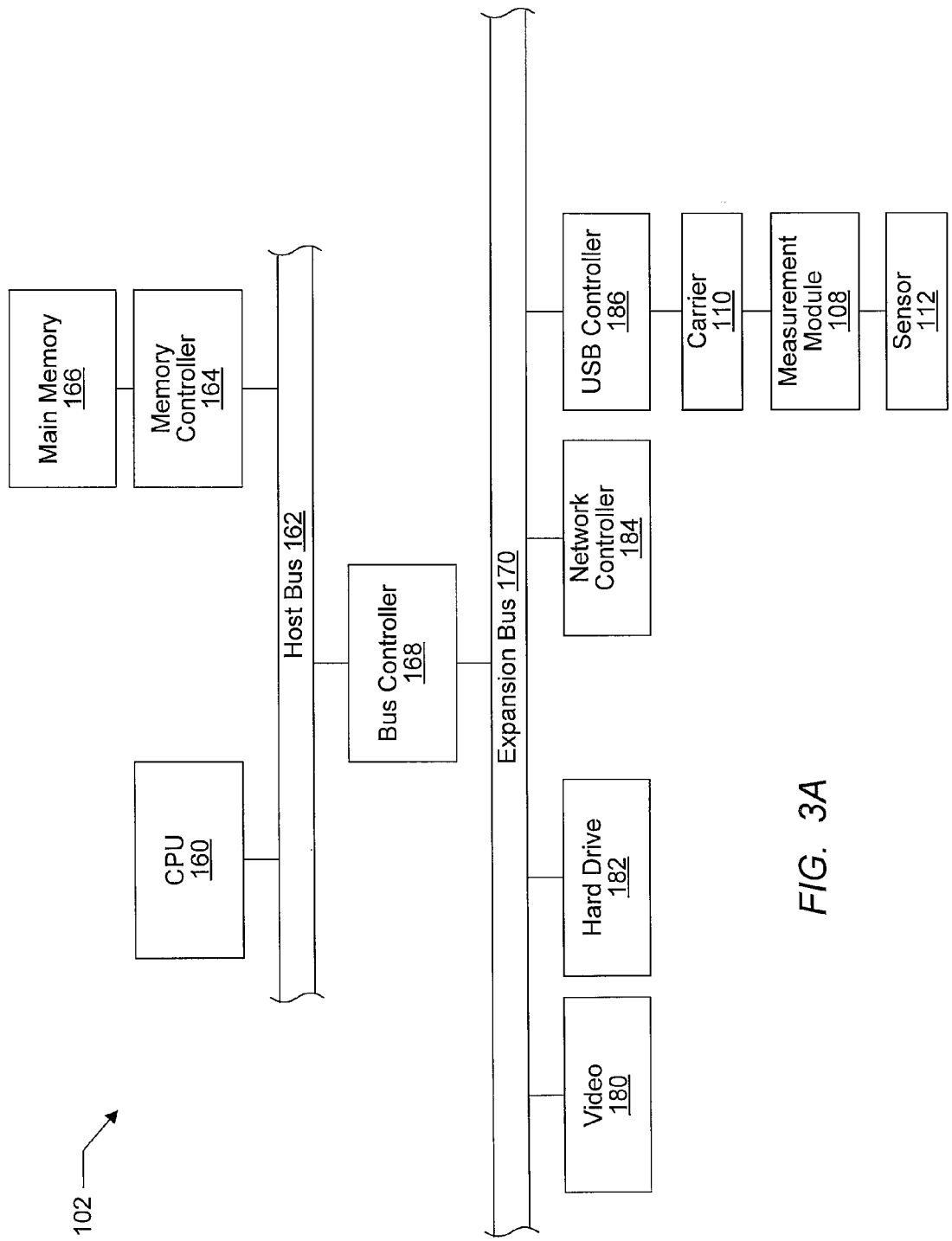
FIGS. 3A and 3B are block diagrams of two embodiments of a computer system.
Figure 3B:
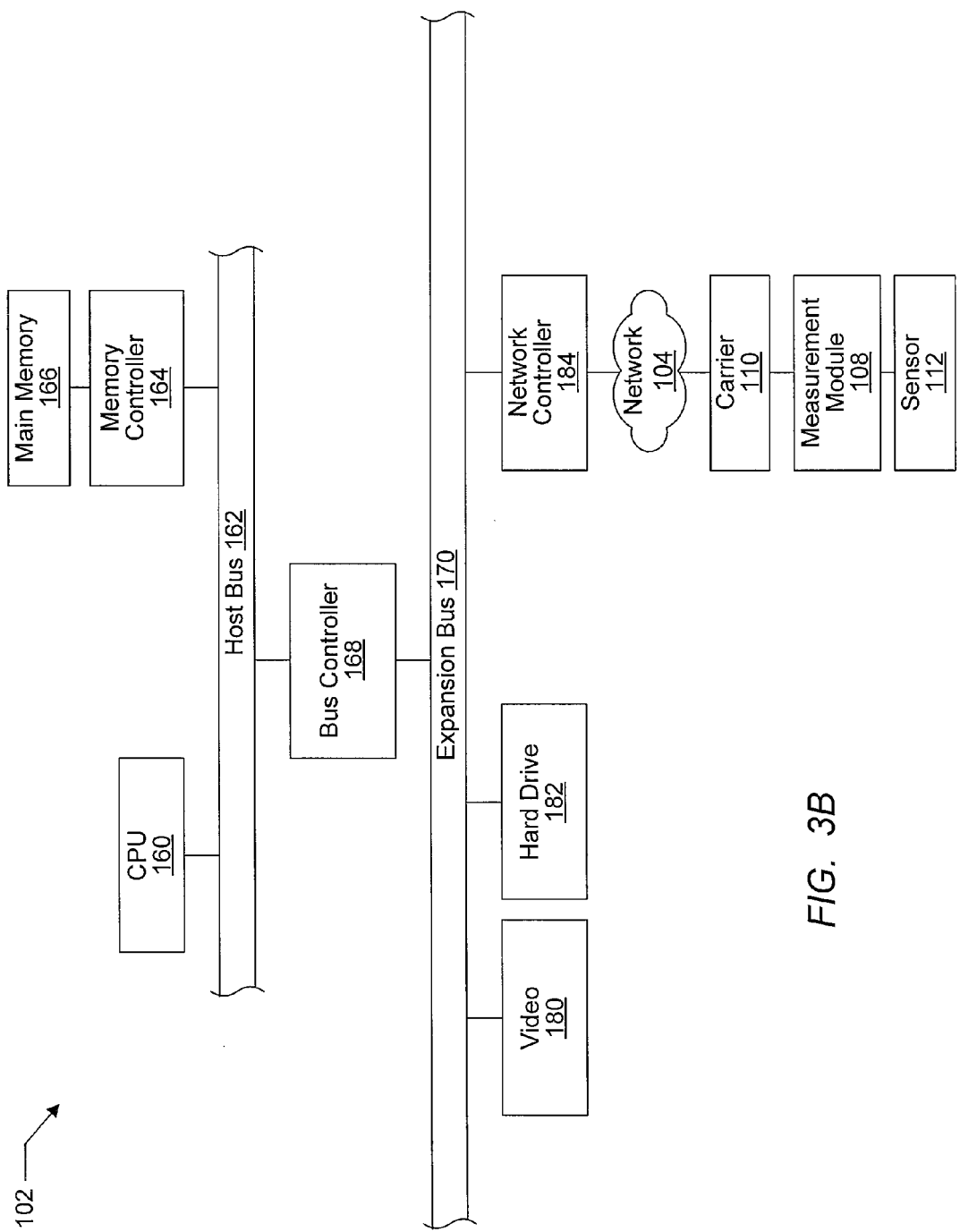

FIGS. 3A and 3B—Computer Block Diagrams

FIGS. 3A and 3B are exemplary block diagrams of the computer 102 of FIGS. 1A and 1B, respectively. The elements of a computer not necessary to understand the operation of the present invention have been omitted for simplicity. The computer 102 may include at least one central processing unit (CPU) or processor 160 which is coupled to a processor or host bus 162. The CPU 160 may be any of various types, including an x86 processor, a PowerPC processor, a CPU from the Motorola family of processors, a CPU from the SPARC family of RISC processors, as well as others. Main memory 166 may be coupled to the host bus 162 by means of memory controller 164. The main memory 166 is operable to store one or more programs according to the present invention. For example, the memory medium 164 may store a program which is executable to use interface protocol information received from the carrier 110 to program or configure the functional unit 106 comprised in the carrier 110. The main memory 166 may also store operating system software, i.e., software for operation of the computer system, as well as one or more application programs, as is well known to those skilled in the art. In addition, the main memory 166 may store one or more measurement programs which are executable to perform DAQ, measurement, and/or control tasks.

The host bus 162 is coupled to an expansion or input/output bus 170 by means of a bus controller 168 or bus bridge logic. The expansion bus 170 is preferably the PCI (Peripheral Component Interconnect) expansion bus, although other bus types may be used. The expansion bus 170 may include slots for various devices, the examples shown including a controller 186, e.g., a USB controller 186, shown in FIG. 3A coupled to the carrier 110 (as also shown in FIG. 1A), and a network controller 184 shown in FIG. 3B coupling to the carrier 110 over a network, as described above with reference to FIG. 1B. In both embodiments shown, the carrier 110 is coupled to a measurement module 108 (or multiple measurement modules), which may itself be coupled to a sensor 112 as shown.

The computer 102 may further comprise a video display subsystem 180 and hard drive 182 coupled to the expansion bus 170, also shown. It should be noted that the network controller 184 may be any type of network controller, including Ethernet, wireless Ethernet, Bluetooth, and CAN, among others. Furthermore, the USB controller shown is meant to be illustrative only, i.e., any other type of controller may be used as desired to communicate with the carrier 110. In other embodiments, the controller 186 may be comprised in the bus controller 168, or may be implemented in any other forms customary and known in the art. Of course, the embodiments shown in FIGS. 3A and 3B may be combined in various ways, such as, for example, coupling to a first carrier through a controller, and coupling to a second carrier via a network.

Figure 4A:
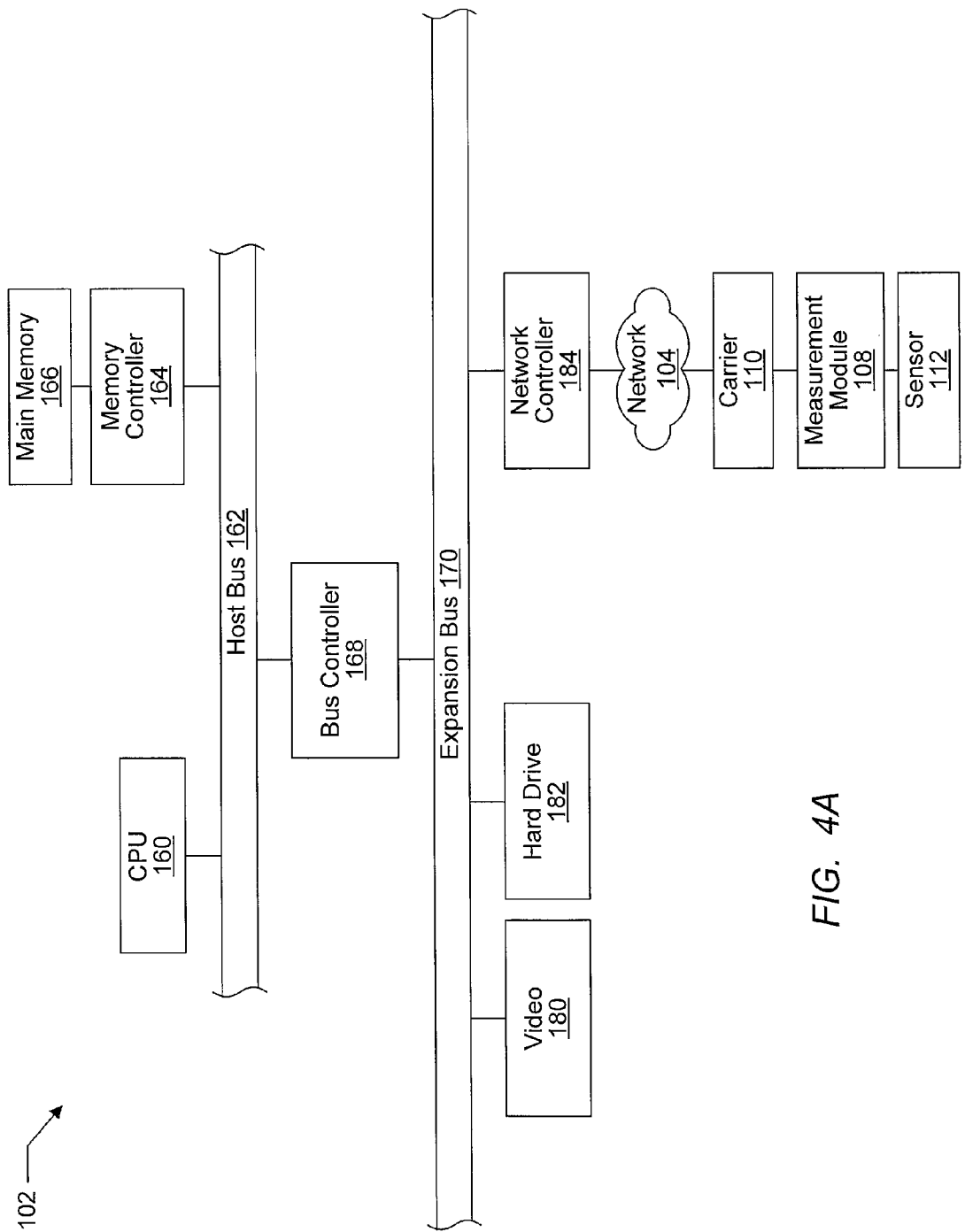
FIGS. 4A and 4B are block diagrams of embodiments of a measurement module.
Figure 4B:
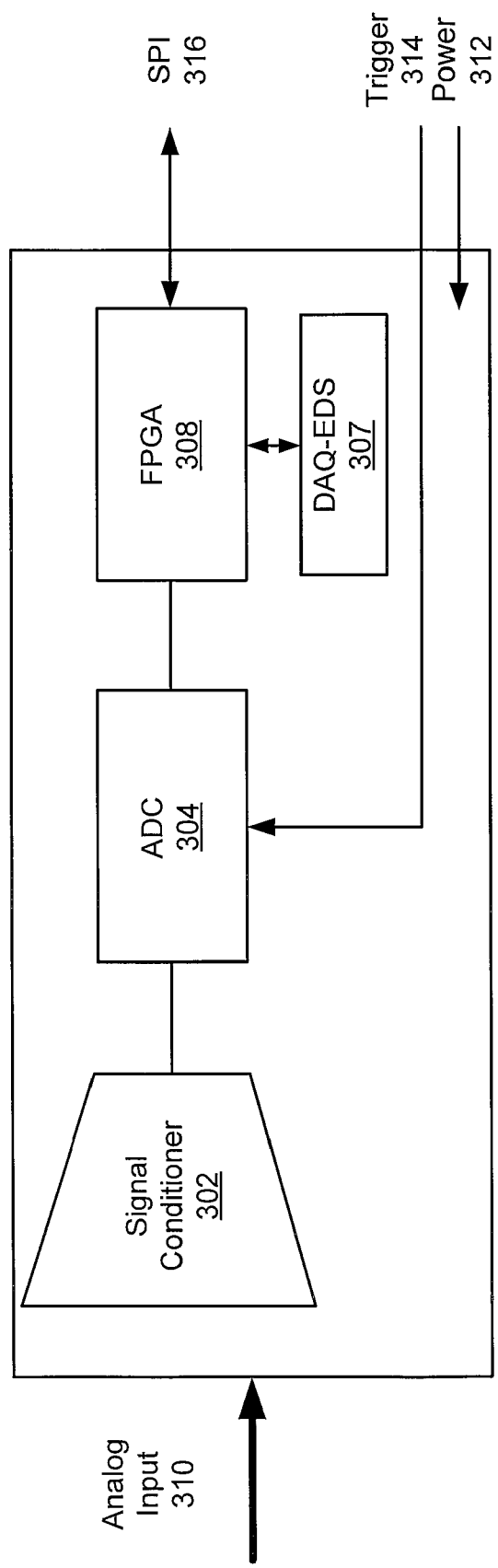

FIGS. 4A and 4B—Measurement Modules with a Functional Unit

FIGS. 4A and 4B are block diagrams of embodiments of a measurement module 108 where the measurement module 108 includes one or more functional units 106. As mentioned above, a functional unit refers to either a processor 306 and memory (or multiple processors and/or memories) or one or more programmable hardware elements 308, such as an FPGA, or various combinations thereof.

FIG. 4A—A Measurement Module with Processor

FIG. 4A is a block diagram of a measurement module 108A including a processor 306, e.g., a micro-controller. As FIG. 4A shows, the measurement module 108A may include measurement circuitry which is operable to perform one or more of signal conditioning and signal conversion. For example, in one embodiment, the measurement circuitry may include a signal conditioner 302 and/or a signal converter 304, such as an analog to digital converter (ADC) 304, as shown. In other embodiments, the signal converter 304 may comprise a digital to analog converter, or other types of signal converter, as desired.

The measurement module 108A may also include interface circuitry which is operable to provide an interface for the measurement circuitry. In one embodiment, the interface circuitry may be operable to couple to a carrier unit 110, and may also be operable to communicate an interface protocol to the carrier unit 110 describing the interface.

In the embodiment shown in FIG. 4A, the interface circuitry includes micro-controller 306 and memory 307, such as an EEPROM 307, containing a DAQ Electronic Data Sheet (EDS), defined by IEEE 1451.2, and an optional calibration history.

IEEE 1451.2 defines an interface between transducers and microprocessors useful in industrial automation and other fields. The standard defines a physical interface comprising a data transport serial link, in addition to triggering, interrupt and hot swap signaling. The standard also defines a transducer electronic data sheet, TEDS, that describes the functionality of the transducer in machine-readable form. The interface supports as many as 255 independent transducer channels. These may be accessed individually or as a unit. The standard may be used to implement a variety of measurement functions.

In one embodiment, the memory storing the DAQ-EDS 307 may also store program instructions for the processor 306. In another embodiment, the measurement module 108A may include additional memory, not shown, for storing the program instructions. The program instructions may be executable by the processor 306 to implement the measurement module side of the interface and/or to manage operations of the measurement module 108A. In another embodiment, the program instructions may be executable by the processor 306 to perform a measurement task or operation.

In one embodiment, as described above, the carrier unit 110 may include the functional unit 106, such as microcontroller or FPGA which is programmable to interface with the measurement module in accordance with the communicated interface protocol. In other words, the carrier unit 110 may comprise an adaptive interface which uses the functional unit 106 to implement an interface according to instructions or specifications from the measurement module 108. The measurement module 108 and the programmed carrier unit 110 together may then be operable to perform as one or more of a measurement device and a control device.

As described above, in one embodiment, the carrier unit 110 may be operable to couple to a computer system, i.e., computer system 102, which is operable to program the one or more functional units to interface with the measurement module in accordance with the communicated interface protocol. In other words, the computer system 102 may retrieve or receive the interface protocol information from the carrier, or from the measurement module 108A and program the carrier 110, i.e., the functional unit(s) 106 on the carrier unit 110, thereby implementing the interface protocol for communication with and operation of the measurement module 108A. As mentioned above, in one embodiment, the computer system 102 may be operable to couple to the carrier unit 110 over a network, such as the Internet, thus the carrier unit 110 may be programmed remotely by the computer system 102. As also mentioned above, in one embodiment, the computer system may comprise a Personal Digital Assistant (PDA), as described below, or any other type of computing device.

In another embodiment, the computer system 102 may be comprised in the carrier unit. For example, the computer may be a "computer-on-a-card" or "computer-on-a-chip", where substantially all of the functionality of a PC (personal computer) is provided by components on a computer card, board or chip contained in the carrier unit 110. In this embodiment, the module 108 may communicate the interface protocol to the carrier 110, and a processor/memory on the carrier 110 may program the functional unit on the carrier 110 with the interface protocol.

The measurement module 108, as described above, may be further operable to couple to a sensor 112. The sensor 112 may send sensor signals to the measurement module for one or more of signal conditioning and signal conversion. For example, the sensor 112 may measure a phenomenon, such as temperature, pressure, voltage, current, or any other phenomenon, and send signals to the measurement module, as indicated by the analog input 310 of FIG. 4A. The signal conditioner 302 may then perform signal conditioning on the signals, where signal conditioning may include one or more of protection, isolation, filtering, amplification, and excitation, or other signal conditioning operations.

The conditioned signals may then be processed by the signal converter 304, which may be operable to perform one or more of analog to digital (A/D) conversion and digital to analog (D/A) conversion. In this embodiment, the input is analog (310), therefore the signal converter 304 is an ADC 304, as shown.

The conditioned converted signals may then be transmitted by the interface circuitry to the carrier 110 using the specified interface protocol. In other words, the processor 306 may transmit the conditioned, converted signals to the carrier 110 over the serial transmission medium SPI 316. The carrier 110 may then transmit the signals to an external system, such as computer system 102.

In one embodiment, the carrier 110 may process and/or analyze the signals, and send the results of the processing or analysis to the computer system 102 for storage and/or further analysis. In another embodiment, the carrier 110 may send a control signal to a component of the measurement system or to an external system in response to the analysis.

As FIG. 4A also shows, the measurement module 108A may also include additional transmission lines and/or buses for operation, e.g., a trigger line 314 coupled to the ADC 304 which may receive trigger signals from an external source, such as computer system 102, and a power line 312 for supplying power to the measurement module.

FIG. 4B—A Measurement Module with Programmable Hardware

FIG. 4B is a block diagram of a measurement module 108B including a programmable hardware element 308, e.g., an FPGA 308. As may be seen, measurement module 108B is substantially the same as measurement module 108A described above with reference to FIG. 4A, but where the processor 306 is replaced with programmable hardware element 308, therefore description of the unchanged components is abbreviated or omitted.

As FIG. 4B shows, the measurement module 108B may include measurement circuitry, e.g., the signal conditioner 302 and/or the signal converter 304 (e.g., ADC or DAC), which may be operable to perform one or more of signal conditioning and signal conversion, as well as interface circuitry which is operable to provide an interface for the measurement circuitry. As described above, the interface circuitry may be operable to couple to a carrier unit 110, and to communicate an interface protocol to the carrier unit 110 describing the interface, whereupon the carrier unit's one or more functional units may be programmed (by computer system 102 or by a processor/memory on the carrier 110) using the interface protocol to implement the interface. After being programmed or configured with the interface, the measurement module and the programmed carrier unit together may then be operable to perform as one or more of a DAQ device, a measurement device, and a control device.

More specifically, in one embodiment, the programmable hardware element of the measurement module 108, e.g., the FPGA 308, may retrieve the interface protocol information from memory, as represented by the DAQ-EDS 307, and communicate the interface protocol information to the carrier 110. In one embodiment, the memory storing the DAQ-EDS 307 may also store configuration information, e.g., a hardware description, for the FPGA 308. In another embodiment, the measurement module 108B may include additional memory, such as non-volatile memory, not shown, for storing the configuration information. The configuration information may be usable to configure or program the FPGA 308 to implement the measurement module side of the interface and/or to manage operations of the measurement module 108B.

In one embodiment, a hardware netlist (preferably an FPGA-specific netlist) may be generated from the hardware description using various synthesis tools. The term "netlist" comprises various intermediate hardware-specific description formats comprising information regarding the particular hardware elements required to implement a hardware design and the relationship among those elements. The hardware netlist is used to create or configure the programmable hardware element to execute the specified function. As used herein, the term "hardware configuration file" refers to the program, bitfile, etc., which is loaded onto the programmable hardware element.

As also described above, the measurement module 108B may be operable to couple to sensor 112 which may send sensor signals to the measurement module for signal conditioning and/or signal conversion. The conditioned, converted signals may then be transmitted by the interface circuitry to the carrier 110 using the specified interface protocol. In other words, the FPGA 308 may operate to transmit the conditioned, converted signals to the carrier 110 over the serial transmission medium SPI 316. The carrier 110 may then transmit the signals (possibly in a different format) to an external system, such as computer system 102.

Thus, in one embodiment, the measurement module may communicate interface information to the carrier unit, where the interface information specifies an interface for operating with the measurement module; the carrier unit 110 may communicate the interface information to the computer system 110; (alternatively, the measurement module 108 may communicate interface information directly to the computer system 102) and the computer system 102 may program a functional unit on the carrier unit 110, thereby implementing the specified interface in the carrier unit. In another embodiment, the carrier unit 110 may include a processor and memory which receives the interface information from the measurement module, and programs the functional unit on the carrier unit 110 to implement the interface.

After the programming, the carrier unit 110 and the measurement module 108 may together be operable to perform one or more of a measurement and control task. In one embodiment, after the carrier unit 110 is programmed, the carrier unit 110 and the measurement module 108 together perform one or more of a data acquisition, measurement, and control task. In another embodiment, the computer system 102 may also perform one or more of a measurement and control task in conjunction with the carrier unit 110 and the measurement module 108.

Various embodiments of the invention may include additional features to provide efficient, low-cost measurement solutions. For example, DAQ-on-a-chip components and inexpensive, low-power digital components such as networking, processors, A/D converters, etc., allow measurement modules 108 to be developed which provide a variety of signal conditioning/conversion functions in a small form at a modest price. Additionally, various embodiments of the invention address the current trend toward networked/digital sensors and the emergence of plug and play (PnP) (analog) sensors, in that the carrier 110 is capable of adaptive "hot plug" functionality, i.e., the carrier 110 may adapt itself automatically to interface correctly with a smart sensor (i.e., a sensor/measurement module device). Thus, in various embodiments of the invention, the customer may be provided with modularity and flexibility, easy sensor connection (with integrated signal conditioning/conversion), and a variety of network options in that there is no dominant standard which requires compliance. Additionally, the customer may be provided an affordable and feasible path to smart sensors.

FIGS. 5A and 5B—Measurement Module

Figure 7A:
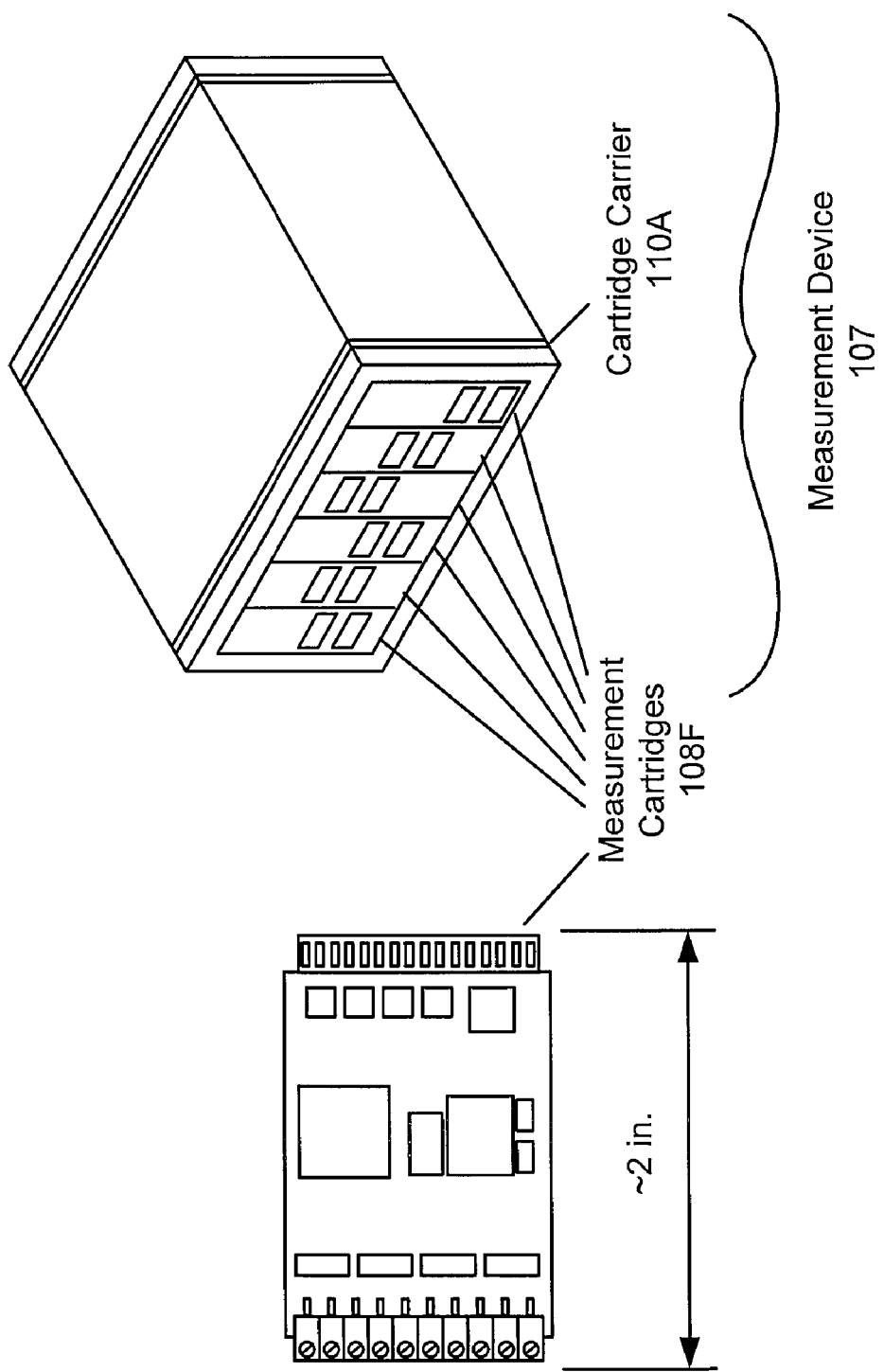
FIG. 7A illustrates a cartridge carrier with measurement cartridges, according to one embodiment of the invention.
Figure 7B:
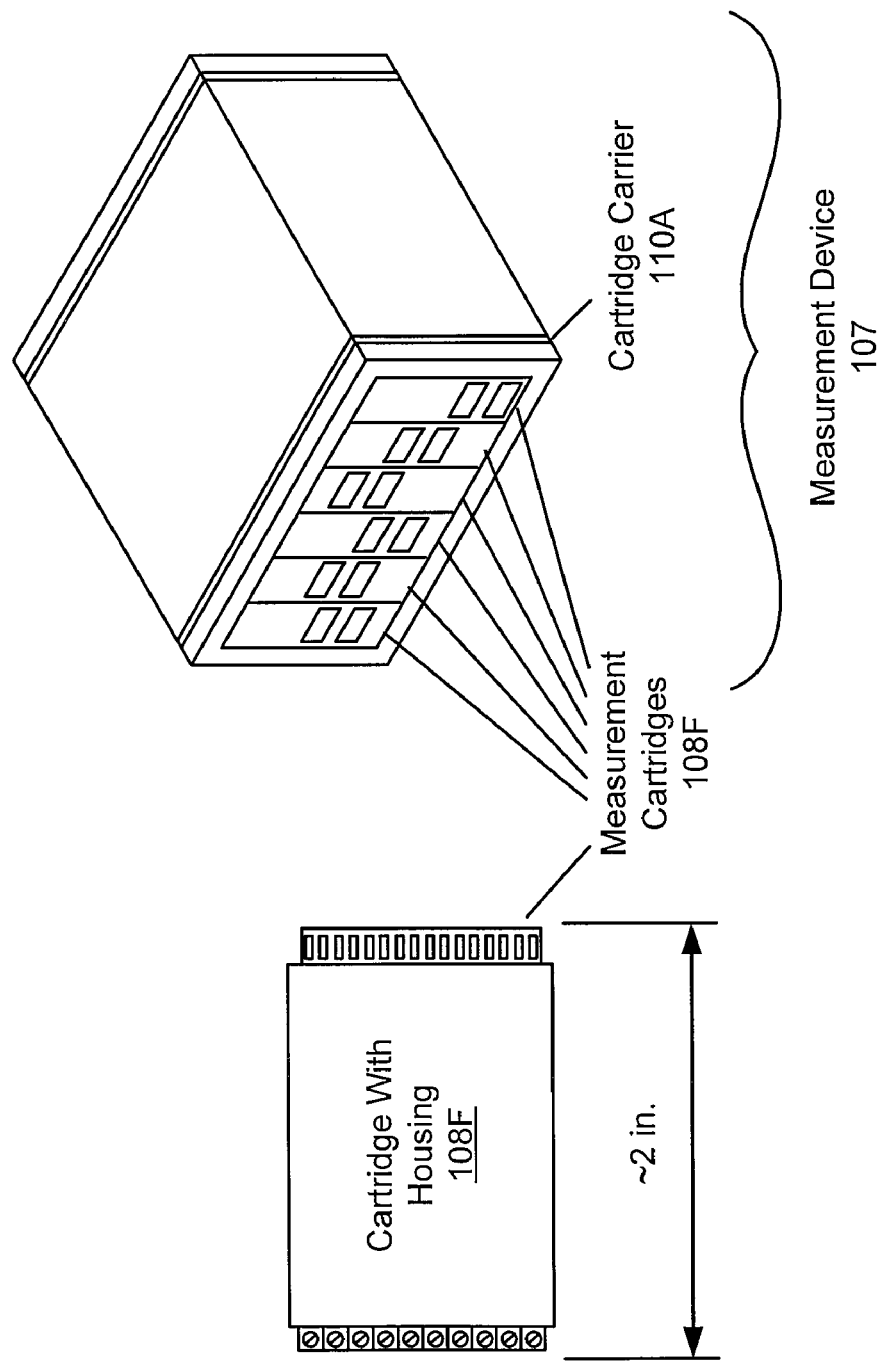
FIG. 7B illustrates a cartridge carrier with measurement cartridges, according to another embodiment of the invention.

FIGS. 5A and 5B illustrate a measurement module, according to one embodiment. More specifically, FIGS. 5A and 5B illustrate a measurement module 108 in the form of a measurement cartridge which may be inserted into a slot in a cartridge carrier, as shown in FIGS. 7A and 7B, described below.

As FIG. 5A shows, the cartridge 108 may include signal input terminals 301 which may provide direct connectivity to various sensors and devices. In one embodiment, the measurement cartridge 108 may include integrated conditioning and isolation logic 306, including logic for signal conditioning 302, signal conversion (e.g., A/D and/or D/A converters) 304, and/or isolation 305, as shown. In various embodiments, the logic may be implemented in hard-wired circuitry, programmable hardware, such as an FPGA, and/or a micro-controller/memory, as desired. Finally, in the embodiment shown, the cartridge 108 may include a RIO (Reconfigurable I/O) interface 303 for communicating with a RIO carrier, as described in more detail below. In this embodiment, all timing, triggering, synchronization, etc., may be relegated to the RIO carrier, thereby simplifying the functional requirements of the measurement cartridge 108. The cartridge interface may comprise a very simple interface, e.g., SPI or 8 parallel DIO, through which communication with a RIO carrier may be facilitated.

FIG. 5B illustrates the measurement cartridge of FIG. 5B, where the cartridge 108 is shown with a cartridge housing 309. The housing 309 may serve to protect the various cartridge components and to provide structural support to the cartridge 108. In a preferred embodiment, the measurement cartridge may have a compact form factor. For example, in one embodiment, the measurement cartridge may measurement approximately 3.4" H×2.5" D×0.8" W, although other compact form factors are also contemplated.

In one embodiment, the measurement cartridge 108 may be operable to provide single-point and waveform I/O, e.g., analog: under 1 MS/s per cartridge, and/or digital: paralleled pass-through (fast). In a typical embodiment, channel granularity for the cartridge 108 may include 4 channels/module (higher with mass termination) for analog I/O, and/or 8 parallel I/O lines pass-through (higher density with mass termination) for digital I/O. Additionally, in one embodiment, up to 500 mW of power per slot on the cartridge carrier 110 may be provided for the operation of the cartridge 108.

Figure 5C:
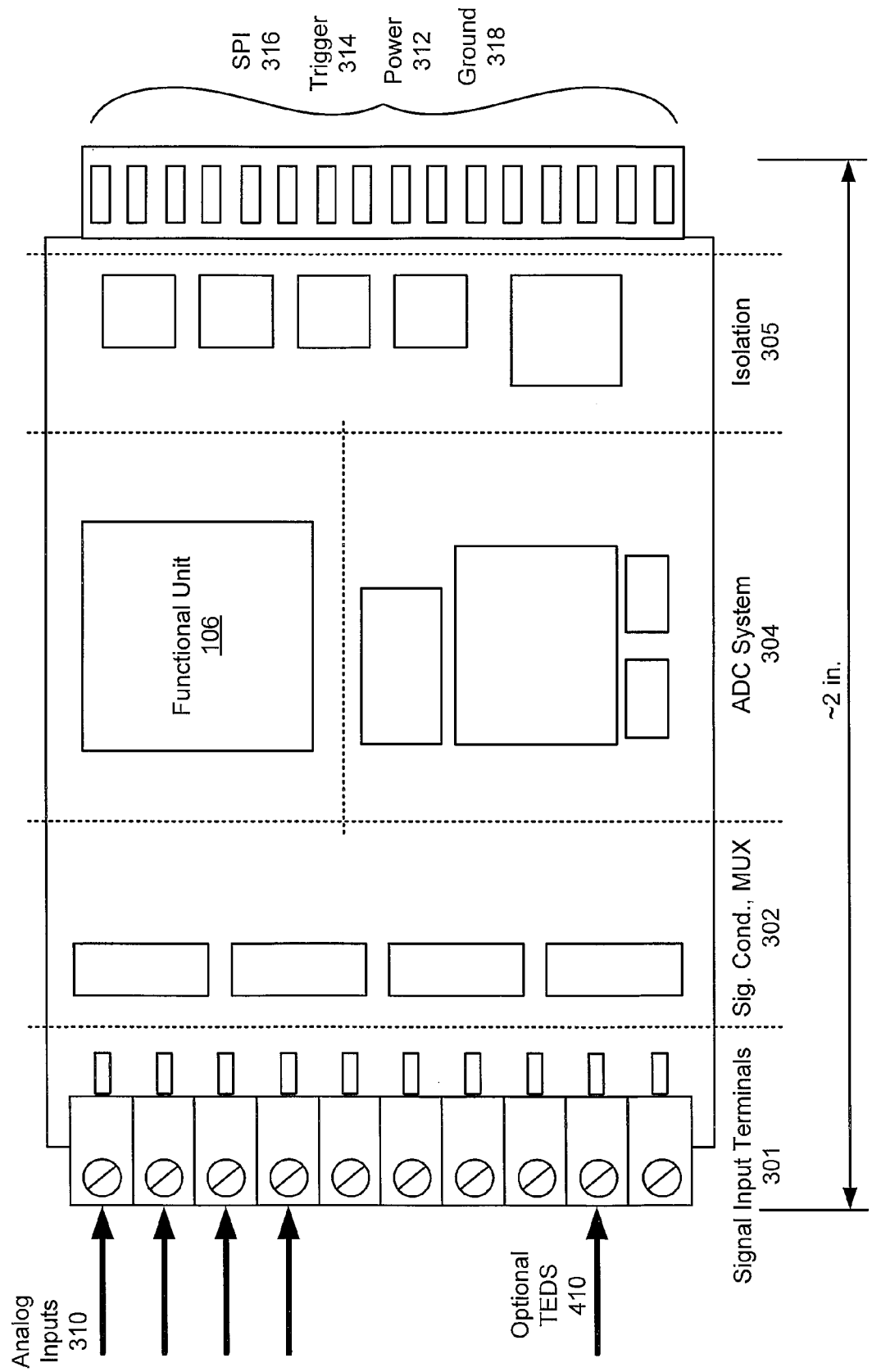
FIG. 5C illustrates a hardware layout of a measurement module, according to one embodiment of the invention.

FIG. 5C—Measurement Module Hardware Layout

FIG. 5C illustrates one embodiment of a hardware layout of the measurement module 108. Note that FIG. 5C only illustrates the functional components of the module, and that in the preferred embodiment, a housing or chassis may be included for enclosure, protection, or support of the module components, as illustrated in FIGS. 5A and 5B, and FIG. 7B, described below.

As FIG. 5C shows, in one embodiment, a printed wiring board (PWB) may be equipped with signal input terminals 301 for receiving analog inputs 310, e.g., from a sensor 112. In one embodiment, a subset of the input terminals 301 may be used to receive an optional Transducer Electronic Data Sheet (TEDS) describing the functionality of the transducer (e.g., sensor 112) in machine-readable form.

The PWB of the measurement module 108 may further include signal conditioning logic or circuitry 302, such as signal conditioners, MUXs, etc., which may be operable to receive the signals from the analog inputs 310 and perform signal conditioning on the signals, as is well known in the art.

As FIG. 5C also shows, the PWB may also include signal conversion logic or circuitry 304, such as the ADC shown, which may be operable to receive the conditioned signals from the signal conditioning circuitry 302 and perform any of various signal conversion operations on the signals. In the embodiment shown, the ADC 304 may operate to convert the conditioned analog signals to digital signals. Of course, in other embodiments, other signal conversions may be performed as desired, including digital to analog, or any other signal conversion.

As indicated above, in one embodiment, the PWB may include a functional unit 106, such as a processor/memory 306 and/or a programmable hardware element, such as an FPGA 308. As described above, the functional unit 106 may operate to provide an interface between the signal conditioning/conversion components 302/304 and external systems, such as computer system 102. As also mentioned above, the functional unit 106 may be operable to communicate interface protocol information to a carrier 110 indicating how to communicate with and operate the measurement module 108.

In one embodiment, isolation circuitry 305 may also be included on the PWB which may be operable to protect the components of the measurement module from spurious signals, signal noise, harmful voltage and/or current surges, impedance mismatches, and the like.

As FIG. 5C also shows, the PWB may also include terminals for communicating with external systems such as the computer system 102, including SPI 316, trigger line(s) 314, power 312 and ground 318 lines, among others.

In one embodiment, the measurement module 108 may comprise a cartridge, e.g., a measurement cartridge, which may be operable to be inserted into a slot in a chassis, described in detail below.

One benefit of the measurement module design presented above relates to cost. For example, in one embodiment of the measurement module 108, the cost may be estimated in the following way (in U.S. dollars circa 2001):

Basic System:

| | |
|---|---|
| PWB: | $4.50 |
| Screw Terminals: | $4.00 |
| Enclosure/label: | $1.10 |
| Manufacturing: | $10.00 |
| Total (w/o isolation) | $19.60 |
| Isolation: | $12.50 |
| Total (w/ isolation) | $32.10 |

Feature Circuitry:

| | |
|---|---|
| Micro-Processor: | $5.00 |
| Signal Conditioner, MUX: | $5.00-10.00 |
| ADC System: | $7.00-10.00 |
| Total (w/ isolation) | $49.10-57.10 |

Thus, for less than $60, the measurement module described above may be manufactured, resulting in a versatile and affordable DAQ/measurement solution. Other examples of estimated costs for measurement cartridges are given below:

| | Estimated Cost to Builds | |
|---|---|---|
| Cartridge | Non-Iso | Isolated |
| Slow 4-ch AI | | |
| 16-bit ADC, 0-1 V, 0-10 V | $42.60 | $55.10 |
| Fast 4-ch AI | | |
| 12-bit ADC, 50 kS/s | 36.60 | 49.10 |
| 4-ch T/C | | |
| 16-bit ADC, + −1 deg C. | 39.60 | 53.10 |

-continued

| Cartridge | Estimated Cost to Builds | |
|---|---|---|
| | Non-Iso | Isolated |
| 4-ch AO | | |
| 12-bit DAC, 0-10 V | 50.60 | 63.10 |
| 3-ch RTD | | |
| 3-wire, 16-bit ADC | 41.60 | 54.10 |
| 8-ch DI (5-30VDC) | 25.60 | 38.10 |
| 8-ch DO (5-30VDC) | 29.10 | 41.60 |

Examples of Estimated Costs for Simple Network Adapters/Carriers—CTB:

| | Estimated Cost to Builds | |
|---|---|---|
| | 4-SLOT | 1-SLOT |
| Serial RS-232 | $71 | $61 |
| Serial RS-485, isolated | 80 | 70 |
| Simple USB | 66 | 56 |
| Simple Ethernet | 80 | 70 |
| Ethernet w/ 32-bit uproc | 150 | 140 |

Figure 6:
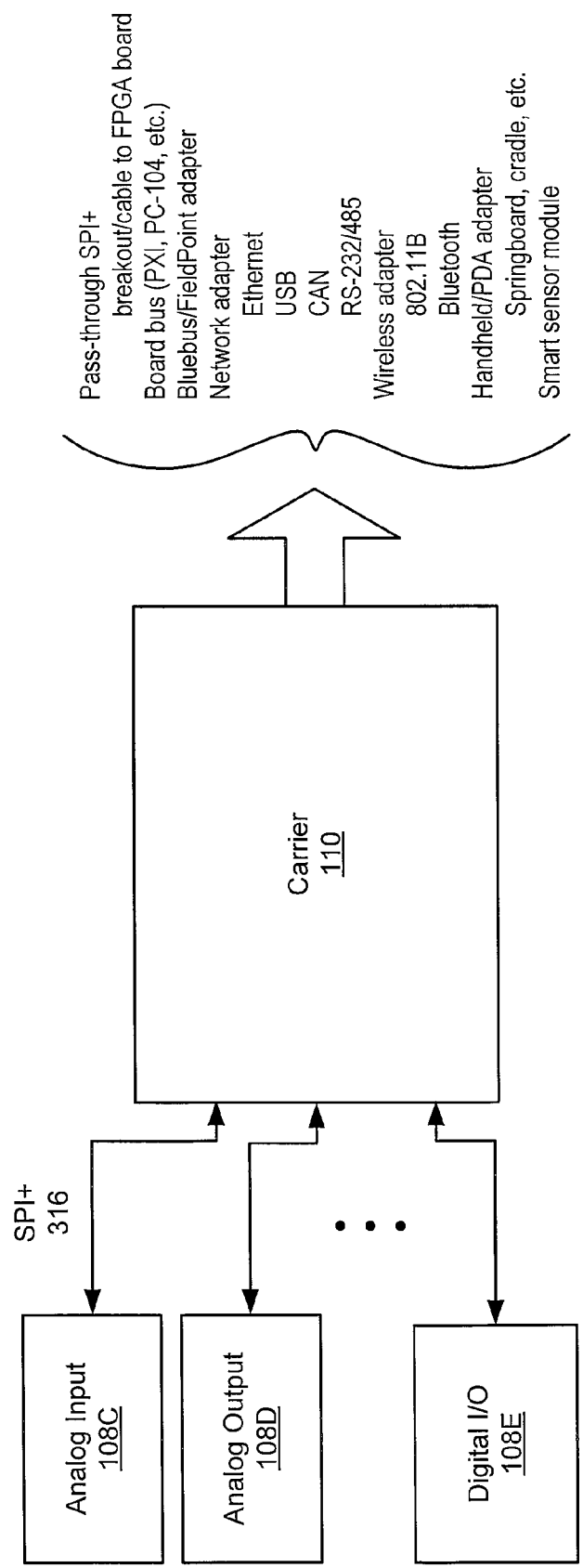
FIG. 6 is a block diagram of a carrier with multiple measurement modules, according to one embodiment of the invention.

FIG. 6—Multiple Measurement Modules with Carrier

FIG. 6 is a block diagram of a measurement system comprising a carrier 110 and a plurality of measurement modules 108, according to one embodiment. As FIG. 6 shows, the plurality of measurement modules 108 may include analog input module 108C, analog output module 108D, and digital I/O module 108E, as well as other measurement modules not shown. Thus, the carrier 110 may be operable to communicate with each measurement module 108 and be programmed or configured (e.g., by a computer system 102 or by a processor/memory on the carrier 110) to implement the respective interface of each measurement module. In this manner a suite of sensors 112 may be fielded, each of which feeds signals to a respective measurement module 108 which in turn communicates through a respective interface (protocol) with the carrier 110. Thus, the carrier 110 may support a heterogeneous plurality of interfaces without having to include a heterogeneous set of interface hardware components.

It should be noted that in various embodiments, the carrier 110 may also be operable to perform other functions in addition to the adaptive interface functionality described above. For example, in one embodiment, the carrier may include network control circuitry (or have a functional unit configured to perform network control functions), and thus may comprise a networked measurement and control device, or a networked data acquisition device. In other words, the carrier unit may comprise one or more of an Ethernet carrier, a USB carrier, and a wireless carrier, among others, to facilitate transmission of data over a network to external systems, e.g., the computer system 102.

In one embodiment, the carrier 110 may include an IP address and web server capabilities. Thus the carrier unit may be able to publish received signals or measurement data over the Internet. The carrier 110 may similarly be operable to receive signal data over the Internet for processing. In another embodiment, one or more measurement cartridges 108 coupled to the carrier 110 may have an IP address and web server capabilities, and thus may be able to communicate with remote systems over the Internet, for example, to stream sensor data (e.g., numerical data or images) to a website for access by other systems or users.

In one embodiment, the carrier 110 may include a module 108 comprising a computer on a card, i.e., the functions of the computer system 102 may be performed by a module comprised in a slot on the carrier 110.

In one embodiment, the carrier unit 110 may comprise a measurement and control system, such as an industrial programmable logic controller, and may include one or more of a real time controller and an embedded controller.

In another embodiment, the measurement and control system may be usable in a PC based measurement and control system, and example of which is illustrated in FIG. 1A. For example, the carrier 110 may comprise or be operable to couple to a PC, i.e., computer system 102, and may be operable to perform measurement and control functions using the PC's processor 160 and memory 166. In one embodiment, the PC based measurement and control system may comprise one or more of a real time controller and an embedded controller. In another embodiment, the PC based measurement and control system may comprise one or more of a PCI carrier and a PXI carrier. In another embodiment, the carrier itself may comprise one or more of the PCI carrier and the PXI carrier.

In yet another embodiment, the carrier may comprise a DAQ-in-cable, e.g., used in a PC based DAQ or measurement system. In other words, the carrier 110 may be comprised in a cable connector, where one end of the cable is operable to be connected to the computer system 102, or to a network device, and the other end is operable to be connected to a measurement module. Thus, the cable itself may operate to perform various DAQ and/or measurement or analysis functions. Other embodiments of the carrier 110 are described below with reference to FIGS. 7A-13.

As FIG. 6 shows, the carrier 110 may receive signals from the measurement modules 108, optionally process the signals, and send the signals (or results) on to other systems and/or components of the measurement system. For example, as indicated by FIG. 6, the carrier 110 may transmit the signals to one or more of a Pass-through SPI+, e.g., a breakout/cable to FPGA board; a board bus (PXI, PC-104, etc.); Bluebus/FieldPoint adapter; a Network adapter, such as Ethernet, USB, CAN, or RS-232/485, among others; a wireless adapter, such as 802.11B or Bluetooth; a Handheld/PDA adapter, for example, Springboard, cradle, etc.; and a smart sensor module, among others.

FIGS. 7A and 7B—Measurement Cartridges with Cartridge Carrier

FIGS. 7A and 7B illustrate embodiments of the invention where the measurement module 108F is in the form of a measurement cartridge and the carrier 110 is in the form of a cartridge carrier 110A which is operable to receive one or more of the measurement cartridges 108F. FIG. 7A illustrates an embodiment in which the cartridge comprises a card with no housing, whereas FIG. 7B illustrates an embodiment in which the cartridge includes a housing, as shown.

In one embodiment, the carrier unit 110A may comprise a chassis, a backplane comprised in the chassis providing for electrical communication, a functional unit and one or more slots comprised in the chassis. Each of the one or more slots may include a connector that is coupled to the backplane, where each of the one or more slots may be adapted for receiving one of the measurement modules 108F. Thus, the carrier 110 may host a plurality of measurement cartridges 108F, each of which may provide measurement and/or control functionality for a measurement or control operation or task. As mentioned above with reference to FIG. 6, the carrier 110A may be operable to communicate with each measurement cartridge (i.e., module) 108F and be programmed or configured (e.g., by a computer system 102 or by a processor/memory on the carrier 110) to implement the respective interface of each measurement cartridge. In this manner a suite of sensors 112 may be fielded, each of which feeds signals to a respective measurement cartridge 108F which in turn communicates through a respective interface (protocol) with the cartridge carrier 110A. Thus, the carrier 110A may support a heterogeneous plurality of interfaces without having to include a heterogeneous set of interface hardware components. In one embodiment, a channel or bus may be provided by the carrier 110 for each cartridge/interface protocol. In other words, each slot may have an associated dedicated bus for that slot, with a corresponding portion of the carrier's reconfigurable hardware configurable to implement the interface for a cartridge inserted into the slot. In another embodiment, the carrier 110 may include a shared bus or backplane common to a plurality of the slots, where inserted cartridges may communicate through the common bus or backplane with the reconfigurable hardware of the carrier 110 in accordance with the respective interface protocols implemented on the reconfigurable hardware.

In a preferred embodiment, the measurement modules 108 (or cartridges) may be easily removed, added, and replaced. In other words, measurement modules may be exchanged to change the configuration or capabilities of the measurement system. In one embodiment, the measurement module 108 may be replaced without powering down the measurement system, i.e., the measurement module 108 may be "hot-plugged" into the carrier 110, where, during operation of the measurement system, the measurement module 108 may communicate the interface protocol information to the carrier 110 upon attachment, and the carrier 110 is programmed in response, as described above. In another embodiment, the measurement module 108 and/or carrier 110 may require a reboot or reset after attachment to perform the described initialization.

For example, during operation of the measurement system, a new measurement module 108 (or cartridge) may be added (i.e., inserted or attached) to the carrier 110. The measurement system may automatically perform the initialization described above with respect to the added measurement module 108. In other words, during operation of the measurement system, the newly coupled measurement module 108 may communicate respective interface information to the carrier 110, which may then be programmed (e.g., by the computer system 102 or by a processor/memory on the carrier 110) to implement the respective interface, thereby enabling operations with the new measurement module 108. In one embodiment, the new measurement module 108 may replace another measurement module which was removed during operation of the measurement system.

Thus, the interface circuitry (i.e., the measurement module 108) being operable to communicate the interface protocol to the carrier unit 110 describing the interface may comprise the interface circuitry being operable to communicate the interface protocol to the carrier unit 110 upon one or more of attachment of the measurement module to the carrier unit, reset of the measurement module, reset of the carrier unit, reboot of the measurement module, and reboot of the carrier unit.

As FIGS. 5C, 7A, and 7B show, in a preferred embodiment, the measurement module 108 may have a small form factor. For example, in one embodiment, the measurement module 108 may have dimensions less than or equal to approximately 1 inch by 2 inches by 3 inches. In one embodiment, the measurement module may have dimensions of approximately 0.2 inches by 1 inch by 1 inch or more. In yet another embodiment, the measurement module may have dimensions of approximately 0.8 inches by 2.5 inches by 3.4 inches or more. Thus, in a preferred embodiment, the measurement module 108 has a compact form factor which may enable deployment in a variety of devices or carriers with minimal space requirements.

Thus, in one embodiment, the measurement module 108 may comprise a measurement cartridge including signal conditioning, ADC, microprocessor, and optional isolation, for sensor to digital operations. Additionally, the cartridge may provide an SPI digital interface with simple protocol, and EDS/calibration history on board. In a preferred embodiment, the cartridges may have low channel counts, e.g., 4-channel analog, 8-channel digital.

The cartridge carriers are preferably able to convert SPI to standard bus/network signals, and implement power-on states, plug and play, and watchdogs. Additionally, the cartridge carriers may be provided with application-specific form factors and functions. In other words, the cartridge carriers may be developed specifically to match the customers space and function needs. Example carriers 110 may include, but are not limited to, 4-slot Ethernet carrier, 4-slot and 1-slot USB carrier, multi-slot RIO carrier, 1-slot wireless carrier, and CAN carrier, among others.

Thus, in various embodiments, the measurement modules or cartridges may provide any or all of low first channel cost, low power requirements, small size, "good" DAQ performance (for example, ~50 kS/s 12-bit to 10 S/s 20-bit), integrated signal conditioning, optional isolation, support for plug and play sensors (IEEE 1451.4), and easy use and configuration. Additionally, the measurement modules/cartridges may be rugged, i.e., may be suitable for industrial use. In various embodiments, the cartridges may plug into one or more of an Ethernet carrier, a USB carrier, an Ethernet Vision I/O slot, a PXI carrier, a PCI carrier, handhelds, DAQ in the cable, and RIO devices (e.g., panelettes), among others. Example functions contemplated for measurement cartridges include, but are not limited to, thermocouples, analog (e.g., 10 V) inputs, fast AI/vibration, analog output (e.g., 1V to 10V), digital input (e.g., 5V to 30V), and digital output (e.g., 5V to 30V).

Re-Configurable I/O Systems

In one embodiment, the measurement system may include a measurement module coupled to a "RIO" Reconfigurable I/O carrier 110D, also referred to as a generalized carrier 110D. As used herein, the term "RIO" carrier refers to a carrier which includes reconfigurable hardware, e.g., an FPGA, which is configurable with respective interface protocols for one or more cartridges. In other words, a RIO carrier 110D with multiple cartridge slots may be configured with multiple interfaces for inserted cartridges, such that each cartridge's interface is implemented by the RIO carrier 110D.

In yet another embodiment, the RIO carrier 110D may be configurable to include not only the adaptive interface functionality described above, but may also include or may be configured to include, one or more measurement and/or control functions. For example, the carrier may perform all or a portion of timing, triggering, and synchronization functions for inserted cartridges or modules. Further descriptions of RIO based embodiments of the invention are presented below with reference to FIGS. 7C-7D and FIGS. 8A-11, described below.

Figure 7D:
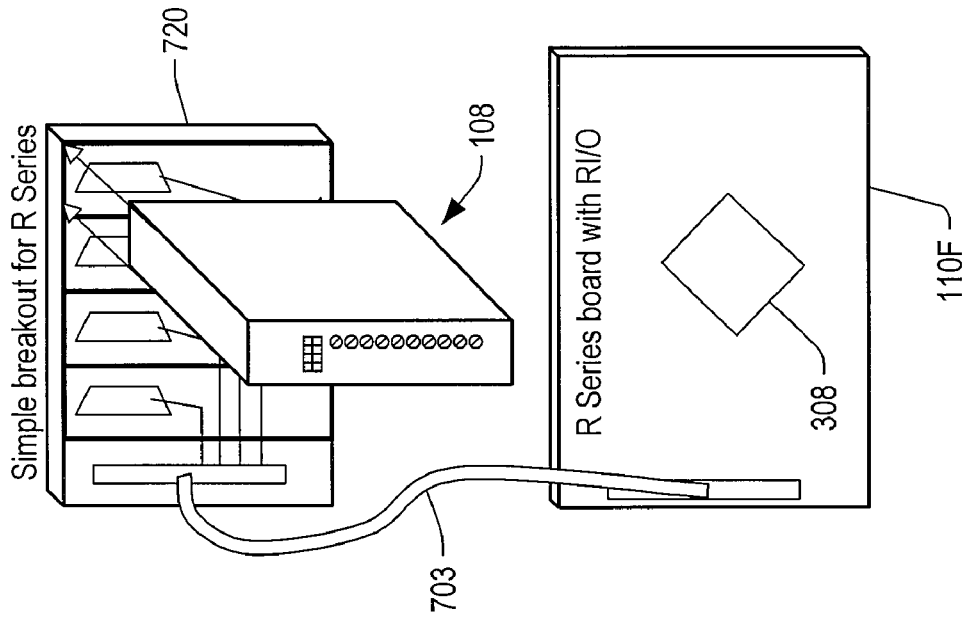
FIGS. 7C and 7D illustrate embodiments of measurement cartridges used in RIO systems.
Figure 7C:
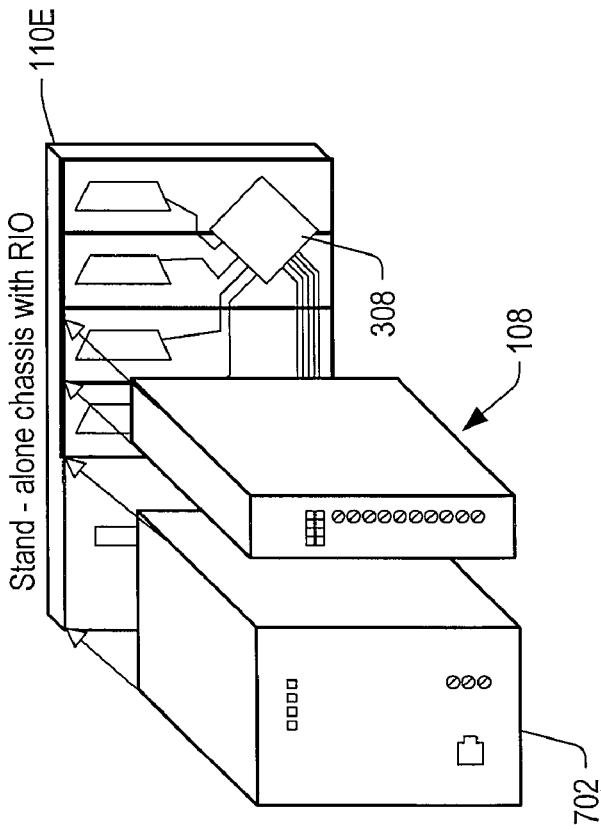

FIGS. 7C and 7D—Measurement Cartridges in RIO Systems

FIGS. 7C and 7D illustrates two embodiments of measurement systems using measurement modules with RIO carriers 110. FIG. 7C illustrates an embodiment in which the measurement module (or cartridge) 108 is coupled to a stand-alone chassis with RIO 110E, which may function as the RIO carrier 110 for the system. In other words, the chassis 110E includes a RIO functional unit 308, e.g., on or coupled to the chassis backplane, for implementing the interface protocol of the measurement cartridge 108, and/or for providing other RIO functionality. Additionally, in this embodiment, a controller cartridge or module 702 may be coupled to or inserted into the chassis 110E, and may provide one or more of a power supply, communications (e.g., Ethernet, USB, 1394, etc.), real time application software, such as LabVIEW/RT from National Instruments, executable by an on-board processor and memory (comprised on the controller 702), and a PCI bus to RIO. The controller 702 may thus provide some or all of the functionality which might normally be provided by a host computer 102, as described above, thereby allowing the system as shown to operate without the host computer 102. In other words, in one embodiment, the controller 702 may function as the host computer system 102.

FIG. 7D illustrates another embodiment of a RIO-based measurement system, in which the RIO functionality (e.g., the RIO FPGA 308) is provided by an R Series board 110F which is coupled to a simple breakout for R Series 720 by a transmission medium, e.g., a 68 pin cable 703, as shown. The breakout 720 is also operable to receive the measurement cartridge 108, and so may function as a cartridge chassis. In on embodiment, the R Series board, in addition to the RIO FPGA 308, may include a processor and memory, and thus may provide the functionality of a host computer 102, e.g., storing and executing application software, programming the RIO FPGA with the module interface protocol, etc. In another embodiment, the breakout 720 may couple to an external computer system 102, e.g., via a transmission medium. In yet another embodiment, a computer-on-a-card, may be inserted into the chassis 720, and may serve as the host computer 102, as described above.

Thus, in some embodiments, the carrier 110 may include a processor and memory which may provide some or all of the functionality of the host computer system 102, described above. The processor and memory of the carrier 110 may be operable to store and execute real time application software, such as LabVIEW/RT.

For example, in one embodiment, the carrier 110 may comprise a C-Series platform (e.g., from National Instruments), which may support a variety of multi-slot chassis, e.g., a 16-slot chassis, an 8-slot chassis, a 4-slot chassis, among others, and may facilitate high-speed real time control (e.g., 10× to 100× loop performance versus PLCS). The carrier may include a 1-slot multi-drop bus adapter. The platform may also include a stand-alone x86 controller module with LabVIEW/RT. In one embodiment, the carrier 110 may be DIN-rail and panel mounted. Additionally, the carrier may be configured with a RIO personality, such as, for example, a personality for synchronous single-point acquisition. In one embodiment, the carrier 110 may support an option to distribute individual cartridges through one-slot deterministic bus adapters. This and similar embodiments of the inventions may be suitable for such applications as fast machine control, embedded systems, distributed monitoring, hardware-in-the-loop, and data acquisition, among others.

In another embodiment, the carrier 110 may comprise an M-Series platform (e.g., from National Instruments), which may also support a variety of multi-slot chassis, e.g., a 16-slot chassis, an 8-slot chassis, a 4-slot chassis, among others. This and similar embodiments may facilitate economical portable measurements, such as, for example, by using low-cost communications modules (e.g., USB, 1394), and/or a low-cost 1-slot USB bus adapter. This embodiment may not, for example, use a real time program such as LabVIEW/RT. The carrier 110 may be configured with a RIO STC-like personality, such as, for example, a personality for generating synchronized, triggered waveforms. Cartridges suitable for use with the carrier may have BNC, mass termination connectors. The carrier 110 may be implemented as a benchtop, desktop, in-vehicle, and/or rack-mounted system, as desired, and may be suitable for such applications as external/portable DAQ, in-vehicle testing, and rack-mount I/O for testing, among others.

Thus, in various embodiments, the RIO functionality of the measurement system may be comprised in or on various different components of the measurement system.

Figure 8A:
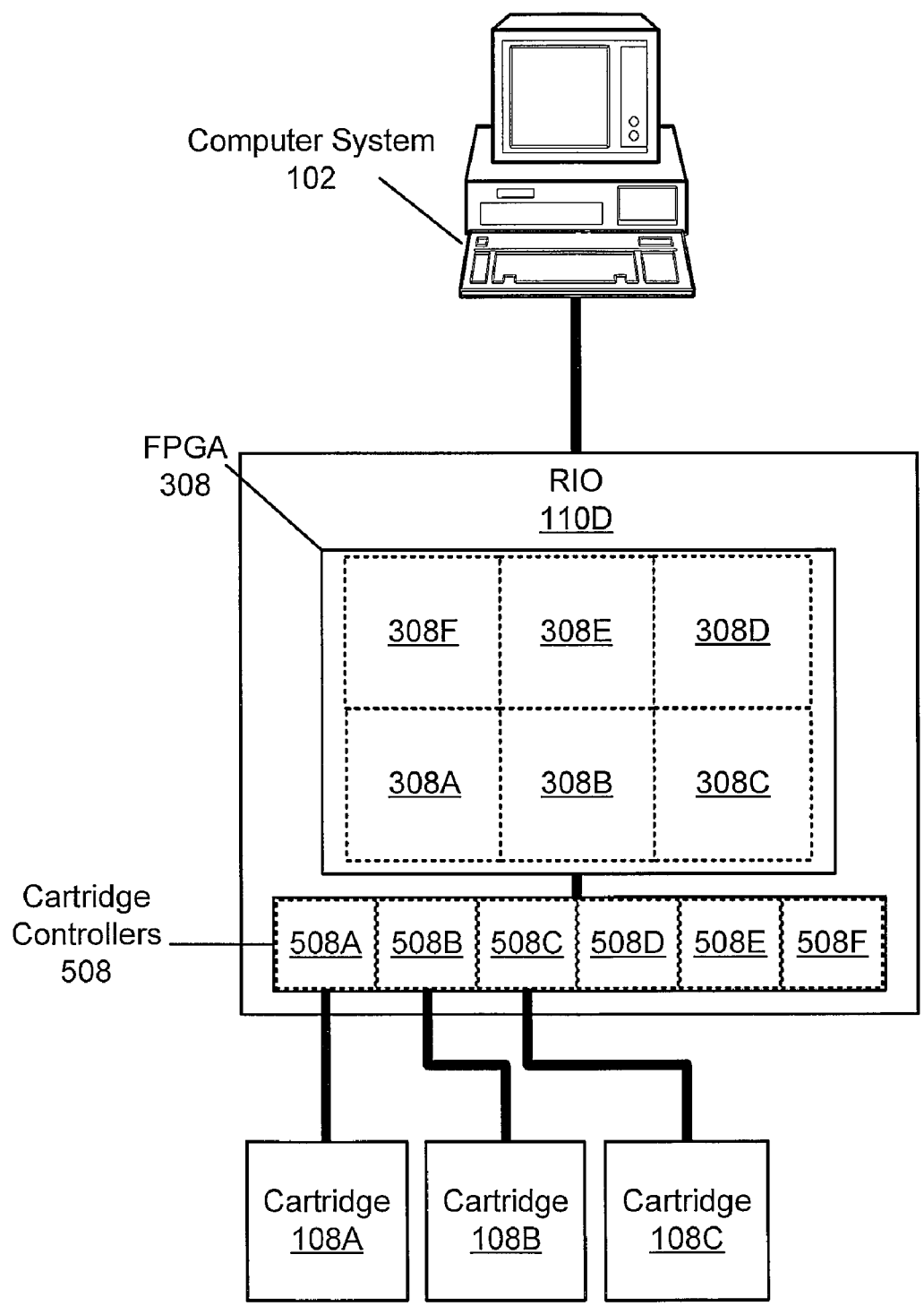
FIG. 8A is a block diagram of a cartridge carrier in a RIO system with separate cartridge channels, according to one embodiment.
Figure 8B:
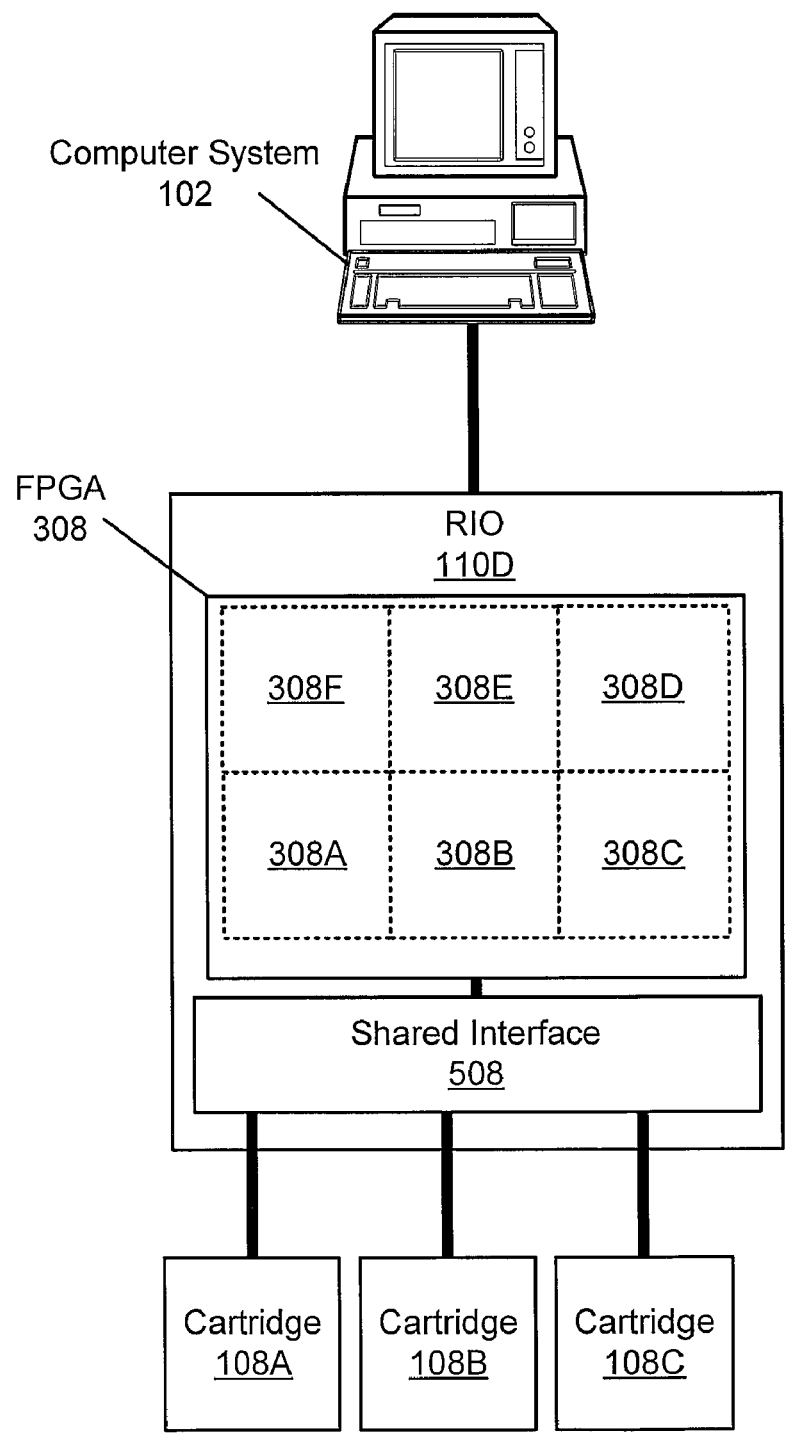
FIG. 8B is a block diagram of a cartridge carrier in a RIO system with a shared cartridge bus, according to one embodiment.

FIGS. 8A and 8B—Block Diagrams of a Cartridge Carrier in a RIO System

FIGS. 8A and 8B are block diagrams of two embodiments of a cartridge carrier 110 in a RIO system, i.e., a RIO carrier 110D. As both FIG. 8A and FIG. 8B show, the RIO cartridge carrier 110, also referred to as a "RIO" 110D, may couple to computer system 102, as described above, and may be operable to receive multiple cartridges 108, e.g., in respective slots in the RIO 110D. As FIGS. 8A and 8B also show, the RIO 110D may include a programmable hardware element, e.g., an FPGA 308 which is operable to be configured with a variety of measurement module interface protocols (MMIPs), also referred to as "personalities", in that the implemented personality corresponds to a particular measurement module, module type, or module configuration/functionality. In one embodiment, each MMIP may be configured in a respective portion of the programmable hardware element 308. For example, the MMIP for cartridge 108A may be configured in portion 308A of the FPGA, the MMIP for cartridge 108B may be configured in portion 308B of the FPGA, and so on.

FIG. 8A is a block diagram of an embodiment of the cartridge carrier or RIO 110D with separate cartridge controllers for each cartridge slot. In other words, in this embodiment, the cartridge carrier includes separate channels or buses 508A, 508B, 508C, etc. for each respective cartridge slot, such that each cartridge inserted into the RIO carrier 110D may communicate with the FPGA 308 through a respective interface, channel, or bus.

FIG. 8B is a block diagram of an embodiment of the cartridge carrier or RIO 110D with a shared cartridge controller 508. Said another way, in the embodiment of FIG. 8B, a single shared bus may provide for communication between cartridges 108 inserted into slots of the RIO 110D and the programmable hardware element 308, e.g., FPGA, in the RIO 110D. In one embodiment, communication with the inserted cartridges 108 may be performed by allocating respective time-slots for communication with each cartridge 108, i.e., through time domain multiplexing (TDM), as is well known in the art, although other techniques for communicating over a shared bus or interface are also contemplated. It is noted that in other embodiments, the RIO system may use other module forms besides cartridges. In other words, the concepts presented herein with respect to cartridge carriers 110 and cartridges 108 may be applied to embodiments where the modules are not specifically in the form of cartridges. Further details of the RIO cartridge carrier 110D and cartridge controllers 508 are presented below with reference to FIGS. 9 and 10, respectively.

Figure 9:
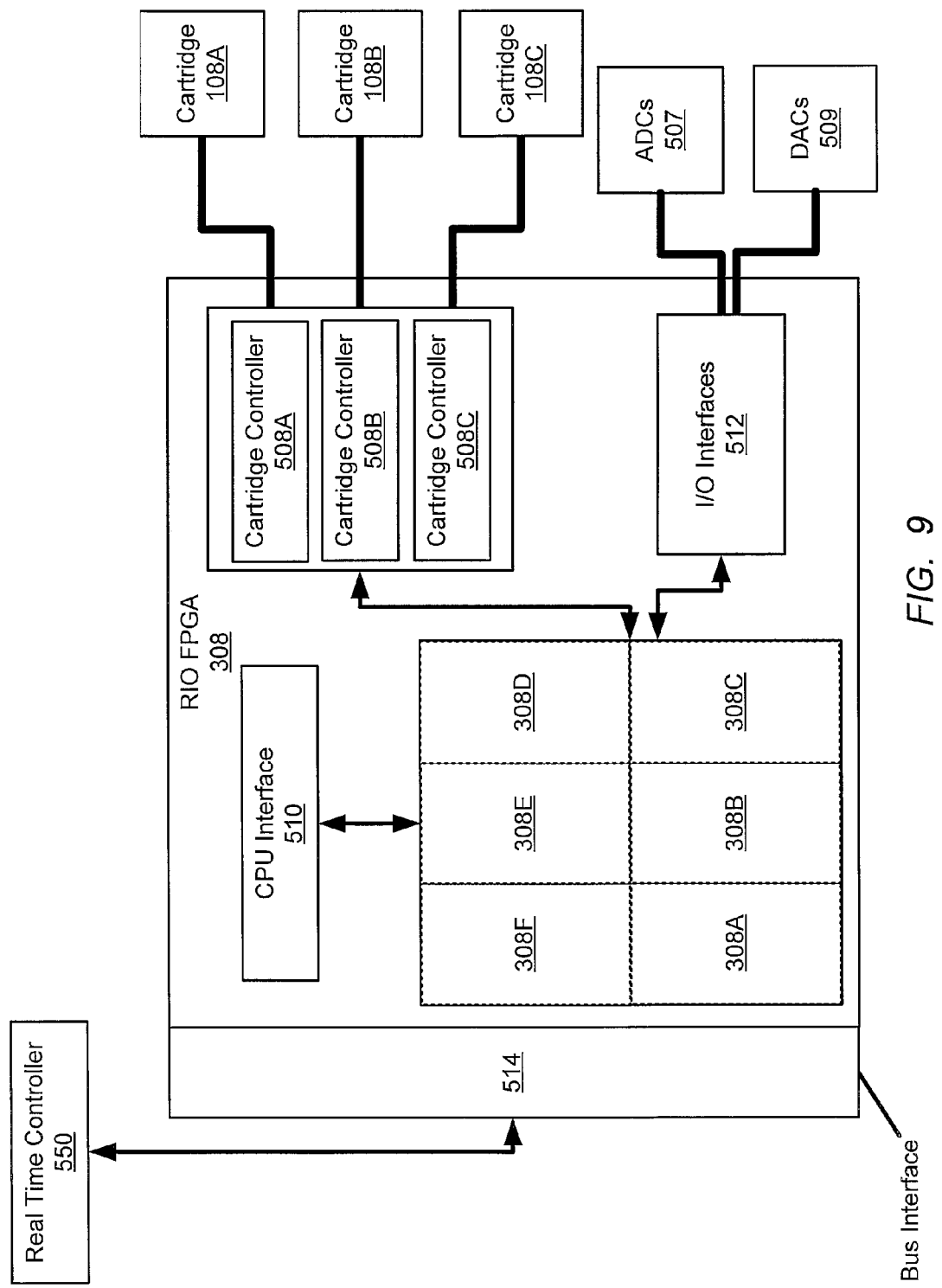
FIG. 9 is a block diagram of a cartridge carrier, according to one embodiment.

FIG. 9—Block Diagram of a Cartridge Carrier

FIG. 9 is a block diagram of a RIO FPGA 308 comprised in a cartridge carrier 110, according to one embodiment. In this embodiment, the RIO FPGA 308 may provide a hardware interface between controlling software, such as an application program executing on computer system 102 or on the carrier 110D, for example, and the individual cartridge 108.

As FIG. 9 shows, the RIO FPGA 308 may be configured to include a variety of interface components, including, for example, a bus interface 514 for communicating with a real time controller 550; a CPU interface 510 for communications between a processor (e.g., on computer system 102 or on the carrier 110D) and portions of the FPGA configured with respective MMIPs, e.g., 308A-308F, as shown; and I/O interfaces 512 for communications between the FPGA MMIP portions and external signal converters, such as ADCs 507 and DACs 509. As FIG. 9 further shows, the RIO FPGA 308 may also include one or more cartridge controllers 508, e.g., 508A-508C as shown, which facilitate communication between the FPGA MMIP portions and respective inserted cartridges 108A-108C. As mentioned above with reference to FIGS. 4A-6, communications with the cartridges 108 may performed over a plurality of SPI lines 316, as well as auxiliary lines, such as timing and trigger lines 314, collectively referred to as SPI+ (SPI-Plus). One embodiment of a cartridge controller 508 is provided below with reference to FIG. 10A.

Figure 10A:
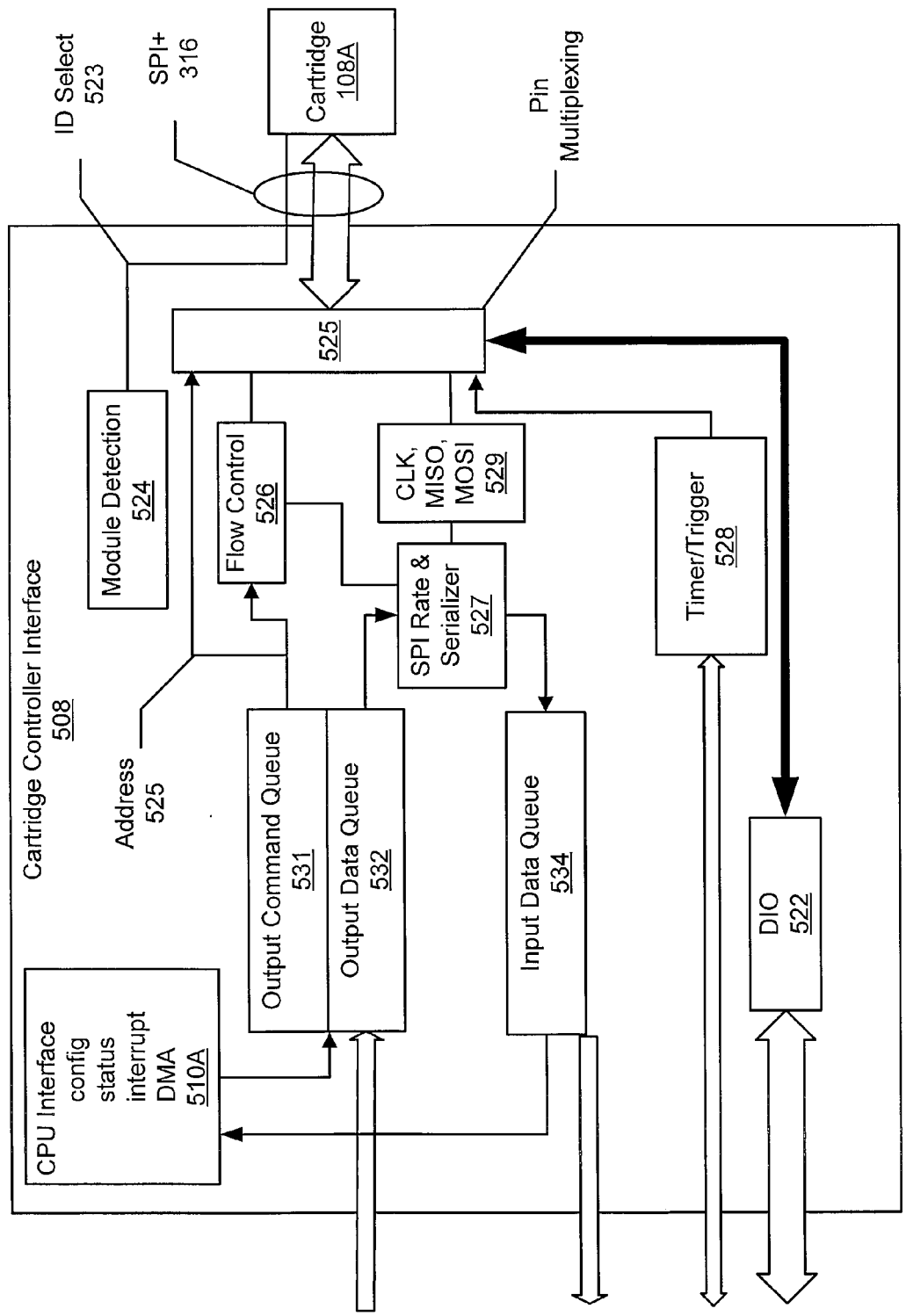
FIG. 10A is a block diagram of a cartridge controller, according to one embodiment.

FIG. 10A—Block Diagram of a Cartridge Controller

As mentioned above, the RIO FPGA 308 may include one or more cartridge controllers 508 which may provide the basic functionality necessary to interface to a cartridge 108. FIG. 10A is a block diagram of one embodiment of a cartridge controller 508, where the cartridge controller is a component of a RIO system 110D, and where the cartridge controller 508 provides for communication between the RIO FPGA 308 (described above) and an inserted measurement module/cartridge, e.g., cartridge 108A. The cartridge controller 508 may behave much like other standard interfaces to fixed resources on the RIO board, such as ADCs, DACs, and DIO. Additionally, the cartridge controller 508 may be configurable by the MMIP portion of the FPGA 308, e.g., to mediate communications with the cartridge in accordance with the configured MMIP. In various embodiments, the cartridge controller 508 may be used as a fully functional block or as part of an FPGA diagram, such as a LabVIEW FPGA diagram.

Important aspects of the basic functionalities provided by the cartridge controller 508 include the facilities to detect cartridge insertion and to communicate with the EPROM 307 of a cartridge to identify the cartridge. The SPI interface, i.e., the plurality of wires coupling the cartridge controller 508 to the cartridge, is also used to communicate with the cartridges functionally (as opposed to simple identification) and is designed to provide high performance communication between the cartridges 108 and the cartridge controller 508. Beyond the basic functionality, the cartridge controller 508 may include a set of modular blocks that may be included based on the needs of the implementation, including, for example, queues, timer, triggers, and digital I/O (DIO) support, described below. The cartridge controller block may also provide hooks so that when instantiated as a component in a graphical diagram, such as a LabVIEW FPGA diagram, the diagram may be able to provide user defined capabilities to the cartridge while maintaining basic functionality necessary for identification, such as, for example, through a DIO line 522.

As FIG. 10A shows, the cartridge controller 508 may include pin multiplexing 525 for coupling to the cartridge 108A. In a preferred embodiment, the measurement cartridges 108 are hot-swappable and interchangeable, and may necessitate a notification mechanism which operates when a cartridge is removed or inserted. Thus, a module detection component 524 may also be included which may be operable to detect the cartridge 108A, e.g., via an ID select line 523, as shown. In one embodiment, the cartridge controller 508 may monitor the ID select line 513 for any transition when the controller 508 is not driving the line. The transition may be captured and a bit set to notify the controlling software by polled IO or interrupt. The software may then read a status register to determine if a cartridge has been inserted or removed from the slot so that it may take appropriate action, e.g., reading the EPROM 307 on the cartridge 108 and configuring for an insertion or clean up for removal. Identification of the cartridge may be facilitated by the module detection component 524 in conjunction with an SPI rate and serializer component 527, also referred to as the SPI port 527, and an optional CPU interface 510A, which may provide information regarding configuration, status, interrupts, and DMA to a processor, e.g., on the carrier 110D or on the computer system 102. In one embodiment, the CPU interface 510A may enable the cartridge controller 508 to be configured by the CPU, e.g., by the computer system 102 or a processor on the carrier 110D.

In one embodiment, the ID select line 523 may be used to toggle between communicating with the EPROM 307 for ID purposes, and communicating with the cartridge for functional purposes, such as DAQ, control, etc. In other words, the cartridge may support the ID Select cartridge detection, and may also support SPI for reading the identification EPROM. When not in identification mode, the cartridge pins may be defined and used for any purpose, thus allowing for future flexibility. In one embodiment, two primary modes may be defined for the cartridge controller 508. In a basic SPI mode, the cartridge controller 508 may communicate over the SPI port 527 and use pins for converting data, indicating busy, and exchanging triggers and clocks. In another mode, the cartridge controller 508 may use eight pins for digital input and output. Upon power up or upon a cartridge change, the controller 508 may enter a tristate (high-Z) mode in which all the pins are tristate for protection. After reading the EPROM 307, the software may set the appropriate mode as needed.

In one embodiment, the cartridge controller may support a DIO mode which provides basic digital input and output reads allowing communication with static DIO pins. For example, the DIO mode may include timed DIO and may support buffered DIO, e.g., for control applications.

As mentioned above, primary timing signals may be sent to the cartridge through one or more timing signal lines, included in the SPI+interface. The cartridge controller 508 may provide a multiplexer for selecting a conversion signal from the local timer or system triggers. The system triggers may include a local "RTSI" bus and signal from user defined hardware. In one embodiment, the cartridge may provide a trigger signal that may be routed to the system triggers.

As FIG. 10A also shows, the cartridge controller 508 may also include an input data queue 534, as well as an output command queue 531 and an output data queue 532, for communicating with the MMIP portions of the FPGA, as well as the CPU interface 510A. As also shown, a DIO component 522 may also be included to facilitate digital communications between the cartridge 108A (via the pin multiplexing 525) and the MMIP portions of the FPGA 308. Similarly, a timer/trigger component 528 may be included for communicating timing and triggering signals to and from the cartridge 108A, as shown.

A flow control component 526 may operate to regulate or direct data flow between the output command queue 531, the SPI rate and serializer component 527, and the cartridge 108A. In one embodiment, the SPI rate and serializer component 527 may also be coupled to the cartridge (via pin multiplexing 525) through a plurality of SPI lines 529, e.g., CLK (clock), MISO (master in, slave out), and MOSI (master out, slave in) lines, as shown, which may provide for communication of clocking signals, as is well known in the art.

Thus, an efficient SPI port 527 may be desirable for communication not only with the ID EPROM 307 of the cartridge 108A, but also for functional communication with inserted cartridges 108. Many of the cartridges may be based on a variety of available SPI compatible or easily adaptable ADCs or DACs. SPI hardware/software interface performance may be a primary determining factor in the overall measurement system performance. In addition to the basic parallel-to-serial and serial-to-parallel conversion necessary to communicate efficiently, the SPI port 527 may provide a number of features to reduce software burden, including, for example, data queues to buffer data in each direction and hardware flow control. The data queue may allow blocks of data to be transferred from the software and to take up latency when the software is busy.

The SPI port 527 may also take over part of the control role for the cartridge 108A since the cartridge is simple by design. As FIG. 10A shows, the output queue may include "commands", as indicated by the output command queue 531, as well as data, as indicated by the output data queue 532, that indicate the addressing modes, whether to capture data, and flow control, among others. In addition a reload mode may be provided which allows a sequence of data/command to be repeated without software intervention. A common use case would be to load data necessary to configure a set of ADC reads, including waiting for conversion responses. With the output queue repeating, the software need only manage capturing the input data.

Figure 10B:
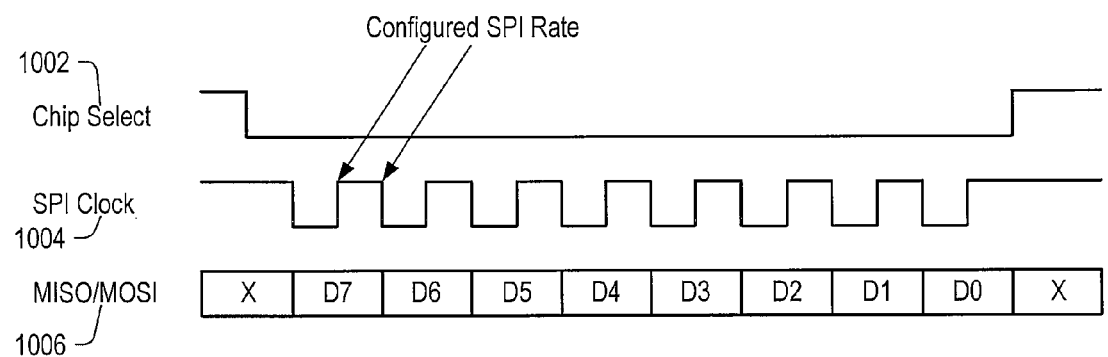
FIGS. 10B and 10C illustrate SPI signal timing, according to one embodiment.

In one embodiment, the SPI rate, i.e., the rate of data flow, may be configurable for each controller and may be changed on the fly to allow the maximum performance for a particular IC and topology. For example, the cartridge's EPROM 307 and ADC 507 may support different transfer rates via SPI. FIG. 10B illustrates a typical SPI cycle, according to one embodiment. As FIG. 10B shows, chip select signals 1002 may be asserted one half SPI period before the falling edge of an SPI clock signal 1004 and held a half period at the end of the cycle. The controller may drive data on the falling edge and sample the data on the rising edge of the SPI clock signal 1004.

As is common in high performance serial controllers, the input queue 534 and output queues 531 and 532 may provide a level of decoupling between the software and the hardware, i.e., the FPGA. The buffers may allow system latencies to be absorbed and lessen the processor load. The queue size may be adjusted for an implementation target, for example, a good minimum target may be one scan of data for a typical cartridge (four channels 32 bits). As mentioned above with respect to SPI, the output queues 531 and 532 may contain data and control information and may be set to automatically reload. The input queue 534 may capture data from the SPI input stream when indicated by the output command. Each of the queues may have optimized software interfaces for efficiently managing single point and buffer operations. Additionally, DMA capability may also be included for maximum performance where possible.

Figure 10C:
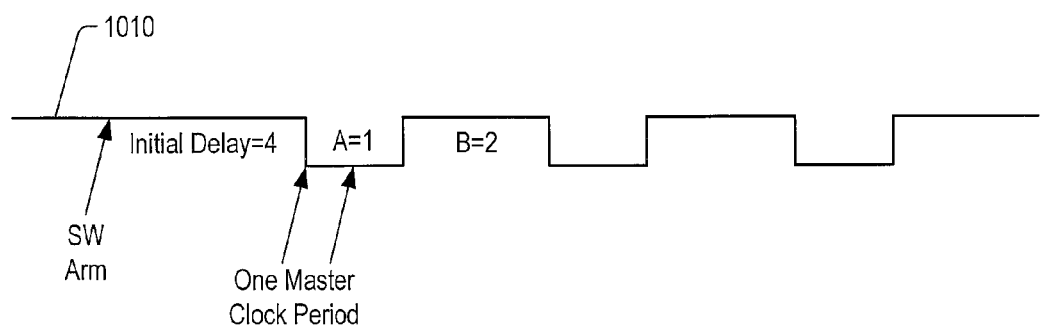

Because of the simplicity of the cartridge 108, the responsibility for providing compatible timing signals may fall on the controller 508. The timer 528 may provide for polarity and pulse width control of a signal that may be routed to the cartridge through a timing line. The timer may be used independently or as part of coordinated system timing with routing and hardware enables. An additional benefit is that the local timer may allow the cartridge to be completely functional without relying on system resources. FIG. 10C illustrates one embodiment of a common timer waveform 1010 where the initial polarity is high, and the waveform generates two periods low followed by three periods high.

An important feature in communicating with an ADC or DAC is the ability to determine or direct flow control, for example, waiting for a BUSY signal from the cartridge indicating the conversion is done, or a timer indicating when to write updates to a DAC. Wait blocks in conjunction with the output command queue 531 may allow the condition to be specified. In one embodiment, at any time, two conditions may be monitored. The source of the event and the desired edge may be programmed. When the wait command is at the head of the queue, the line may be monitored and the SPI data may not be transferred until the condition has occurred.

While the cartridge controller 508 may provide the necessary facilities to communicate and control most cartridges, more complex and sophisticated system functions may be realized by connecting to external resources, such as those available through LabVIEW FPGA, via external hooks. These hooks may provide for custom timing or triggering by coupling a diagram to timing and triggering signals. For improved flexibility, all the available pins may be made available to the user's diagram to provide complete control of the cartridge 108 while still allowing the controlling software to detect and identify cartridges via a standard mechanism. An example is coupling custom counter timers to transform a digital module. The external hooks may also be used to build a standard configuration of timing and triggering resources.

Registers

The following is an exemplary register set for the cartridge controller, representing one embodiment of a set of controls used for communicating with and controlling components of the cartridge controller 508. It is noted that these registers are exemplary only, and are not intended to limit the register set used by the invention to any particular set or interpretation.

| | | | |
|---|---|---|---|
| uD Status Register | Read | 16 bit | Offset 0x00 |
| uD Dout FIFO Status | Read | 16 bit | Offset 0x02 |
| uD Din FIFO Status | Read | 16 bit | Offset 0x04 |
| uD Din FIFO | Read | 16 bit | Offset 0x08 |
| uD DIO In Register | Read | 16 bit | Offset 0x0C |

-continued

| | | | |
|---|---|---|---|
| uD Signature | Read | 16 bit | Offset 0x0E |
| uD Control Register | Write | 16 bit | Offset 0x00 |
| uD SPI Rate Register | Write | 16 bit | Offset 0x02 |
| uD Timer A Register | Write | 16 bit | Offset 0x04 |
| uD Action Register | Write | 16 bit | Offset 0x06 |
| uD Dout FIFO Register | Write | 16 bit | Offset 0x08 |
| uD Control 2 Register | Write | 16 bit | Offset 0x0A |
| uD Timer B Register | Write | 16 bit | Offset 0x0C |
| uD DIO Out Register | Write | 16 bit | Offset 0x0E |

Figure 11A:
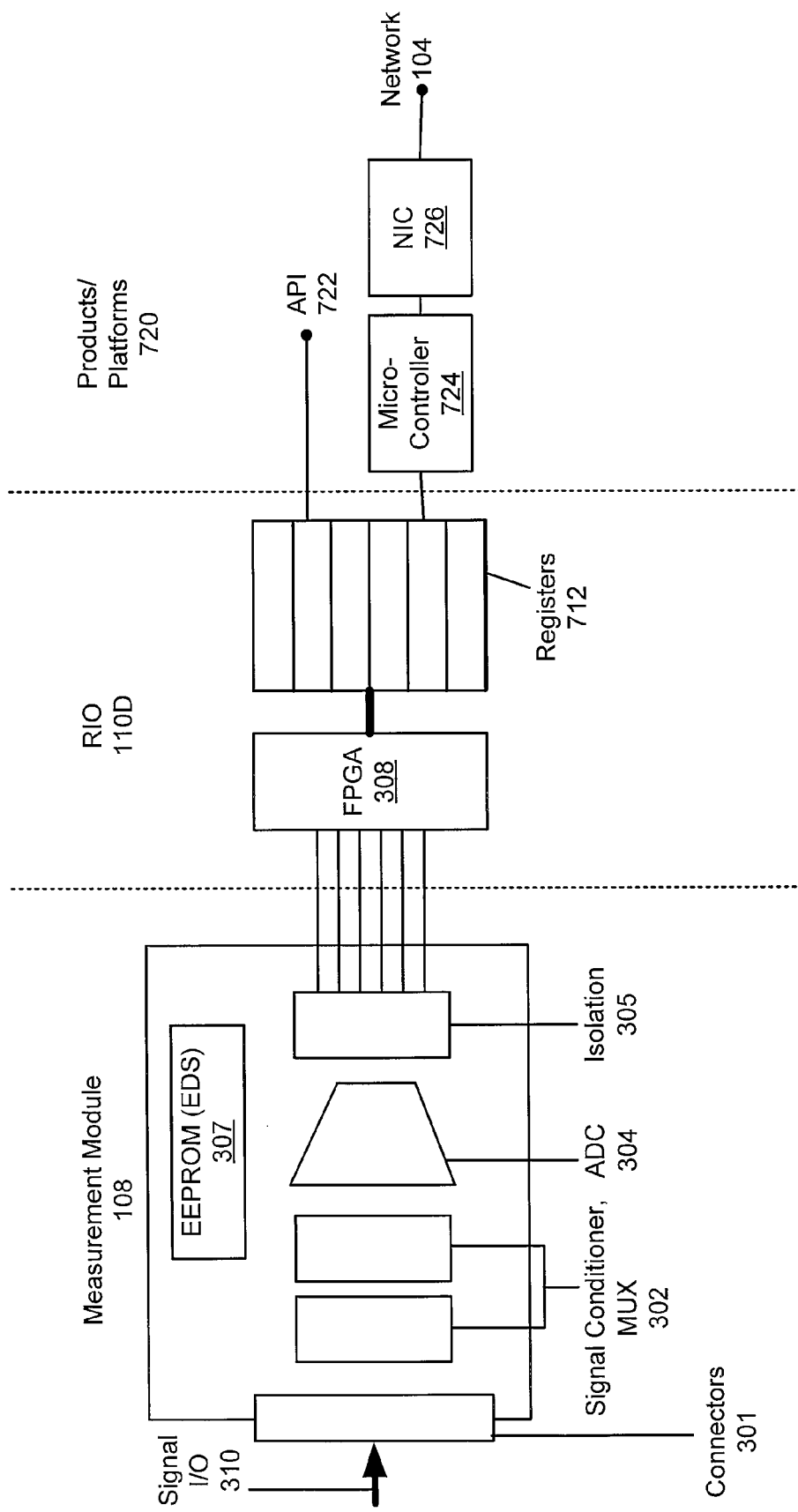
FIG. 11A is a block diagram of a measurement system using re-configurable I/O (RIO), according to one embodiment of the invention.

FIG. 11A—Measurement Module and Generalized Re-Configurable Carrier Architecture FIG. 11A is a block diagram of an architecture for a measurement system which includes a measurement module 108 and a RIO carrier 110D, also referred to as a generalized carrier 110D. As mentioned above, a generalized carrier with multiple cartridge slots may be configured with multiple interfaces for inserted cartridges, such that each cartridge's interface is implemented by the carrier. For example, if three cartridges with three different respective interfaces are inserted in three slots of the RIO carrier 110D, then the RIO carrier 110D may be configured to implement the three interfaces. Similarly, if multiple cartridges are sequentially inserted into and removed from a particular slot, the RIO carrier 110D may be configured respectively for each cartridge, i.e., sequentially. The RIO carrier 110D may further be operable to couple to any of various products or platforms.

In one embodiment, a channel or bus may be provided by the generalized carrier 110D for each cartridge/interface protocol. In other words, each slot may have an associated dedicated bus for that slot, with a corresponding portion of the generalized carrier's reconfigurable hardware configurable to implement the interface for a cartridge inserted into the slot. In another embodiment, the generalized carrier 110D may include a shared bus or backplane common to a plurality of the slots, where inserted cartridges may communicate through the common bus or backplane with the reconfigurable hardware of the generalized carrier in accordance with the respective interface protocols implemented on the reconfigurable hardware.

As mentioned above, in another embodiment, the generalized carrier may be configurable to include not only the adaptive interface functionality described above, but may also include or may be configured to include, one or more measurement and/or control functions.

As FIG. 11A shows, the measurement system may include measurement module 108, similar to that described above with reference to FIGS. 5A-5C. The measurement module 108 may couple to the generalized carrier 710 through one or more communication lines or terminals, as shown. The generalized carrier 110D may in turn be operable to couple to any of various products or platforms 720, as indicated.

In one embodiment, the measurement module 108 may include connectors 301 for (analog) signal I/O, i.e., for communicating with a sensor or actuator 112. As shown, the connectors 301 may couple to signal conditioning circuitry 302, which in this embodiment includes a signal conditioner and a MUX. The signal conditioning circuitry 302 may couple to signal conversion circuitry, such as the ADC 304 shown, which may in turn couple to isolation circuitry 305, described above with reference to FIG. 5C. In this embodiment, the measurement module 108 also includes an EEPROM 106A containing the EDS which may be operable to communicate the interface protocol information to the carrier 110D, as also described above. Thus, the measurement module 108 may provide a physical connection between the sensor or actuator 112 and the carrier 110D, as well as signal conditioning, digitization, and isolation functions for the measurement system. In addition, in one embodiment, the measurement module 108 may provide identification (for Plug-and-Play (PnP)) and/or digital I/O (parallel and/or serialized) functionality. For example, the measurement module or cartridge may be, or function as, a communication cartridge, e.g., an RS232 or RS485 cartridge.

As indicated in FIG. 11A, the generalized carrier 110D may include functional unit 106, here shown as FPGA 308, which may be programmable to implement the interface specified by the measurement module 108, as described in detail above. In this embodiment, the generalized carrier 110D may also include a register set 712, through which communication with the products/platforms may be effected. In various embodiments, the generalized carrier 110D may provide additional functions which may include I/O scanning, timing and triggering, power-on states, logic, digital I/O timing/counting, data transfer and support for parallel and scanned backplanes, among others.

In the RIO system, the FPGA 308 may be configurable with a measurement or control function, including, but not limited to, timing, triggering, synchronization, signal processing, and analysis. Thus the FPGA 308 may perform a measurement/control function instead of, or in addition to, the computer system 102.

The products and platforms 720 indicated in FIG. 11A may provide means for the carrier 110D to communicate with external systems. For example, an Application Programming Interface (API) 722 may allow external systems to read and/or write to the registers in the register set 712 to communicate and/or control the measurement system. For another example, a processor, e.g., a micro-controller 724, and a network interface card 726 may couple the registers to a network 104, through which communications with external systems may be facilitated. In one embodiment, the products and platforms 720 may be comprised in the carrier 110D, while in other embodiments the products and platforms 720 may be external to the carrier 110D, e.g., may be comprised in computer system 102.

Figure 11B:
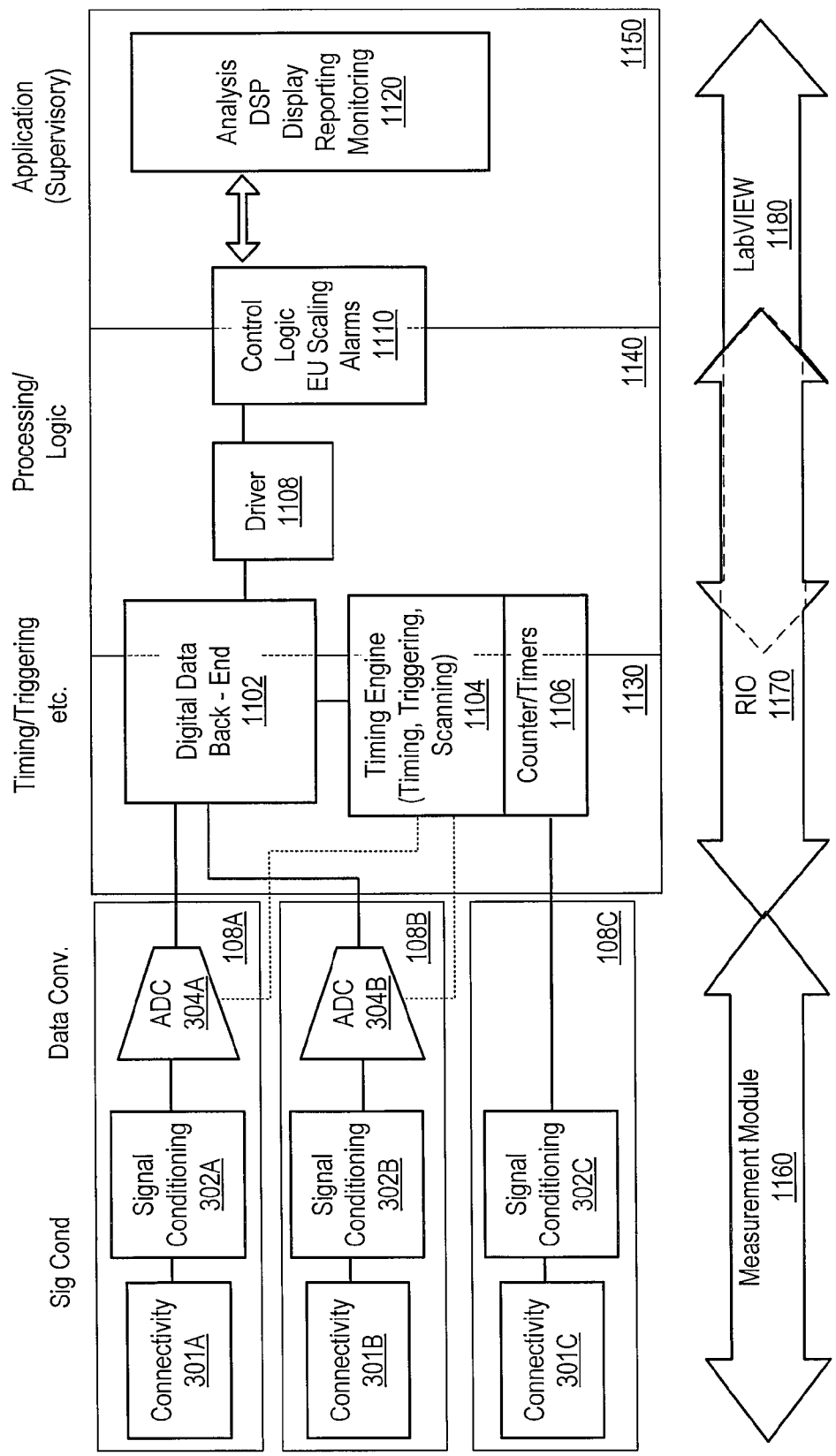
FIG. 11B is a block diagram illustrating functional partitions of a RIO measurement system with measurement modules, according to one embodiment.

FIG. 11B—Measurement System Partitioning

FIG. 11B is a block diagram illustrating functional partitioning among components of a RIO-based measurement system with a plurality of measurement modules. More specifically, FIG. 11B shows the partitioning of functionality between domains of the application (e.g., LabVIEW) 1180, RIO 1170, and the measurement modules 1160.

As FIG. 11B shows, the measurement module domain 1160 may be responsible for signal input via module connectivity 301, as well as signal conditioning 302, and data conversion, via converters such as ADCs 304A and 304B comprised in the measurement modules 108. As FIG. 11B also shows, timing and triggering 1130 may be handled in the RIO domain 1170, for example, by a digital data back-end 1102, timing engine 1104, and one or more counter/timers 1106, all comprised in the RIO carrier 110. Processing/Logic operations 1140 of the measurement system may be provided by driver 1108 and control logic, EU scaling, and alarms 1110, and may also utilize the digital data back-end 1102, timing engine 1104, and one or more counter/timers 1106 to some extent, as shown. Is should be noted that the processing/logic capabilities 1140 of the system may be shared by the RIO 1170 and the application, i.e., LabVIEW 1180, as indicated by the overlap between the RIO domain 1170 and the LabVIEW domain 1180. Finally, analysis, DSP, display, reporting, and monitoring capabilities 1120 may be provided by the application 1150 (functioning in a supervisory capacity), i.e., in the LabVIEW domain 1180. It is further noted that this supervisory capacity may in part involve use of the control logic, EU scaling, and alarms 1110, as shown.

Thus, in one embodiment, the various functionalities of the measurement system may be partitioned among the measurement module domain 1160, the RIO domain 1170, and the application (LabVIEW) domain 1180.

Figure 12A:
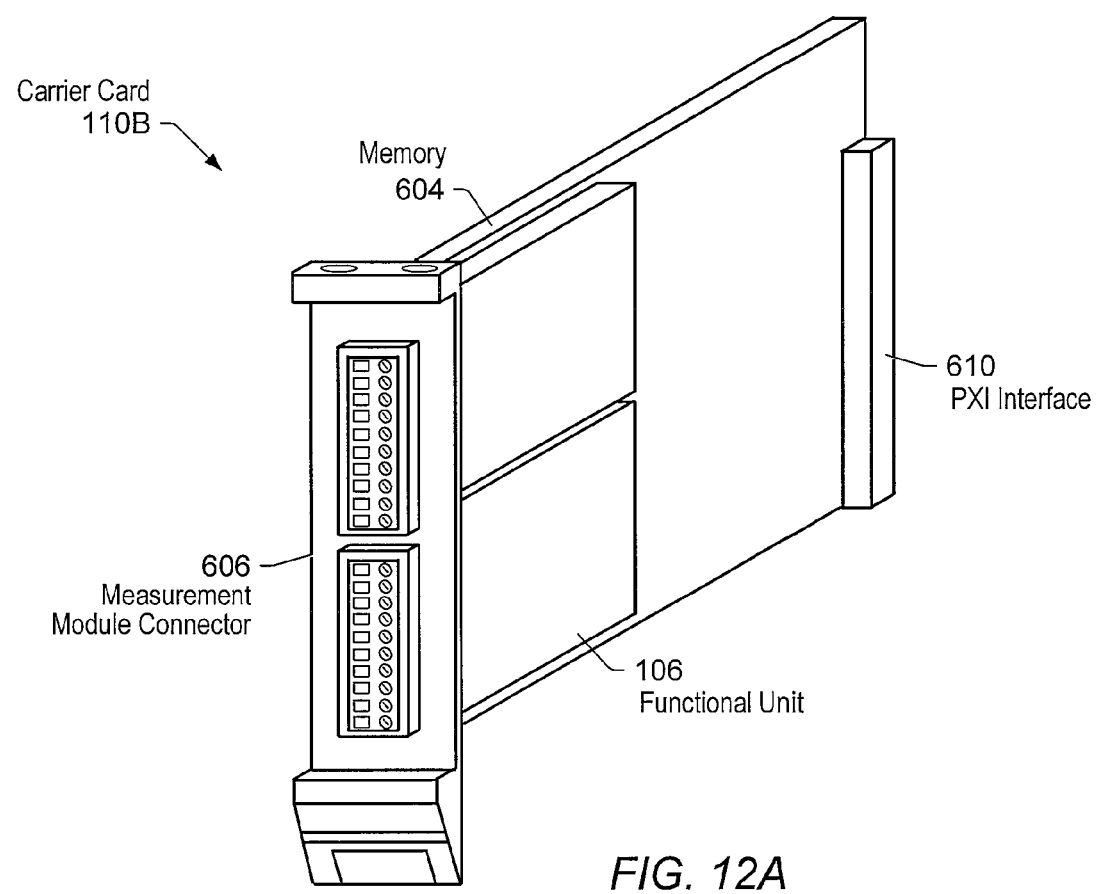
FIG. 12A illustrates a PXI carrier card, according to one embodiment of the invention.

FIG. 12A—PXI Card Based Carrier

FIG. 12A illustrates a carrier 110B comprising a PXI card, i.e., implemented on a PXI card, according to one embodiment of the invention. The PXI card 110B may be operable to plug into a PXI chassis or a suitably equipped computer system 102, and may implement the carrier functionality described above, i.e., the PXI card 110B may include (in addition to PXI interface circuitry 610) a functional unit 106 which is programmable or configurable to implement an interface based on interface protocol information transmitted from a coupled measurement module 108, as described above. As also described above, the carrier 110B (PXI card) may be operable to couple to (or be comprised in) computer system 102 to facilitate the described programming by the computer system 102. Alternatively, the PXI card may include computer system 102, e.g., may include a processor and memory in the form of a "PC on a card". It should be noted that other card based implementations besides the PXI card implementation are also contemplated, for example, PCI, Infiniband, or other protocols or platforms may be used to implement a carrier, the PXI card embodiment being but one example.

As FIG. 12A shows, in one embodiment, the PXI card 110B may include a memory 604 coupled to the functional unit where configuration information or program instructions may be stored for deployment or execution on or by the functional unit 106. The PXI card may also include at least one measurement module connector 606 whereby a measurement module 108 may be attached or coupled to the PXI card, and which facilitates communication between the PXI card 110B and the measurement module 108.

In one embodiment, implementing the carrier in a PXI board 110B (or other card implementation) may provide integrated signal conditioning, modularity, and an interface to plug and play sensors. Additionally, in some embodiments, these features may be provided at a lower cost than prior art systems.

Figure 12B:
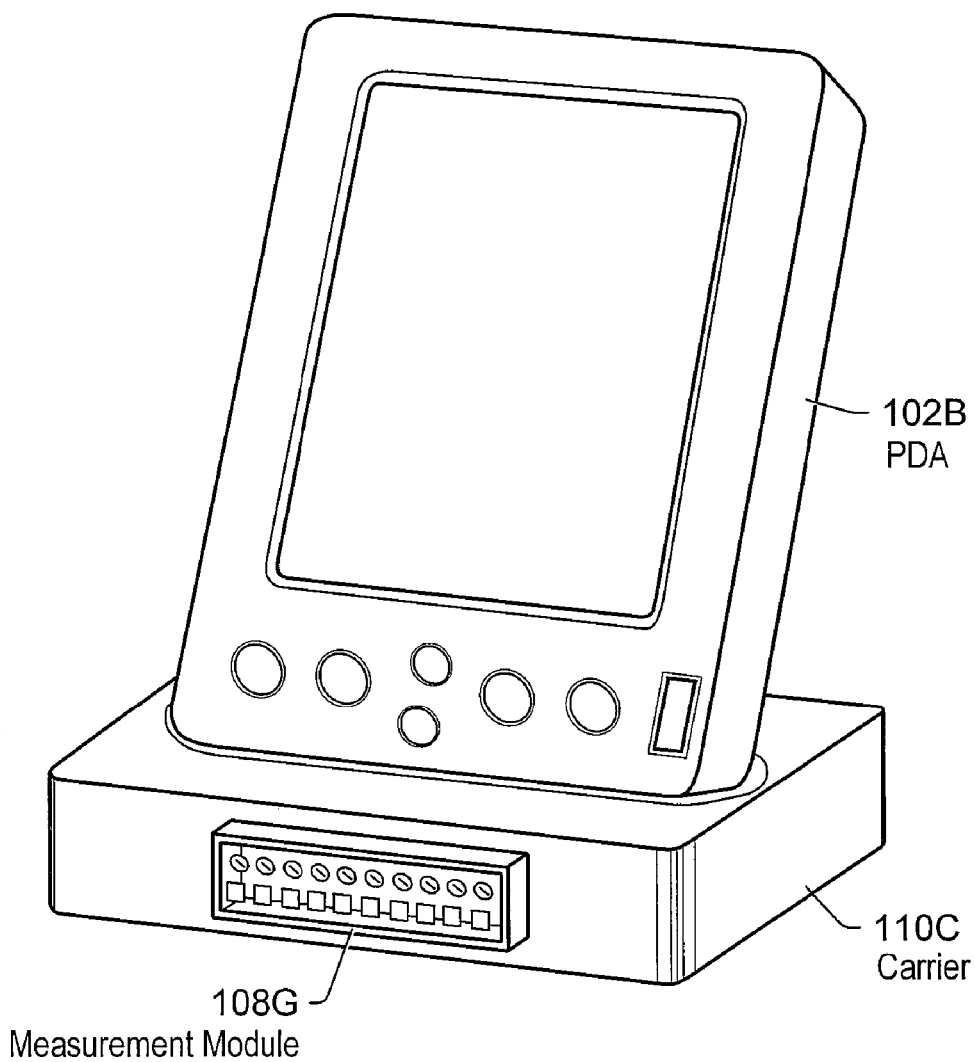
FIG. 12B illustrates a PDA based measurement system, according to one embodiment of the invention.

FIG. 12B—PDA with Carrier and Measurement Module

FIG. 12B illustrates another embodiment of a carrier unit 110 and measurement module 108. As FIG. 12B shows, in one embodiment, the carrier unit 110 may comprise or be coupled to a Personal Digital Assistant (PDA). In the embodiment shown, PDA 102B is operable to couple to carrier 110C, which may be implemented as an adaptor which is operable to couple to the PDA 102B through a standard communication or expansion port on the PDA 102B. In another embodiment, the carrier 110C may be comprised in the PDA 102B, i.e., may not be a detachable module. For example, the PDA 102B may itself be the carrier.

The carrier 110C may be operable to couple to a measurement module 108G, as shown. The measurement module 108G may in turn be operable to couple to a sensor or actuator 112, as described above. In one embodiment, PDA 102B may be operable to program the carrier 110C (i.e., the carrier unit's functional unit) with the interface protocol information provided by the measurement module 108G, as described in detail above. Alternatively, the PDA 102B may be programmed as the carrier unit. In one embodiment, the PDA 102B may be further operable to provide functionality related to a measurement, DAQ, and/or control task or operation. In other words, in addition to acting as a development platform for the carrier 110C/measurement module 108G, the PDA 102B may also operate in a measurement and/or control capacity in conjunction with the carrier 110C and measurement module 108G. In another embodiment, the PDA 102B may be used as an interface to another computer system, e.g., computer system 102. For example, a suitably equipped PDA 102B may provide wireless communication for the carrier 110C/measurement module 108G.

Figure 12C:
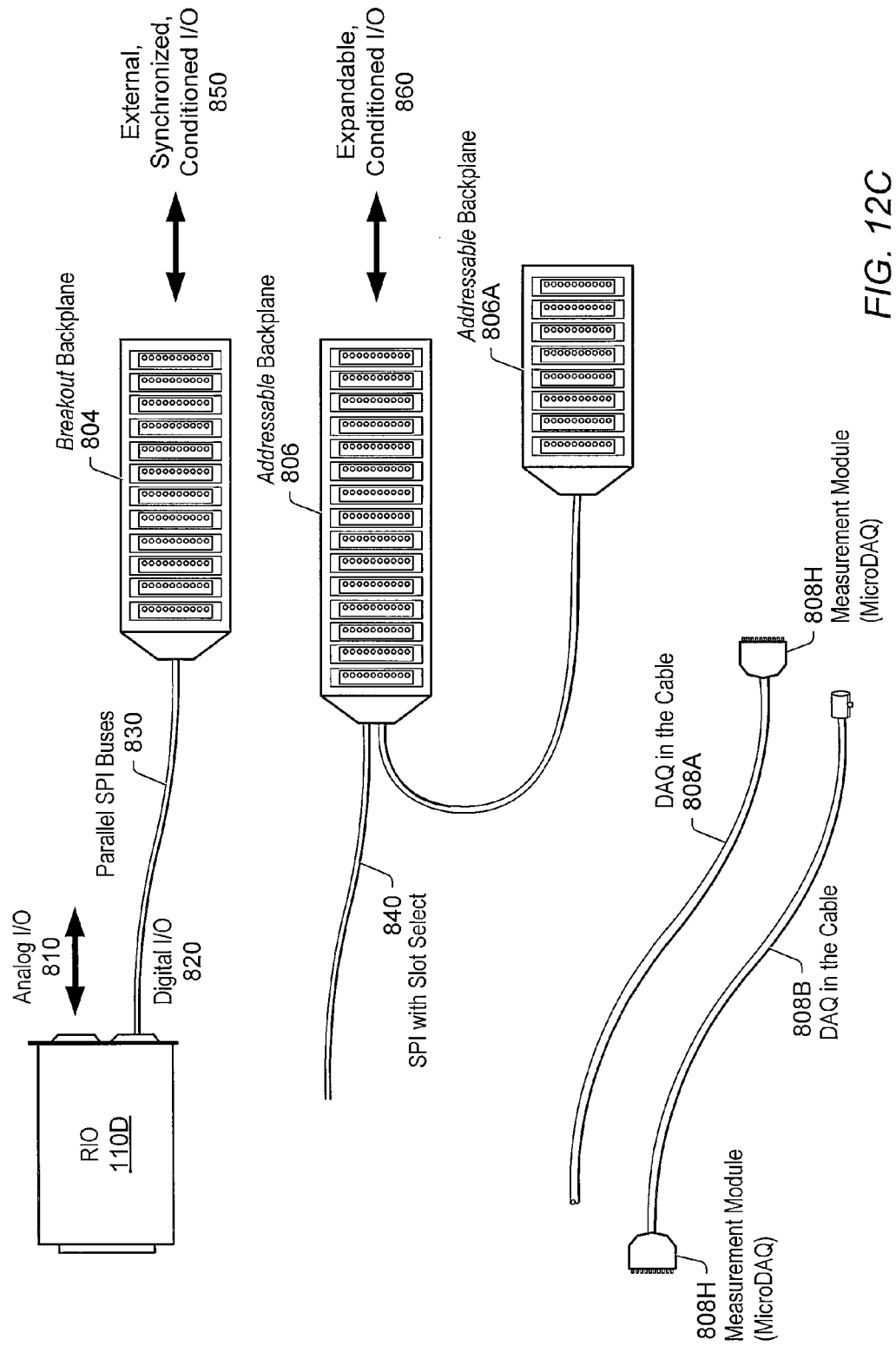
FIG. 12C illustrates various embodiments of a RIO based system with I/O expansion.

FIG. 12C—RIO System with External I/O Expansion

FIG. 12C illustrates several embodiments of the invention using RIO 110D (generalized carrier 110D, described above with reference to FIG. 7) with external I/O expansion, i.e., with additional I/O connections for coupling to a plurality of measurement modules 108. As FIG. 12C shows, a RIO cartridge or card 10D may provide connectors for analog I/O 810 and/or digital I/O 820. As may be seen, without the use of expansion I/O devices, the number of measurement modules 108 which may be coupled to the RIO card 110D may be limited, e.g., to one.

In one embodiment, the digital I/O 820 may couple to a breakout backplane 804, for example, via parallel SPI buses 830, as shown, although other buses for coupling the I/O expansion devices to the carrier 110D are also contemplated. The breakout blackplane 804 may provide connectivity for a plurality of measurement module cards or cartridges 108, and may thereby be operable to facilitate external, synchronized, and conditioned I/O 850 for the measurement system. For example, each measurement module or cartridge 108 comprised in or on the breakout backplane 804 may be operable to couple to a sensor or actuator 112. Each measurement module 108 may also couple to the backplane 804. The breakout backplane 804 may then facilitate synchronization between the various measurement modules 108. Additionally, as described above, the measurement modules 108 may provide any of a variety of DAQ, measurement, and control functions, including signal conditioning and conversion, and thus external, synchronized, and conditioned I/O 850 capabilities may be included in this embodiment of the invention.

In another embodiment, the RIO card or device 110D may couple to an addressable backplane 806, for example, through an SPI with slot select capabilities 840. In other words, the addressable backplane 806 may provide a plurality of individually addressable slots for a plurality of measurement modules or cartridges 108, described above, which may each be individually targeted for communication by the carrier 110D. Additionally, the addressable backplane 806 may be expandable, i.e., additional addressable backplanes 806A may be coupled to the addressable backplane 806 to provide additional slots for additional measurement modules 108. Thus, in this embodiment, expandable, conditioned I/O capabilities 860 may be provided by the system.

In yet another embodiment, the RIO card or device 110D may couple to a "DAQ in the cable" 808, where a measurement module 108H may be comprised in a cable connector. In other words, the features of a measurement module 108, as described above, may be included in one or both connectors of a cable, as shown. For example, in the example of DAQ in cable 808A, one end of the cable may be coupled to the RIO device 110D, and the measurement module/connector 108H may be operable to couple to a sensor or actuator 112. In another example, the DAQ in cable 808B may comprise measurement module 108H which may be operable to couple to the RIO card 110D, and another cable connector (without a measurement module 108H) for coupling to a sensor/actuator 112.

Thus, in various embodiments, the functionality of one or more measurement modules 108 may be provided through the use of I/O expansion devices (e.g., devices 804, 806, and 808) which may extend the I/O capabilities of the carrier 110, or RIO device 110D. Furthermore, in some embodiments, additional functionality may be provided by the expansion device, such as the ability to synchronize the I/O.

Figure 12D:
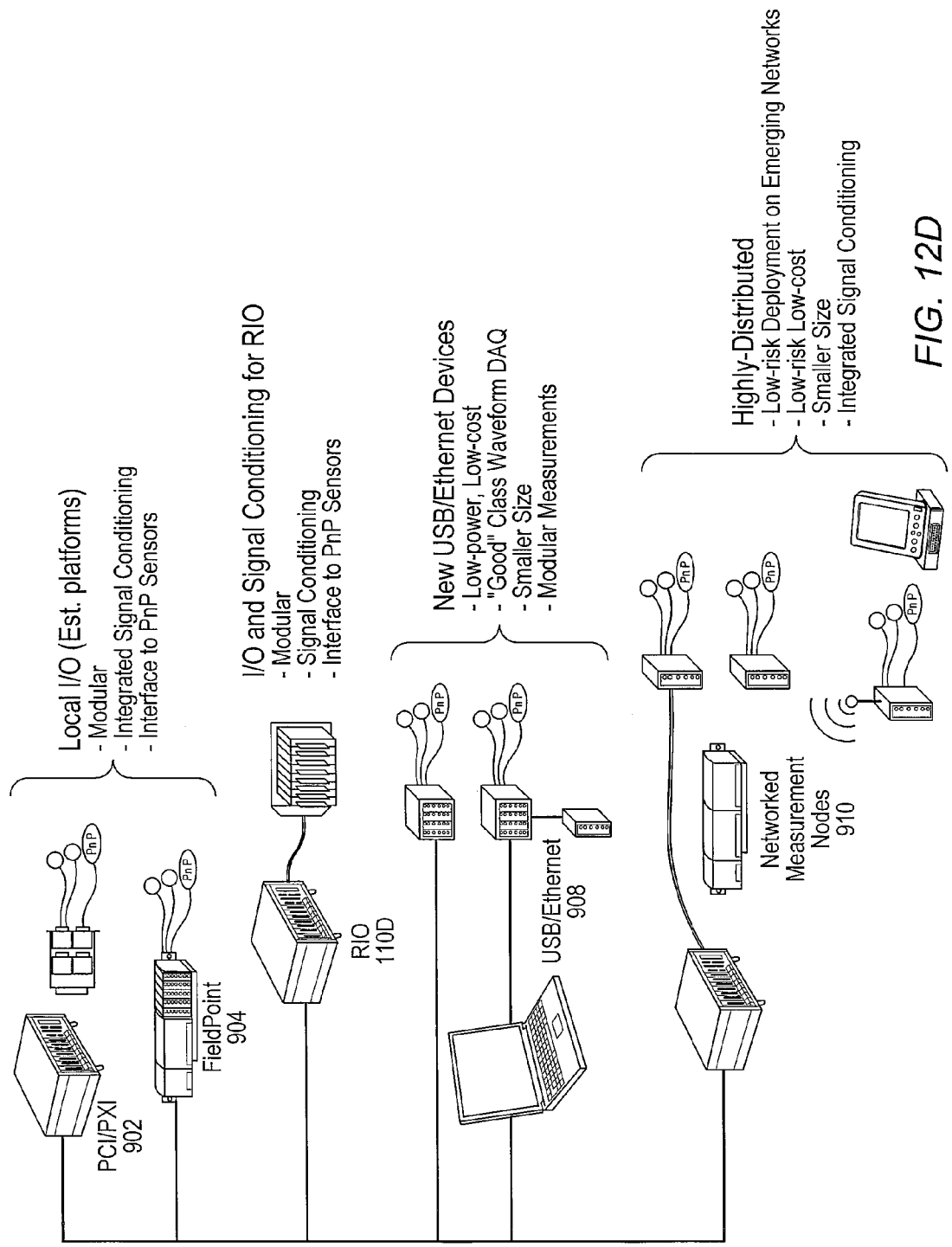
FIG. 12D illustrates various sensor/measurement systems according to the present invention.

FIG. 12D—Measurement System Platform Extensions

FIG. 12D illustrates various embodiments of the measurement system using a variety of the platform extension technologies described above. It should be noted that the system extensions shown are meant to be exemplary, and are not intended to limit the type of extensions/devices used in the measurement system.

As FIG. 12D shows, in one embodiment, the system may include a PCI or PXI chassis 902 (cartridge carrier 110A) with measurement cartridges 108D, as described above with reference to FIGS. 5-12A. Note that other buses/chassis besides PCI and PXI may also be used. For example, a FieldPoint system 904 (from National Instruments) may provide the chassis, slots, and backplane to accommodate the plurality of measurement cartridges 108D. As shown, one or more of the measurement cards or cartridges 108 may couple to one or more sensors or actuators 112, which may include one or more Plug and Play (PnP) sensors. Thus these embodiments may provide local I/O using established platforms (PCI, PXI, FieldPoint, etc.) and integrated signal conditioning, as well as interfaces to PnP sensors, as shown.

In another embodiment, a generalized carrier, i.e., a RIO device 110D as described above with reference to FIGS. 11 and 12C, may provide modular I/O and signal conditioning, and may also provide an interface to PnP sensors, as well as regular sensors and actuators 112. It is noted that a RIO system may be implemented in any of the systems shown in FIG. 12D.

In another embodiment, USB/Ethernet devices 908 may be used to provide low-power, low-cost measurement systems, where USB/Ethernet communication functions may be provided by an expansion card on a personal computer (e.g., a laptop, or PDA), or by an inexpensive controller which may be comprised in another device. For example, such systems may include "good" class waveform data acquisition capabilities, have a small form factor, i.e., a small size, and may also provide for modular measurements through the use of small detachable measurement modules 108, as described above. Thus, a plurality of sensors 112, possibly including PnP sensors, may be fielded using USB/Ethernet (or other buses/transmission media) in an affordable manner.

In yet another embodiment, highly distributed measurement systems based on networked measurement nodes 910 may be developed using PXI or FieldPoint (or any other suitable platform) and a plurality of distributed carriers 110 and/or measurement modules 108. In one embodiment, measurement systems may be distributed over a wide area network, such as the Internet. Such systems may provide integrated signal conditioning using small inexpensive components (carriers 110, measurement modules 108, and/or sensors 112), such as PDAs, wireless smart sensors, linked modular measurement devices, etc., thereby providing a low-risk, low-cost measurement solution. For example, the system may be suitable for low-risk deployment on emerging networks.

Thus, the use of measurement modules 108 in combination with a variety of carrier units 110 and computer systems 102 provides a broad range of approaches for efficient and affordable measurement systems, including established platforms such as PCI/PXI 902 and FieldPoint 904, generalized carriers 110D such as RIO, new USB/Ethernet devices 908, and small networked measurement nodes 910.

Figure 13:
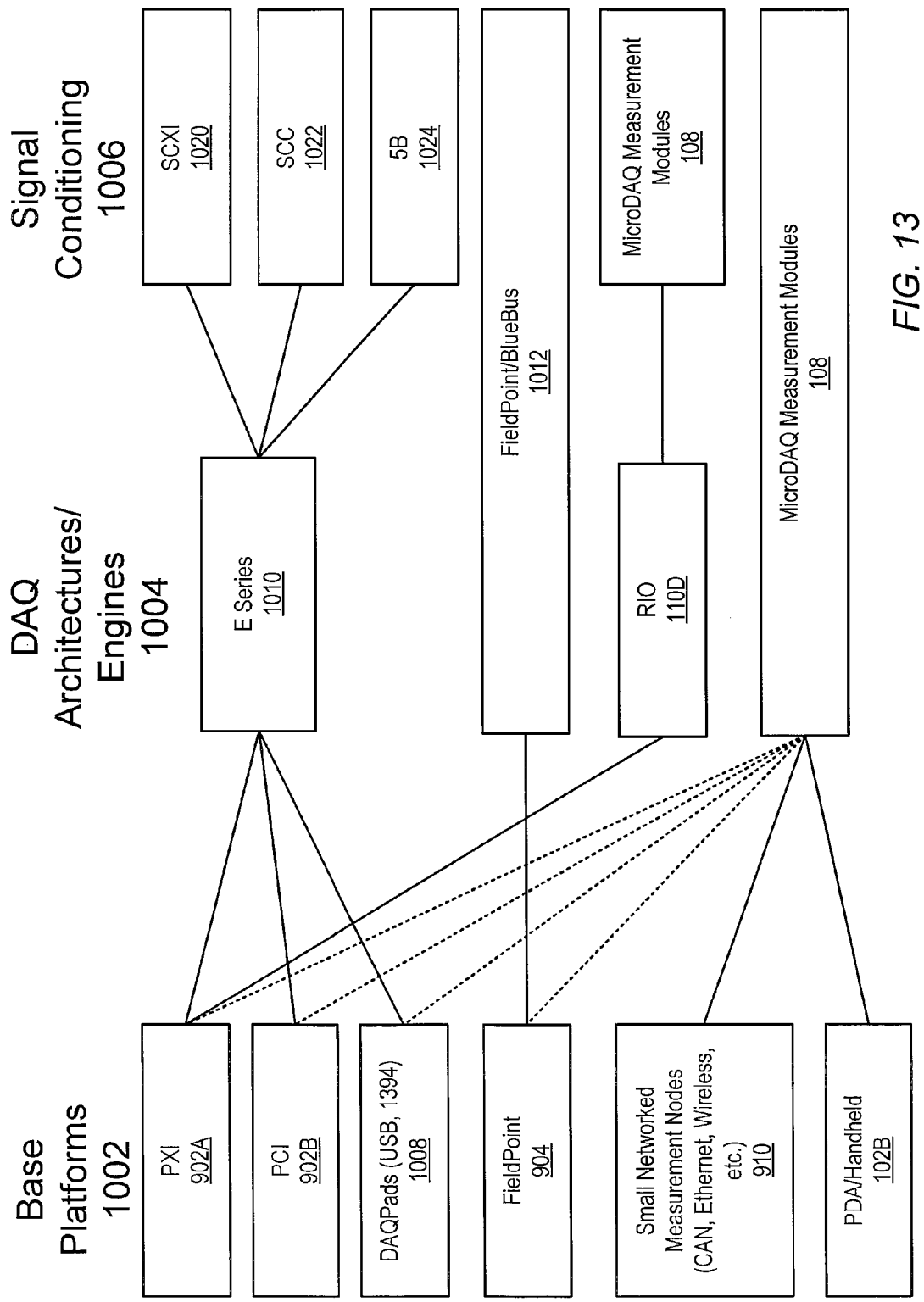
FIG. 13 illustrates the use of measurement modules in the context of current measurement systems.

FIG. 13—Platforms and Technology

FIG. 13 illustrates embodiments of the present invention in the context of current art with respect to platforms, DAQ architectures/engines, and signal conditioning. As FIG. 13 shows, a plethora of different measurement, DAQ, and/or control systems may be developed using various combinations of base platforms 1002, DAQ architectures/engines 1004, and signal conditioning devices or systems 1006.

For example, any of a number of base platforms 1002 may be used to provide a connectivity infrastructure for the system, including, but not limited to, PXI 902A, PCI 902B, DAQPads 1008 (from National Instruments) which may utilize USB, 1394, etc., FieldPoint 904, small networked measurement nodes 910, and PDAs/handheld computers 102B.

DAQ architectures/engines 1004 which may be selected include, but are not limited to, the National Instruments E Series of DAQ devices 1010, FieldPoint/BlueBus 1012, RIO 110D, and small form-factor measurement modules 108.

Signal conditioning technologies 1006 which may be used in such systems include (but are not limited to) SCXI 1020, SCC 1022, and 5B 1024 signal conditioners, as well as FieldPoint/BlueBus compliant signal conditioners, and measurement modules 108, such as National Instruments small form-factor measurement modules.

As FIG. 13 indicates, components or standards may be selected from each class of component (platforms 1002, engines 1004, signal conditioners 1006), and, depending on compatibility, combined to develop a wide variety of measurement systems. For example, a PXI platform 902A may be combined with E Series devices 1010, RIO 110D, and measurement modules 108, while a PCI platform 902B may be combined with E Series devices 1010 and measurement modules 108, but not RIO 110D.

More generally, PXI 902A, PCI 902B, and DAQPads 1008 platforms may be combined with E Series instruments 1010, and, along with FieldPoint 904 platforms, may also be combined with measurement modules 108. The FieldPoint platforms 904 may also be combined with the FieldPoint/BlueBus architecture/engine and signal conditioning devices 1012. Small networked measurement nodes platforms 910 (including CAN, Ethernet, wireless media, etc.) and PDA/handheld computers 102B may be combinable with the measurement modules 108, as described above, for DAQ engine functionality 1004 and signal conditioning 1006.

As FIG. 13 also shows, the E Series devices/engines 1010 may be combinable with SCXI 1020, SCC 1022, and 5B 1024 signal conditioners, while the RIO engine 110D may be combinable with the measurement modules 108.

Thus, the use of measurement modules 108 and various carrier units 110 may provide complementary and overlapping functionality as compared to current approaches to development of measurement systems, and may also provide substantial cost, efficiency, and flexibility benefits, as described in detail above. In particular, the use of the measurement modules 108 with carriers 110 leverages disruptive semiconductor technology to deliver highly modular DAQ/Signal Conditioning/Conversion functionality which is reusable in many platforms, e.g., USB, Ethernet, FieldPoint, RIO, PDAs, etc., and which lowers risk and effort in supporting new platforms, such as wireless, CAN, etc. In one embodiment, this technology is generally capable of providing "good" class DAQ, e.g., up to ~50 kSamples/s, although it is also contemplated that as the performance of hardware improves, higher performance DAQ may also be possible using the present invention.

Figure 14:
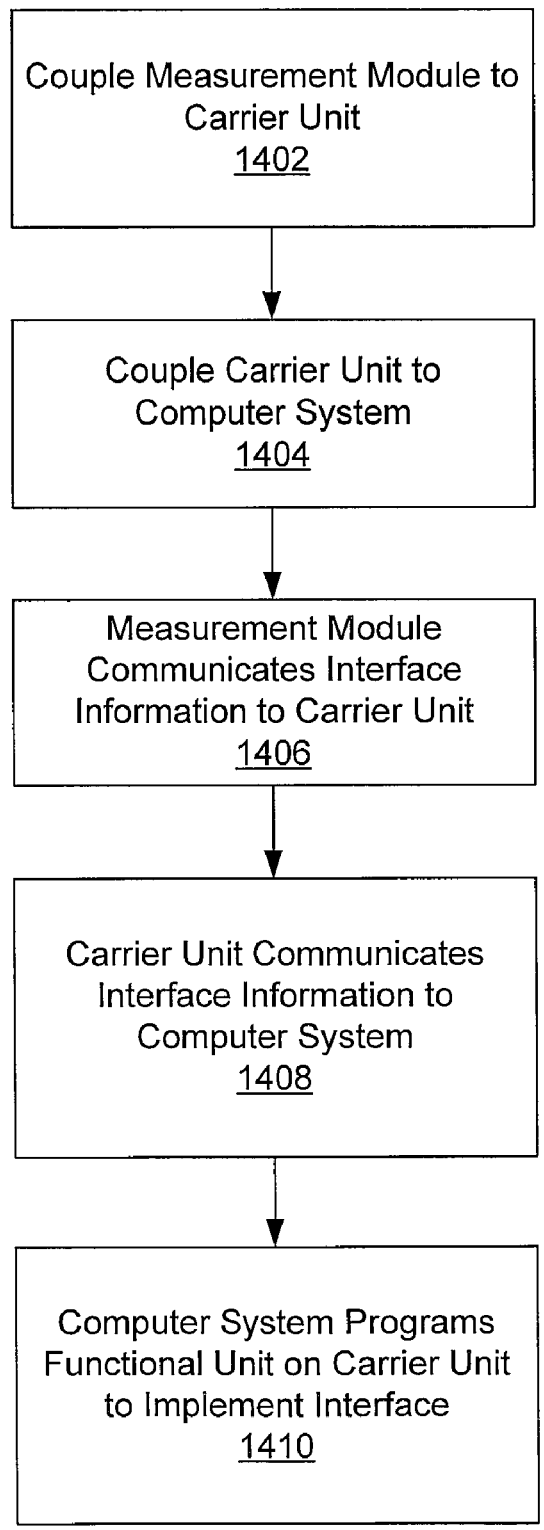
FIG. 14 is a flowchart of a method for configuring a measurement system, according to one embodiment.

FIG. 14—Method for Configuring a Measurement System

FIG. 14 is a flowchart of a method for configuring a measurement system, according to one embodiment of the invention. It should be noted that in some embodiments, various of the steps may occur concurrently, in a different order than shown, or may be omitted. Furthermore, one or more additional steps may be performed as desired.

As FIG. 14 shows, in 1402 a measurement module 108 may be coupled to a carrier unit 110. For example, the measurement module 108 may be coupled to the carrier unit 110 via a serial bus, a parallel bus, wireless transmission medium, a network, or edge connection or any other communication medium. In a typical embodiment, the measurement module 108 is a card or cartridge that can be inserted into a slot of the carrier unit 110. In this embodiment, the carrier unit 110 may comprise a plurality of slots adjusted to receive different measurement modules 108.

In 1404, the carrier unit 110 may be coupled to a computer system 102. In one embodiment, the carrier unit 110 may be coupled to the computer system 102 via a serial bus such as an SPI cable. In other embodiments, the carrier unit 110 may be coupled to the computer system 102 through various communication media, including, but not limited to, a serial bus, a parallel bus, wireless transmission medium, a network, such as the Internet, or any other communication medium. In another embodiment, the carrier unit 160 may include computer system functionality, e.g., the carrier unit 110 may include a processor, micro-controller, or a "computer on a card" that performs a desired processing function. In this embodiment, step 1404 (and 1408 below) may be unnecessary.

In 1406 the measurement module 108 may communicate interface information to the carrier unit 110, where the interface information specifies an interface for operating with the measurement module 108. For example, as noted above, in one embodiment, the interface information may be in the form of an EDS (Electronic Data Sheet) structure. In another embodiment, the interface information may simply be identification information, e.g., a module ID, which may then be used to retrieve the interface protocol for the module.

In 1408, the carrier unit 110 may communicate the interface information to the computer system 102. It is noted that steps 1406 and 1408 may be performed as one step when measurement module communicates the interface information directly to the computer system 102.

Finally, in 1410, the computer system 102 may use the interface information to program a functional unit 106 on the carrier unit 110, thereby implementing the specified interface in the carrier unit 110. For example, in an embodiment where the interface information includes the interface protocol for the module 108, the computer 102 may program the carrier unit 110 with the interface information. Alternatively, in an embodiment where the interface information comprises a module ID, the computer 102 may use the module ID to retrieve or select an appropriate interface protocol, such as from a memory medium of the computer system 102 or from a server 102A coupled to the computer system 102, and program the carrier with the interface protocol, e.g., with a bitstream implementing the interface protocol. After the carrier unit 110 has been programmed, the carrier unit 110 and the measurement module 108 may be together operable to perform one or more of a data acquisition, measurement, and control task or function.

It is noted that in an embodiment in which the carrier 110 includes a processor and memory, i.e., includes the computer 102, steps 1404 and 1408 may be omitted, and thus, in 1410, the processor and memory on the carrier 110 may program the functional unit of the carrier 110 with the communicated interface protocol.

In one embodiment, the method may further include the carrier unit 110 and the measurement module 108 together performing the task or function.

Figure 15:
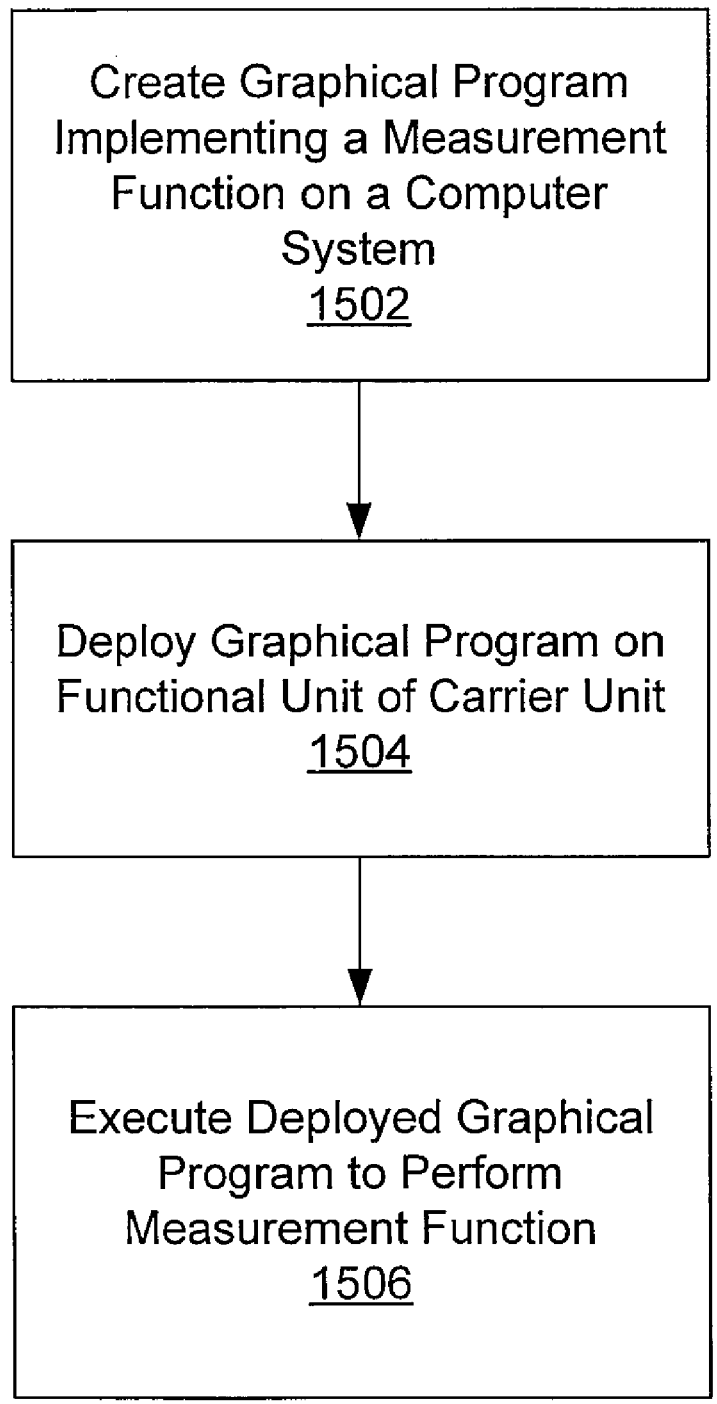
FIG. 15 is a flowchart of another method for configuring a measurement system, according to one embodiment.

FIG. 15—Another Method for Configuring a Measurement System

FIG. 15 is a flowchart of another method for configuring a measurement system comprising a computer system 102 coupled to or comprising a measurement device. The measurement device may comprise a carrier unit 110 and one or more measurement modules 108. The carrier unit 110 preferably includes a functional unit 106, as described above. As mentioned previously, in some embodiments, various of the steps may occur concurrently, in a different order than shown, or may be omitted. Furthermore, one or more additional steps may be performed as desired.

As shown in FIG. 15, in 1502, a program may be created on the computer system 102 which implements a measurement function. As mentioned above, a measurement function may include any of a measurement (including data acquisition) or control task or function. It should be noted that in a preferred embodiment, the program may comprise a graphical program, i.e., the program may comprise a plurality of interconnected nodes which visually indicate functionality of the graphical program, such as a LabVIEW VI. However, in other embodiments, the program may be implemented in any other programming language or system, including C, C++, Java, and Visual Basic, among others. In one embodiment, the program may be programmatically created in response to user input received to a wizard-like interface, as described in U.S. patent application Ser. No. 09/745,023 titled "System and Method for Programmatically Generating a Graphical Program in Response to Program Information," filed Dec. 20, 2000, which was incorporated by reference above.

In 1504, the (graphical) program may be deployed on the functional unit of the device, i.e., of the carrier, where after the deployment of the program the functional unit implements the measurement function of the program. In other words, the functional unit is operable to perform the measurement function encoded in the program. As mentioned above, the measurement function may include one or more of data acquisition, measurement, and control functions, as desired.

In an embodiment where the functional unit on the device is a processor, deploying the program on the functional unit of the device may include transferring the program to a memory on the device (i.e., carrier 110) for execution by the processor. In one embodiment, this may include transferring the program in its native format to the memory and the processor executing the program, e.g., using a graphical program execution engine and possibly a RTOS (real time operating system). Alternatively, the program may be compiled into an executable program (e.g., machine language, a script, or an interpretable data structure) and transferred to the memory for execution by processor.

In an embodiment where the functional unit on the device is a programmable hardware element, e.g., an FPGA, deploying the program on the functional unit of the device may include converting the program into a hardware description, such as a VHDL file, which may be compiled and used to program the FPGA to perform the measurement function. For example, the hardware description may be converted into an FPGA-specific netlist which describes the components required to be present in the hardware as well as their interconnections. Conversion of the hardware description into the FPGA-specific netlist may be performed by any of various types of commercially available synthesis tools, such as those available from Xilinx, Altera, etc. The netlist may be compiled into an FPGA program file, also referred to as a software bit stream or hardware configuration program, which can be readily downloaded to program the FPGA. After the netlist has been compiled into an FPGA program file the FPGA program file may be transferred to the FPGA, thereby producing a programmed hardware equivalent to the program.

In 1506, the functional unit, i.e., the carrier 110, may optionally execute the deployed program to perform the measurement function. Said another way, the measurement system may perform the measurement function via execution of the program by the functional unit on the device, i.e., the carrier 110.

Figure 16:
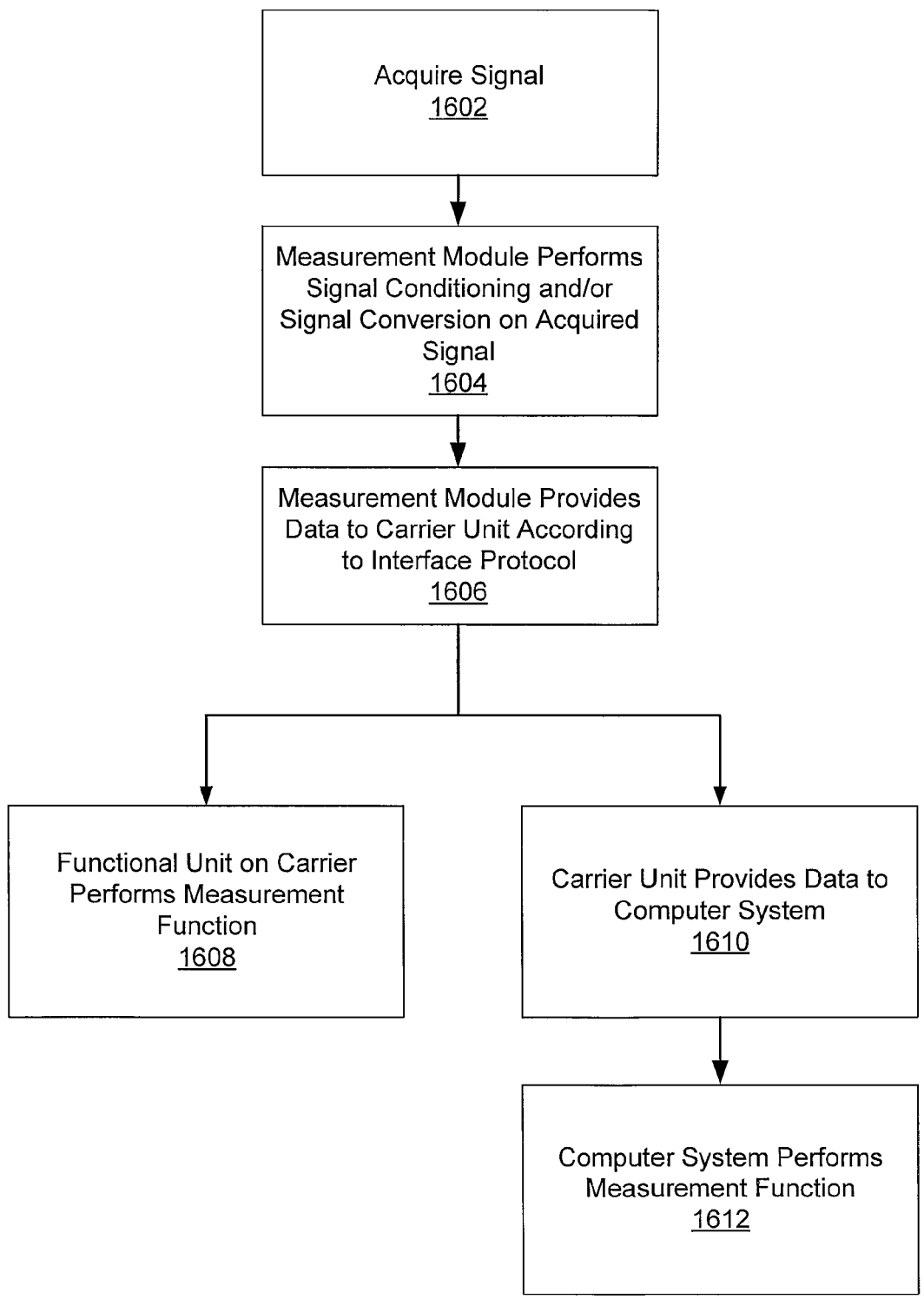
FIG. 16 is a flowchart of a method for performing a measurement function, according to one embodiment.

FIG. 16—Method for Performing a Measurement Function

FIG. 16 is a flowchart of a method for performing a measurement function, according to one embodiment of the present invention. As noted above, in some embodiments, various of the steps may occur concurrently, in a different order than shown, or may be omitted. Furthermore, one or more additional steps may be performed as desired.

In 1602, a signal may be acquired. For example, a measurement module coupled to or comprised in a carrier unit may acquire the signal. The signal may originate from a sensor or actuator 112, or may be transmitted from an external system.

In 1604, the measurement module 108 may perform one or more of signal conditioning and signal conversion on the acquired signal, as described in more detail above. For example, the measurement module may perform filtering, gain adjustments, ADC or DAC, etc. on the signal. In performing the signal conditioning and/or signal conversion on the acquired signal, the measurement module 108 may generate data, e.g., results data, which may include one or more of the original signal, the conditioned and/or converted signal, or information derived from or generated in response to the signal.

In 1606, the measurement module 108 may provide the data to the carrier unit 110 according to an interface protocol, e.g., the interface protocol described above.

Then, in an embodiment where a functional unit on the carrier 110 has been programmed or configured appropriately, in 1608, the functional unit on the carrier 110 may perform a measurement function, e.g., on the signal or data. In other words, the carrier 110 may perform a measurement function which was programmed into the functional unit. For example, the carrier 110 (i.e., the functional unit on the carrier 110) may perform any of various data processing operations on the data, such as filtering, analysis, digital signal processing, pattern recognition, or other analysis. For another example, the carrier may generate control signals in response to an analysis of the data, such as to control one or more plant or manufacturing operations.

In another embodiment in which the computer system 102 comprises measurement software for performing a measurement function, in response to 1606 above, the carrier unit 110 may provide the data to the computer system 102, as indicated in 1610. Then, in 1612, the computer system 102 may perform the measurement function, e.g., on the signal, where the measurement function may include data acquisition, measurement, and/or control functions, as described above. In another embodiment, the carrier unit 110 may perform a portion of the measurement analysis or control function and the computer system 102 may perform the remaining portion of the measurement analysis or control function.

Figure 17:
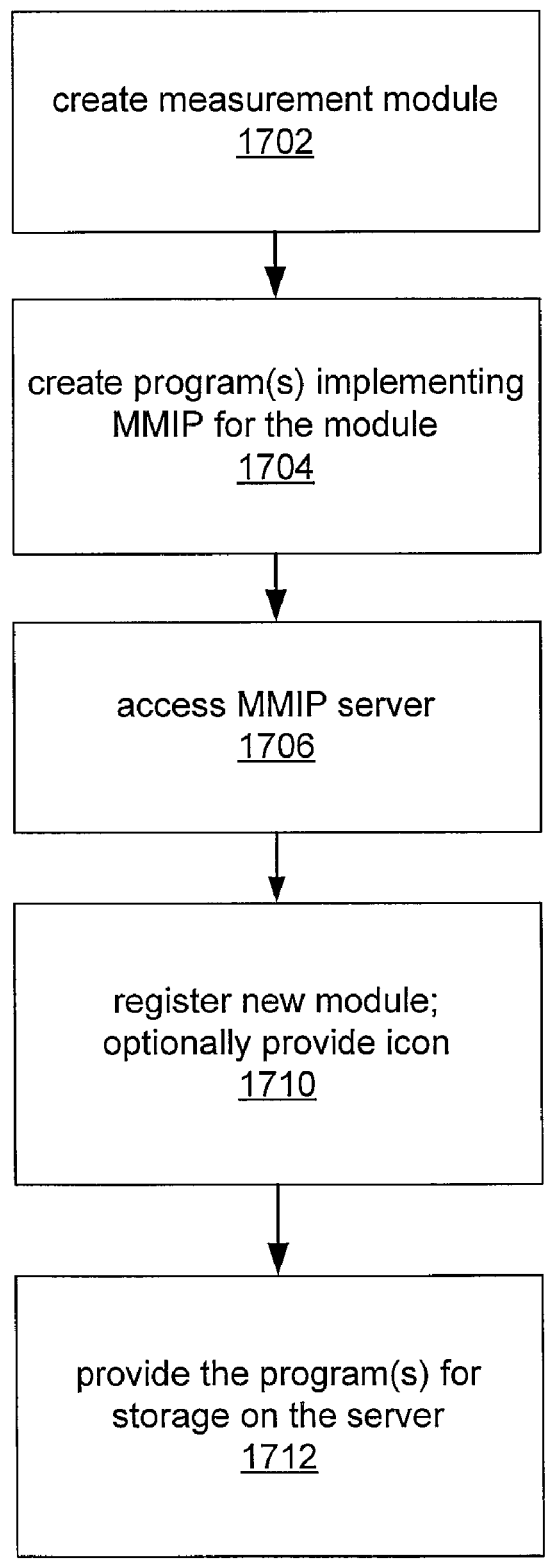
FIG. 17 is a flowchart of a method for registering a measurement cartridge bitstream with a measurement module interface protocol (MMIP) server.

FIG. 17—Method for Registering a Measurement Module Interface Protocol for a Measurement Module In one embodiment of the present invention, rather than the module or cartridge 108 providing the MMIP (measurement module interface protocol) to the carrier 110 (or computer 102), the MMIP for the cartridge may be stored on an MMIP server 102A, as described above with reference to FIG. 1B.

FIG. 17 is a flowchart of a method for registering an MMIP program for a measurement module with the MMIP server 102A, according to one embodiment of the present invention. As noted above, in some embodiments, various of the steps may occur concurrently, in a different order than shown, or may be omitted. One or more additional steps may also be performed as desired.

As FIG. 17 shows, in 1702, a measurement module 108 according to the present invention may be created, e.g., by a manufacturer. As described above, the measurement module 108 may include any of a wide variety of functions for use in a measurement system, including for example, signal conversion and signal conditioning, among others. The measurement module 108 may have associated with it an MMIP which codifies the communication interface for the module 108, as also described above.

Then, in 1704, a program may be created which implements the measurement module's MMIP. In one embodiment, a plurality of programs may be created for the module 108, where each program implements a different interface for the measurement module. In other words, each program may facilitate a different function set or communication interface for the module 108. As also described above, each program may be deployable on the carrier to configure the carrier to support or implement the corresponding MMIP. In an embodiment where the carrier's functional unit is a processor and memory, the program may be executable by the processor, thereby implementing the module's MMIP. In one embodiment, the program may comprise a graphical program, e.g., a LabVIEW graphical program. In another embodiment, the carrier's functional unit may comprise a programmable hardware element 106, such as an FPGA, in which case, the program may comprise a bitstream which is deployable on the FPGA to implement the MMIP. Thus, one or more programs may be created for the measurement module codifying a corresponding one or more measurement module interface protocols for respective functional configurations or versions of the measurement module.

In 1706, the MMIP server 102A may be accessed, for example, via a computer system operated by, or on behalf of, the manufacturer or a related entity, such as a wholesaler or retailer. In one embodiment, the MMIP server 102A may be accessed over a network, such as the Internet, although other methods of access may be used as well.

In 1710, the measurement module 108 may be registered with the MMIP server 102A. For example, identification information for the module 108, such as an ID or functional description, may be provided to the server 102A. As other examples, information identifying the manufacturer, a help file describing the use and operation of the module, platform information, time and date information, and/or any other useful information for registration of the measurement module 108 may be provided to the MMIP server 102A. In one embodiment, an icon may optionally be provided for representing the module 108 in a graphical environment, such as in a palette or configuration diagram.

Finally, in 1712, the program(s) may be provided to the MMIP server 102A for storage on the server 102A, or on a memory medium coupled to and accessible by the server 102A. The MMIP server 102A may subsequently be accessible by clients for retrieval of the stored program(s), as described below with reference to FIG. 18.

In one embodiment, the MMIP program(s) may be created initially as a graphical program, such as a LabVIEW graphical program (or alternatively, as a text-based program). As is well-known in the art, in general, compilation of a program to an FPGA bitstream often requires a substantial amount of time, e.g., hours. Thus, the registering entity, e.g., the manufacturer, may create the graphical program(s) (or text-based program(s)), and compile the program(s) to a bitstream (or multiple bitstreams) suitable for deployment on an FPGA. The bitstream(s) may then be stored on the server 102A, as described above.

In another embodiment, the manufacturer (or other entity), may create the graphical (or text-based) program(s), and register the module and program(s), as described above. The MMIP server 102A, or another computer system, may then compile the program(s) into corresponding bitstreams for deployment on an FPGA. The resulting bitstream(s) may then be stored for access by clients, as described below. In yet another embodiment, the graphical program(s) (and/or text-based program(s)) and the bitstream(s) may be registered with the MMIP server 102A, such that the MMIP may be provided to clients with different carrier platforms, e.g., processor/memory based carriers and FPGA based carriers.

In the case where a module is configurable to perform a variety of different functions, the module may have a corresponding variety of interface protocols which may be provided or specified to the server as part of the measurement module registration process. Identifying information for the various versions (functional configurations) of the module, e.g., functional descriptions, may be used to indicate the appropriate interface protocol. Thus, a module or cartridge 108 may have multiple personalities or configurations with corresponding different bitstreams for implementing the respective interface protocols for each personality.

In one embodiment, the MMIP server 102A may be maintained or operated by or on behalf of the manufacturer. The MMIP server 102A may store a plurality of MMIPs for a variety of different measurement modules. In another embodiment, the MMIP server 102A may comprise an MMIP "clearing house". In other words, the MMIP server 102A may be used by many different manufacturers to register their respective measurement modules. Thus, the MMIP server 102A may provide a central repository for MMIP programs for many different measurement modules made by a variety of manufacturers. In one embodiment, the registration may require a fee, and so the registration information may include payment or billing information, such as a credit card number or billing account number.

In one embodiment, the MMIP server 102A may also be accessed by the manufacture (or other entity) to update the MMIP program(s) for the measurement module, e.g., by providing a replacement or additional program(s) for the module. The MMIP server 102A may maintain a list of customers or clients and may notify the customers of updates or additions to the MMIP programs stored on the server 102A.

Figure 18:
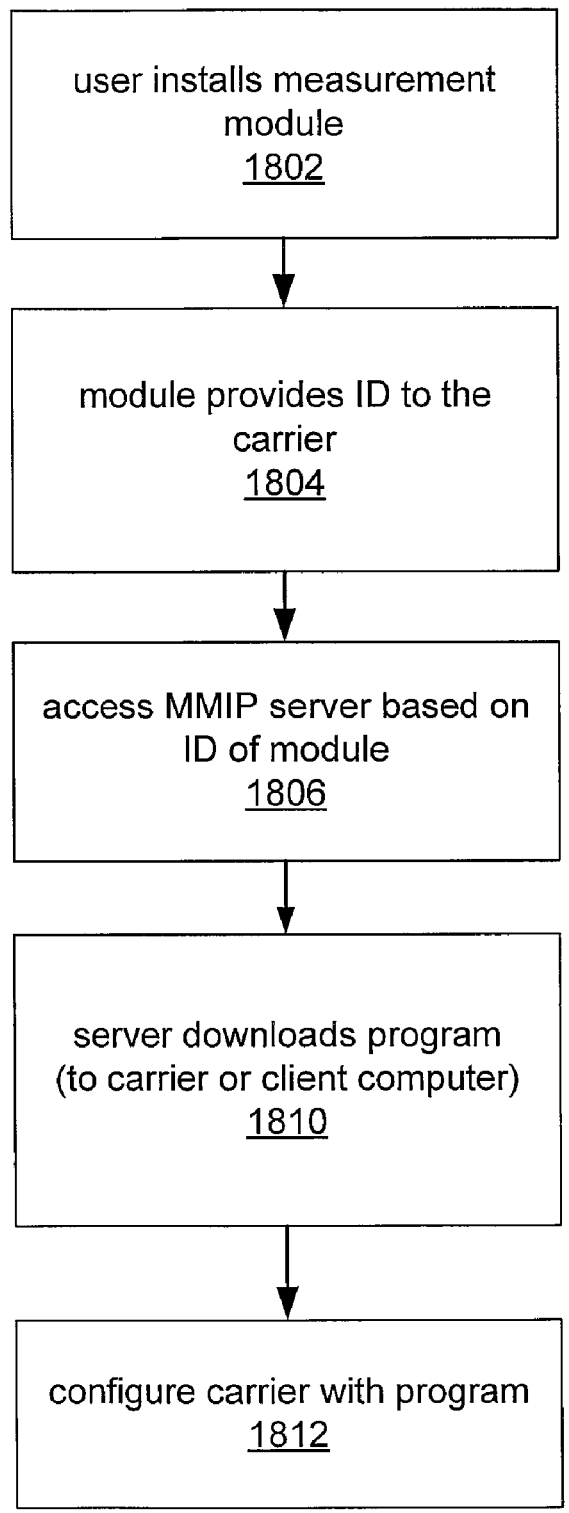
FIG. 18 is a flowchart of a method for configuring a measurement cartridge.

FIG. 18—Method for Configuring a Measurement Module Using an MMIP Server

FIG. 18 is a flowchart of a method for configuring a measurement module using an MMIP server 102A, according to one embodiment of the present invention. As noted above, in some embodiments, various of the steps may occur concurrently, in a different order than shown, or may be omitted. One or more additional steps may also be performed as desired.

In 1802, a user may install a measurement module 108. For example, the user may insert the measurement module 108 into a slot on a carrier 110. Then, in 1804, the module 108 may provide an ID to the carrier, where the ID identifies the module 108. In one embodiment, the ID information may be stored in the EPROM 307 of the module 108, as described above.

In response to the provided ID, the MMIP server 102A may be accessed, e.g., over a network, such as the Internet, based on the ID of the module 108, as indicated in 1804. In other words, the MMIP server 102A may be accessed, and the ID of the module provided to the server 102A. In one embodiment, the carrier 110 may access the server 102A and provide the ID to the server 102A. In another embodiment, the carrier 110 may provide the module ID to a computer system, such as the client computer system 102, and the computer system 102 may access the MMIP server 102A and provide the module ID to the server 102A. In one embodiment, in addition to the ID, information indicating the carrier platform may also be provided to the MMIP server 102A, such as, for example, information specifying whether the carrier is processor based, or FPGA based. In one embodiment, accessing the MMIP server 102A to retrieve an MMIP may require a fee, and so the information provided to the server 102A may include payment or billing information, such as a credit card number or billing account number.

In one embodiment, the carrier 110 or the computer system 102 may access the server 102A to request any updates available for the MMIP of a module. In another embodiment, the carrier 110 may request the update through the computer system 102. Information indicating the version of a currently held MMIP may be provided to the server 102A which may then determine whether a more recent version, or an alternative version, is available, and indicate this to the requester.

As indicated in 1810, in response to receiving the module ID, the MMIP server 102A may download the appropriate program(s) to the carrier 110, according to one embodiment. In another embodiment, the MMIP server 102A may download the appropriate program(s) to the computer system 102. In other words, the program corresponding to the module ID and possibly the carrier platform type (e.g., processor vs. FPGA) may be selected by the MMIP server 102A and downloaded.

Finally, in 1812, the carrier 110 may be configured with the program(s). In an embodiment where the program was downloaded to the computer system 102, the computer system 102 may configure the carrier 110 with the program. In another embodiment, the MMIP server 102A may install the program directly on the carrier 110. For example, if the carrier's functional unit is a processor and memory, the program may simply be stored in the memory of the carrier 110. If the carrier's functional unit comprises a programmable hardware element, e.g., an FPGA, then the computer system 102 (or alternatively, the MMIP server 102A) may configure the FPGA with the program, i.e., the bitstream.

In an embodiment where the program was downloaded to the carrier 110, and where the carrier's functional unit is an FPGA, a processor on the carrier 110 may configure the FPGA with the program, i.e., the bitstream.

In one embodiment, while the program(s) are being downloaded, e.g., to the carrier 110 or the computer system 102, an animated configuration diagram may be displayed on the computer system 102 illustrating the transfer of the program(s) from the server 102A to the system. For example, the configuration diagram may include icons representing the various components of the measurement system, as well as the MMIP server 102A. The transfer may be represented by arrows or other symbols moving from the server icon to an icon representing the carrier 110 or computer system 102, although other animated representations of the transfer are also contemplated. Similarly, when the program(s), are being deployed on the carrier 110, the deployment may be illustrated by the animated configuration diagram, showing the bitstream or program being deployed on the carrier from or by the computer system 102.

Once the carrier 110 has been configured with the program, the carrier 110 and measurement module 108 may be operable to function together, communicating in accordance with the MMIP of the module 108. For example, an application executing on the computer system 102 or on the carrier 110, may invoke operation of the carrier 110 and/or module 108 to perform a measurement, control, or other type of task. Exemplary embodiments of the system described above are presented in detail below with reference to FIGS. 19-39

EXEMPLARY EMBODIMENTS OF THE INVENTION

FIGS. 19-39 illustrate exemplary embodiments of the system described above. It is noted that the embodiments described are meant to be illustrative only, and are not intended to limit the invention to any particular form.

As mentioned above, the measurement modules 108 (e.g., cartridges) may have an interface that defines an SPI mode (with an SPI port, control signals, and triggering signals); an ID mode (to identify the module 108 and sensors attached to it); and a pass-through digital mode (for direct control of digital lines). The ID mode may strictly defines the use of the interface, but the SPI mode may leave it flexible. Because of this flexibility, measurement modules can be very efficient in both price and performance, e.g., comprising only identification, signal conditioning, and ADC/DAC conversion (in the case of analog modules)—with the converter directly controlled by the Module Interface.

The freeform nature of this interface may require the definition of a Serial Communication Block with a standardized interface to create consistency among the various measurement modules. This Serial Communication Block may include a mechanism (which could be implemented, for example, in VHDL, microcontroller code, or possibly in LV-FGPA 'G' code, among others) for presenting an interface to the measurement module 108 that is common among different module types, described below. In various embodiments, the interface mechanism may be easily implementable as either soft registers in an FPGA, hard VHDL, or microcontroller assembly code.

Figure 19:
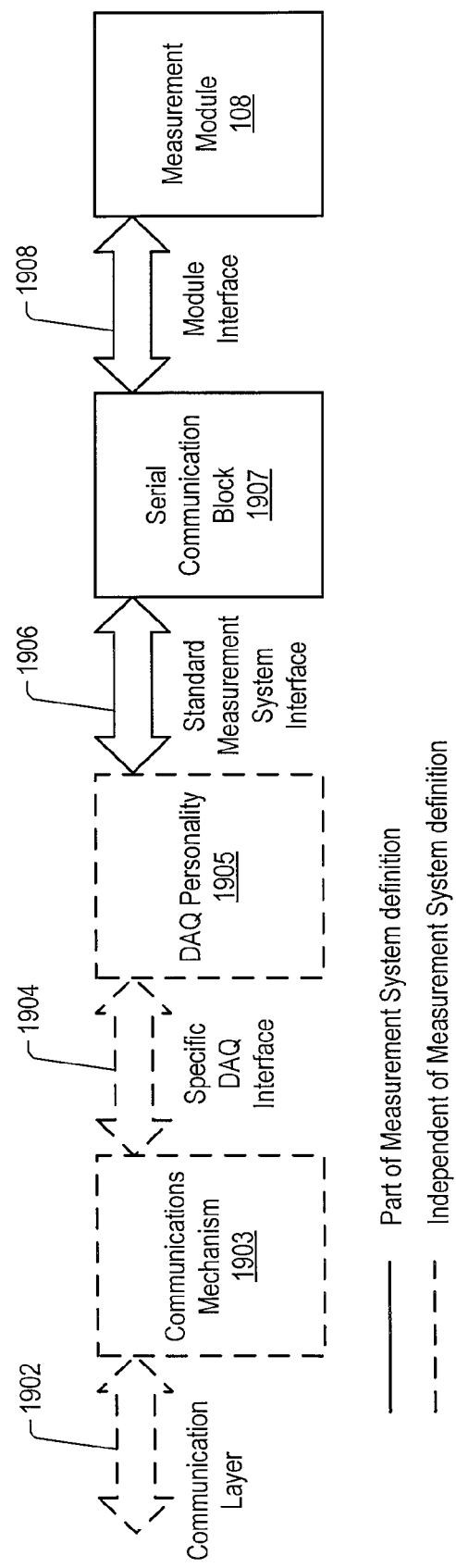
FIG. 19 illustrates communication layers and interfaces in the measurement system, according to one embodiment.

FIG. 19—Communication Interfaces of the Measurement System

FIG. 19 illustrates communication layers and interfaces for the measurement system, according to one embodiment of the invention. More specifically, FIG. 19 illustrates how the Serial Communication Block may fit into a larger measurement system, according to one embodiment. The purpose of each layer or interface is described below, with some examples.

Communications Layer 1902: communications physical and protocol layers, such as PCI/PXI, Ethernet/Logos, USB, serial/Modbus, among others.

Specific DAQ Interface 1904: interface for the DAQ personality. For example, an MIO-style personality might use FIFOs and interrupts, a control or FieldPoint-style personality might use most recent value data registers. In one embodiment, some personalities may require configuration and setup register sets.

Communications Mechanism 1903: hardware and/or firmware that controls the Communications Layer 1902 and protocol stacks, and maps these to the DAQ Interface 1904. Examples of communications mechanisms include National Instruments' miniMITE, a microcontroller with Modbus stack, and a USB controller running a register-level protocol, among others.

DAQ Personality 1905: provides the mechanisms for timing, scanning, and/or controlling the DAQ functions—analogous to an STC chip on an MIO, or microcontrollers and firmware on a FieldPoint analog module, or TIO ASIC on counter-timer boards.

Standard Measurement System Interface 1906: a standardized interface that may facilitate consistent means for triggering, sampling, and configuring various measurement modules. In one embodiment, the interface may comprise an idealized ADC/DAC/register interface.

Module Interface 1908: SPI port, control lines, and trigger lines described above—may provide direct control of ADCs/DACs/signal conditioning.

Serial Communication Block 1907: a mechanism for mapping the functions and registers of the Standard Measurement System Interface 1906 to bit streams, control lines, and trigger lines of the Module Interface 1908. This mechanism may be implemented in a variety of ways, including, for example, FPGA logic or micro-controller assembly code, among others. In various embodiments, a complete description of this mechanism may be burned into the EEPROM of each module 108 or may be provide by a higher-level "driver" layer.

Measurement Module 108: described above, the measurement module 108 may contain just ADCs/DACs and signal conditioning functionality, or may include other functionality as desired.

More detailed descriptions of these layers and interfaces are provided below.

Module Interface 1908, Serial Communication Block 1907, and Standard Measurement System Interface 1906

It is noted that in a preferred embodiment of the measurement system, the Module Interface 1908, the Serial Communication Block 1907, and the Standard Measurement System Interface 1906 may be independent of the other aspects of the system, such as the DAQ Personality 1905, etc. This independence may provide the flexibility to use measurement modules 108 in a variety of disparate products and applications.

As mentioned above, in some embodiments, the measurement modules themselves may provide just the basic functions of signal conditioning and conversion (in the case of analog modules). Scanning, waveform acquisition, timing, synchronization, and other DAQ functions may be performed independent of the measurement modules 108, e.g., as they are independent of the ADC and DAC chips used in other measurement products, i.e., modules, cards or devices. In a complete system, information about the specifics of the Module Interface 1908 (the bits transferred and the use of the control and trigger lines) may be required in order to create the Serial Communication Block 1907 to maintain consistency among different measurement modules. In addition, information about configuration and transfer functions of the signal conditioning may be required to enable setup and post scaling of data. Thus, outside of these descriptions, the implementation of the Serial Communication Block 1907 and configuration of signal conditioning, the rest of the system may be independent of individual measurement modules. Thus, in some embodiments, there may be no particular measurement system API or measurement system driver in that the rest of the system may be a function of the personalities chosen for measurement system. For example, it may be possible to have an E-series measurement system product (using an STC for the DAQ personality), or an NI-1200 measurement system (using 8253s and control logic), or a FieldPoint measurement system (using a microcontroller); but a preferred embodiment of the invention includes RIO-based measurement systems. The example products below indicate exemplary embodiments of how such systems might be put together.

Example of a PCI Board for Control Applications:
  Communications layer: PCI/PXI;
  Communications mechanism: National Instruments' miniMITE;
  Specific DAQ interface: Configuration and setup registers; a data and status register per channel containing the most recently acquired inputs and next outputs to write; a trigger command to sample the inputs; a trigger command to write the outputs;
  DAQ personality: An FPGA that simultaneously scans input devices on the sample trigger and writes this data to the most recent value registers; that reads the output data registers and writes their values to the outputs on the write trigger; and that may contain digital value-add features like PWM, counter, frequency input, pulse measurement, and quadrature input;
  Serial Communication Block: FPGA logic that drives SPI bit streams, control lines, and trigger lines on the Module Interface to perform standard acquisition functions; and
  Module Interface, measurement module: Any combination of measurement modules with defined Module Interfaces.

Example of a USB Carrier for DAQ Applications:
  Communications Layer: USB with a protocol for setting up "tasks" or acquisitions, and for streaming data;
  Communications mechanism: USB slave controller (perhaps 8051 style similar to USB-GPIB designs) with protocol stack and firmware to configure the DAQ personality for tasks and to gather and stream data;
  Specific DAQ interface: Configuration and setup registers, and interrupt (or DMA as appropriate for hardware chosen) paths for passing waveform data, perhaps similar to the interface on a LAB-PC-1200 style product;
  DAQ personality: An FPGA with timers and FIFO for hardware scanning, as well as the digital control logic for interfacing these to the Serial Communication Blocks of the measurement system slots; also general purpose counter/timers and DIO lines for digital measurements;
  Serial Communication Block: FPGA logic that drives SPI bit streams, control lines, and trigger lines on the Module Interface to perform standard acquisition functions; and
  Module Interface, measurement module: Any combination of measurement modules with defined Module Interfaces.

Example of a Simple RS485 Carrier for Monitoring Applications:
  Communications Layer: RS-485 with protocol like Optomux or Modbus;
  Communications mechanism: Simple microcontroller with serial port and firmware to map Optomux commands or Modbus registers to data from measurement system channels;
  Specific DAQ interface and DAQ personality: Firmware in the microcontroller to either read/write single data points to/from the Serial. Communication Block in response to serial requests, or to continuously cycle through the measurement system channels and keep the latest data points available for serial requests;
  Serial Communication Block: Firmware that sequences through the microcontroller's SPI ports and GPIO lines to control a measurement module; and
  Module Interface, measurement module: Any combination of measurement modules with defined Module Interfaces.

Standard Measurement System Interface 1906

In one embodiment, the Standard Measurement System Interface 1906 may comprise an idealized interface to an ADC/DAC converter. The key to the interface is its set of executable methods. These methods may perform initializations, change configurations, acquire single point data, acquire waveforms, and so on. Each measurement module's description may define the methods that it supports. A given implementation of a Serial Communication Block 1907 may support one or many methods at a time—it is up to the particular system which of the methods available to a module may be supported at any given time. For example, a carrier system that only sends single point data on a serial link may never bother to support methods to allow waveform access. A small number of trigger and handshake lines may control the flow of the method; the DAQ personality may connect timer or other control signals to these lines. The DAQ personality 1905 and the Serial Communication Block 1907 may pass information through a set of channel and data/status lines. Finally, a set of configuration registers may maintain the measurement modules' configuration states. In addition to the Standard Measurement System Interface 1906, in one embodiment, a mechanism to set up the methods inside the Serial Communication Block 1907 may also be included in the system (dependent on the implementation).

Figure 20:
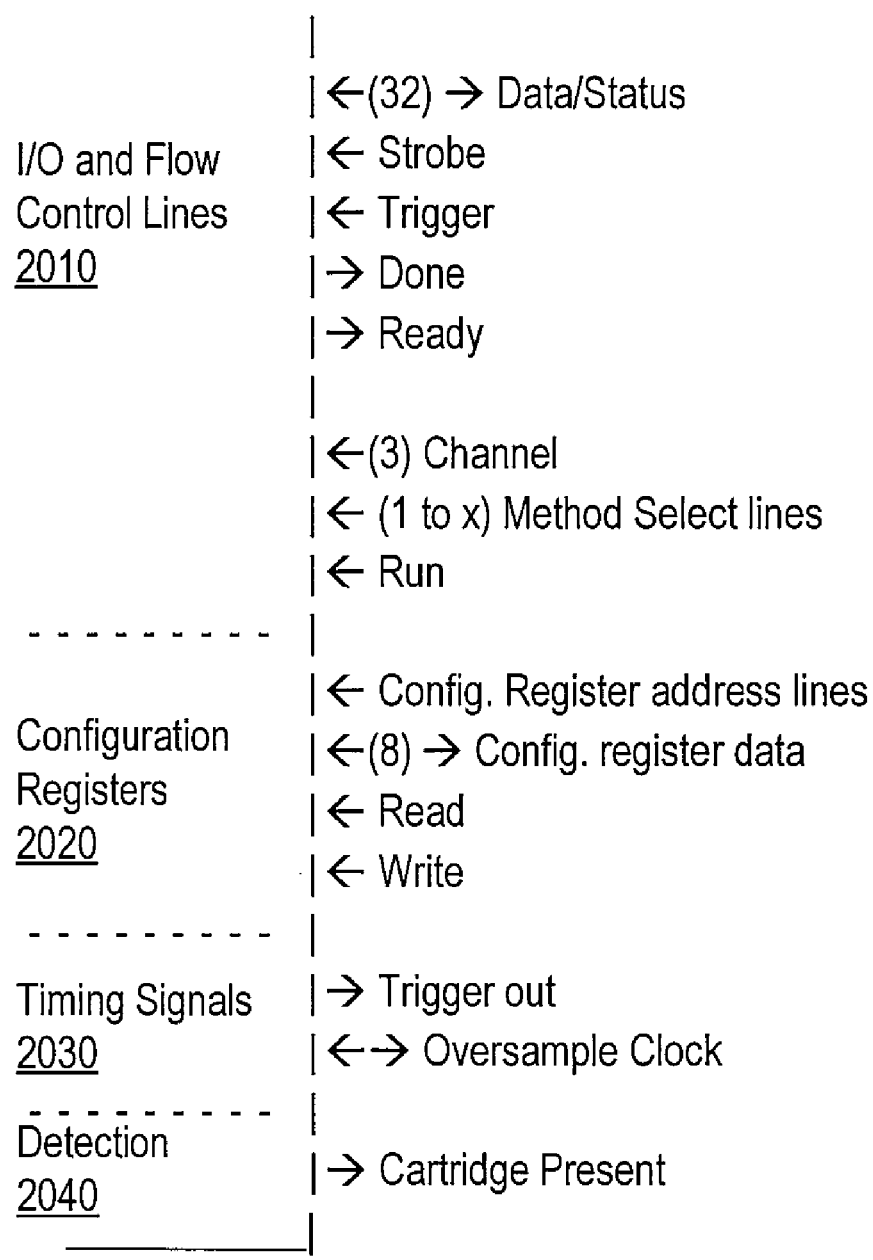
FIG. 20 illustrates a high-level architecture of a standard measurement system interface, according to one embodiment.

FIG. 20—Overview of the Standard Measurement System Interface 1906

FIG. 20 illustrates a high-level architecture of the Standard Measurement System Interface 1906, according to one embodiment of the present invention. It is noted that the architecture describe is meant to be exemplary only, and is not intended to limit the architecture to any particular form. Examples of interface components are here described, including I/O and Flow Control Lines 2010, Configuration Registers 2020, Timing Signals 2030, and Detection 2040.

I/O and Flow Control Lines 2010

Data/status: May be written and/or read, depending on the context of the method being used. The Standard Measurement System Interface 1906 may present one data value (or one data/status pair) at a time, in keeping with a tight coupling to the behavior of the module interface 1908 that serializes accesses to the module 108. A module description format may describe which of these bits are data bits and which are status bits, and may further describe the mapping of the data bits to engineering units, and the meanings and severities of the status bits.

Strobe, Done, Trigger, Ready, Run: Control lines that may set the timing of the method being run and marshal its flow. The use of these lines is defined below.

Channel: Indicates the next channel to be operated on in the method.

Method Select: Selects which of the supported methods to run.

Configuration Registers 2020

Configuration register: Writeable (perhaps with read back, but a measurement module would typically not change the values) registers that set the configuration state of the measurement modules 108.

Timing Signals 2030

Trigger Out, Oversample Clock: Direct control of the corresponding measurement system signals.

Detection 2040

Module Present: The level of the ID_Select line on the Module Interface 1908 (when the Serial Communication Block 1907 is not otherwise driving this line). A high level on this line may indicate the presence of a module 108 while a low level may indicate its absence.

Defined Methods and Operation

A number of common methods may be defined to allow typical software applications and drivers to perform common tasks without requiring customers to be aware of the mechanisms of measurement modules 108 and Serial Communication Blocks 1907. For example, the defined methods may include, but are not limited to:

Initialize: Performed on power up or reset.

Apply new configuration: Performed after new information is written to the configuration registers to apply this configuration.

Acquire single channel: Used for single point or waveform acquisition of a single channel, with one trigger per data point.

Acquire multiple channels: Used for single point scanning or waveform scanning across multiple channels, with one trigger per data point.

Acquire simultaneous channels: Used for single point scanning or waveform scanning across multiple simultaneously sampled channels, with one trigger per scan.

Synchronize self-timed channels: Used to synchronize the channels of a self-timed ADC (e.g., a delta-sigma (D-S) ADC running off of the Oversample Clock), with one trigger to start/synchronize the acquisition of the channels.

Acquire self-timed synchronous channels: Used for waveform acquisition of a single channel or waveform scanning across multiple channels of a self-timed ADC (e.g., a D-S ADC running off of the Oversample Clock) that has previously been started with the Synchronize Self-Timed Channels method, with the ADC indicating the completion of each scan.

Write single point: Used for single point update of a single channel, with one trigger to update that sample.

Write multiple points: Used for single point updates of multiple channels or waveform generation across one or multiple channels, with one trigger per sample.

Write simultaneous channels: Used for single point or waveform updates of multiple simultaneously updated channels, with one trigger per update.

These defined methods enable higher-level software, which may understand how to deal with or even abstract these functions, to automatically map these functions to the behavior of that software. However, measurement modules may also define new methods. New methods may require modification of higher-level software to deal gracefully with them, or they may require a lower level of understanding among customers. For example, a module may be developed that defines a new method that alternately triggers an input channel to sample and an output channel to update. Higher-level software may need to be aware of interleaving an input task and an output task to make use of this new feature, or customers may need to understand that the trigger source alternates between these functions and may need to set up low-level configuration of the DAQ personality appropriately. Either way, the ability to add new functions by defining new methods when necessary is provided.

Use of Methods

In general, a method may be started by setting the method select lines to choose the desired method and assert the run line 2101. Depending on the method, the channel and/or data lines may need to be set at this point to indicate on which channel the method is to be started, or what data values to use for this channel. Then one waits for the ready line to become asserted, indicating that the setup portion of the method is finished. The trigger line may then be asserted to execute the timed portion of the method (for example, to take a sample) or the strobe line to step through other portions of the method. The particular method definition may dictate what behaviors the trigger or the strobe actions have, and whether either, both, or neither actions are supported. Also depending on the method, the channel and/or data lines may need to be driven to valid values to set up the next action. When the action is complete (perhaps indicating that data are valid and/or that the method is ready for the next action), the done line may be asserted. When the method is ready for the next trigger, the ready line may be asserted again and the cycle may be repeated. To end the method, the run line may be de-asserted.

Defined Methods

The specific actions, requirements, and behaviors of each of the defined methods are described in the next several sections, according to one embodiment. Additionally, a timing diagram may be presented illustrating signaling for each method.

FIG. 21—Initialize

Figure 21:
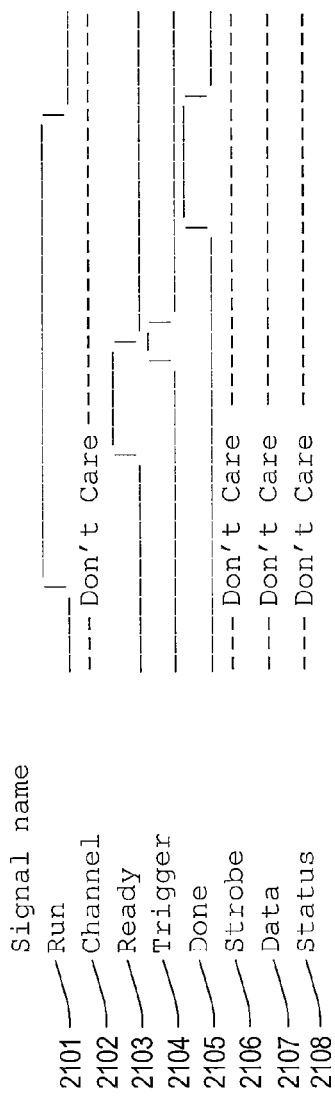

FIG. 21 is a timing diagram for the Initialize method, according to one embodiment. If a module 108 supports the Initialize method, the Initialize method is preferably run after power-up or reset.

After the method select lines are set to select the Initialize method the run line 2101 may be asserted. The channel 2102 and data 2107 lines may not be used for this method. The method may perform any setup steps required before asserting the ready line 2103. After the ready line 2103 is asserted, the trigger line 2104 may be asserted to perform the initialization. The need for timed initialization is weak at best, but this does provide the option of synchronizing the initialization or reset of multiple modules. When the triggered initialization is complete the done line 2105 may be asserted, after which the run line 2101 may be de-asserted to end the method.

Figure 22:
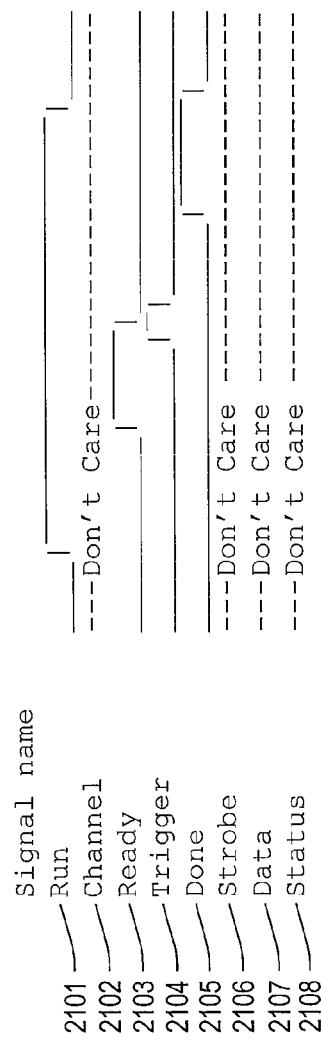

FIG. 22—Apply New Configuration

FIG. 22 is a timing diagram for the Apply New Configuration method, according to one embodiment. If a module 108 supports the Apply New Configuration method, this method is preferably run after any changes are made to the configuration register to apply these changes to the module.

After the method select lines are set to select the Apply New Configuration method the run line 2101 may be asserted. The channel 2102 and data 2107 lines generally are not used for this method. The method may perform any setup steps required before asserting the ready line 2103. After the ready line 2103 is asserted, the trigger line 2104 may be asserted to apply the new configuration parameters. Simultaneously asserting the trigger line 2104 may synchronize the application of new configuration parameters of multiple modules. When the application of the new configuration parameters is complete the done line 2105 may be asserted, after which the run line 2101 may be de-asserted to end the method.

Figure 23:
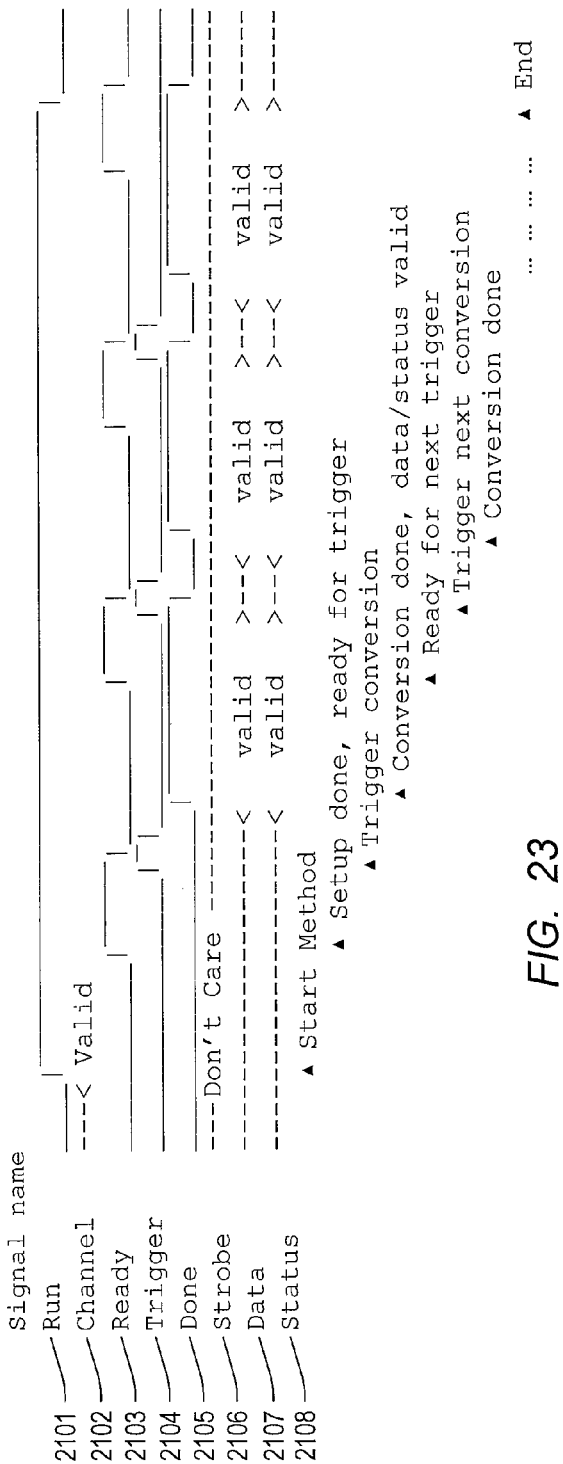

FIG. 23—Acquire Single Channel

FIG. 23 is a timing diagram for the Acquire Single Channel method, according to one embodiment. If a module 108 supports this method for one or more channels, it may be used for single point or waveform acquisition of a single channel, with one trigger per data point. Multiple channels may be of course be scanned by repeatedly applying this method to multiple channels, however it is likely that other methods, if supported, may be better suited to that task.

After the method select lines are set to select the Acquire Single Channel method the run line 2101 may be asserted. The channel lines 2102 may then be set to the channel to be acquired. The method may perform any setup steps required before asserting the ready line 2103. After the ready line 2103 is asserted, the trigger line 2104 may be asserted to trigger the A/D conversion. Simultaneously asserting the trigger line 2104 on multiple modules may synchronize the sampling of a channel on each of the modules. When the conversion is complete and the data are valid the done line 2107 may be asserted, after which the data 2107 and status 2108 lines may be read. When the method is ready for the next trigger, the ready line 2103 may be asserted again and the cycle repeated. Driving the trigger line 2104 with a timer may allow for waveform acquisition, but the timer period is preferably long enough to allow the ready line 2103 to be reasserted and for the data to be read between triggers. A de-asserted level on the ready line 2103 when the timer attempts to assert the trigger line 2104 may be operable to detect a too fast timer. To end the method, the run line 2101 may be de-asserted.

Figure 24:
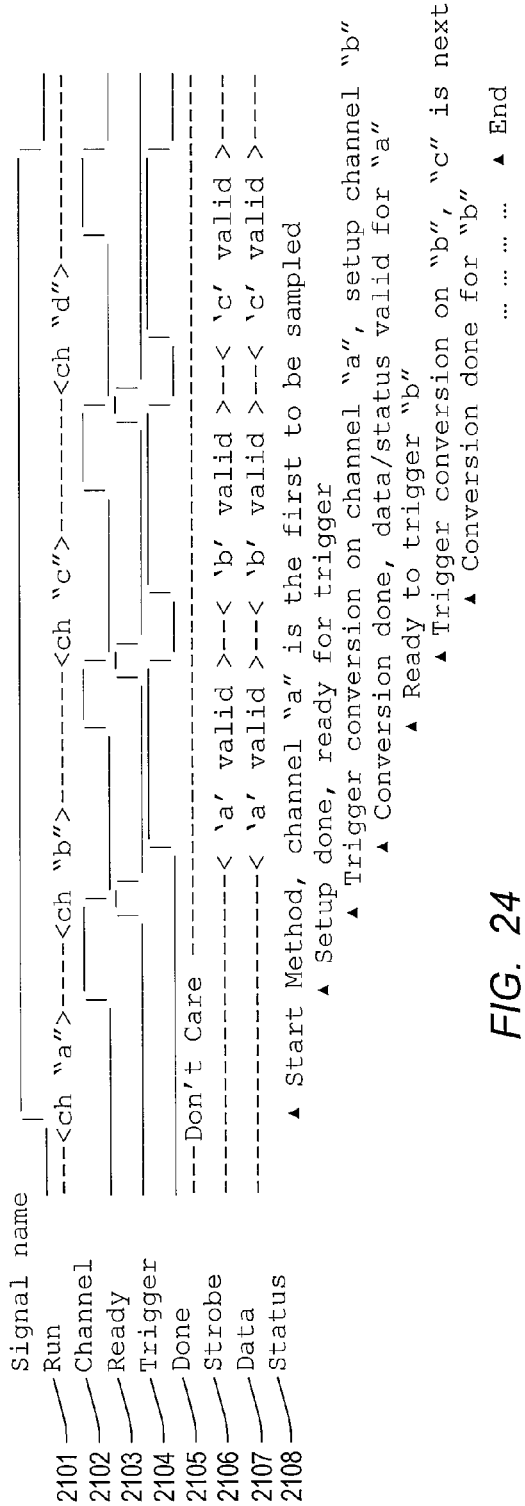

FIG. 24—Acquire Multiple Channels

FIG. 24 is a timing diagram for the Acquire Multiple Channels method, according to one embodiment. If a module 108 supports this method for one or more channels, it may be used for single point scanning or waveform scanning across multiple channels, with one trigger per data point. Single channels may be of course be sampled by applying this method to only one channel, however, the Acquire Single Channel method, if supported, may be better suited to that task. (For example, the Acquire Single Channel method may not need to wait for amplifier settling between conversions.)

After the method select lines are set to select the Acquire Multiple Channels method the run line 2101 may be asserted. The channel lines 2102 may be set to the first channel to be acquired. The method may perform any setup steps required before asserting the ready line 2103. After the ready line 2103 is asserted, the trigger line 2104 may be asserted to trigger the A/D conversion on the first channel. The channel lines 2102 may preferably be set for the next channel to be converted by the time the trigger line 2104 is asserted. Simultaneously asserting the trigger line 2104 on multiple modules may synchronize the sampling of a channel on each of the modules. When the conversion is complete and the data are valid the done line 2105 may be asserted, after which the data 2107 and status 2108 lines may be read. When the method is ready for the next trigger, the ready line 2103 may be asserted again and the cycle repeated. Driving the trigger line 2104 with a timer may allow for waveform acquisition, but the timer period is preferably long enough to allow the ready line 2103 to be reasserted, for the data to be read, and for the next channel value to be generated between triggers. A de-asserted level on the ready line 2103 when the timer attempts to assert the trigger line 2104 may detect a timer rate which is too fast to for the module to keep up with. To end the method, the run line 2101 may be de-asserted.

Figure 25:
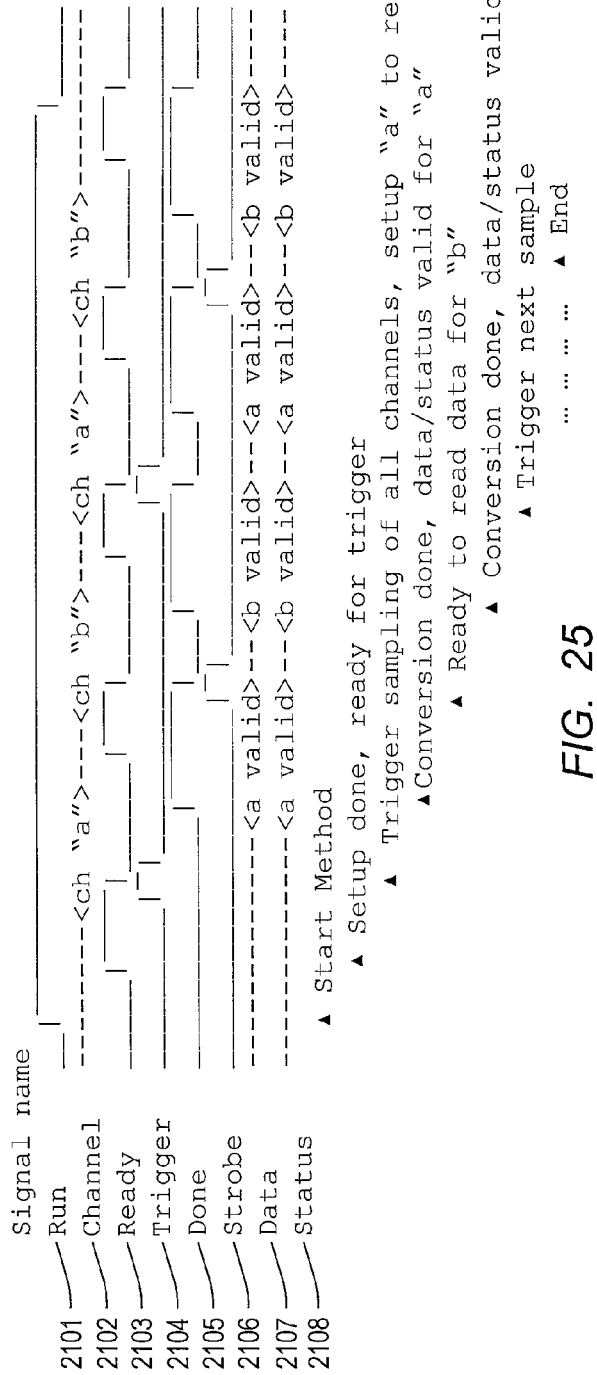

FIG. 25—Acquire Simultaneous Channels

FIG. 25 is a timing diagram for the Acquire Simultaneous Channels method, according to one embodiment. If a module 108 supports this method it may be used for single point scanning or waveform scanning across multiple simultaneously sampled channels, with one trigger per scan. Single channels may be of course be sampled by applying this method to only one channel; however the Acquire Single Channel method, if supported, may be better suited to that task, especially for waveform scanning of a single channel. The trigger line 2104 may be used to sample the channels of the module, while the strobe line 2106 may be asserted once for each data point read out.

The use of this method is similar to that of the Acquire Multiple Channels method, with the exception that the trigger line 2104 may sample the data for all channels and get the data for the first sample, while subsequent channels may be read out using the strobe line 2106. After the method select lines are set to select the Acquire Simultaneous Channels method the run line 2101 may be asserted. The method may perform any setup steps required before asserting the ready line 2103. After the ready line 2103 is asserted, the trigger line 2104 may be asserted to sample all of the input channels. The channel lines 2102 may preferably be set for the first channel to be read by the time the trigger line 2104 is asserted. Simultaneously asserting the trigger line 2104 on multiple modules may synchronize the sampling of all of the channels on all of the modules. When the conversion is complete and the data are valid for the first channel, the done line 2105 may be asserted, after which the data 2107 and status 2108 lines may be read. When the method is ready to read the next channel or to be re-triggered, the ready line 2103 may be asserted again and the strobe line 2106 may be asserted to read another channel or the trigger line 2104 may be asserted to sample all of the channels. To end the method, the run line 2101 may be de-asserted. Driving the trigger line 2104 with a timer may allow for waveform acquisition, but the timer period is preferably long enough to allow the sampling, strobing, and reading of all of the desired channels between runs. A de-asserted level on the ready line 2103 (or an incomplete read of all the channels) when the timer attempts to assert the run line 2101 may indicate a timer rate which is too fast for the module to keep up with.

Figure 26:
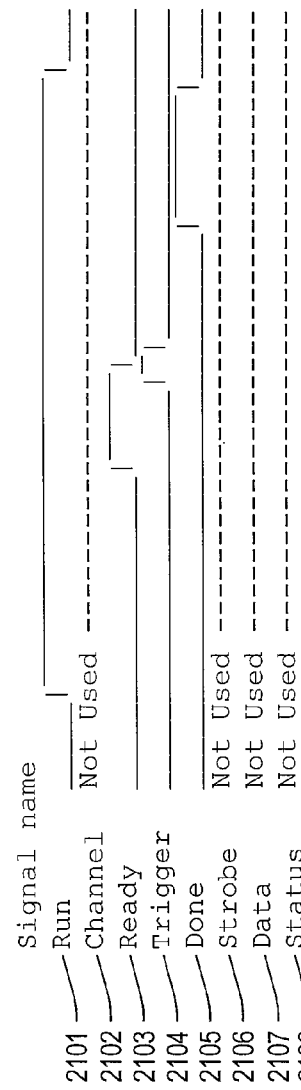

FIG. 26—Synchronize Self-Timed Channels

FIG. 26 is a timing diagram for the Synchronize Self-Timed Channels method, according to one embodiment. If a module 108 supports this method it may be used to synchronize the channels using self-timed ADCs (e.g., a D-S ADC running off of the Oversample Clock), with one trigger to start/synchronize the acquisition of the channels. After the channels of module(s) are synchronously running, the Acquire Self-Timed Synchronous Channels method may be used to read the channels.

After the method select lines are set to select the Synchronize Self-Timed Channels method the run line 2101 may be asserted. The method may perform any setup steps required, then asserts the ready line 2103 to indicate that the ADCs are ready for the synchronizing trigger. The trigger line 2104 may then be asserted to synchronize the ADCs. Driving the trigger line 2104 of multiple modules simultaneously may synchronize the ADCs across the modules. After the ADCs have been synchronized, the done line 2105 may be asserted, after which time it is safe to de-assert the run line 2101 to end the method.

Note: It is possible that this functionality could be contained within the Initialize or Apply Configuration methods for a given module. However, the synchronization of D-S ADCs may take a long time, and so an independent method may be desirable.

Figure 27:
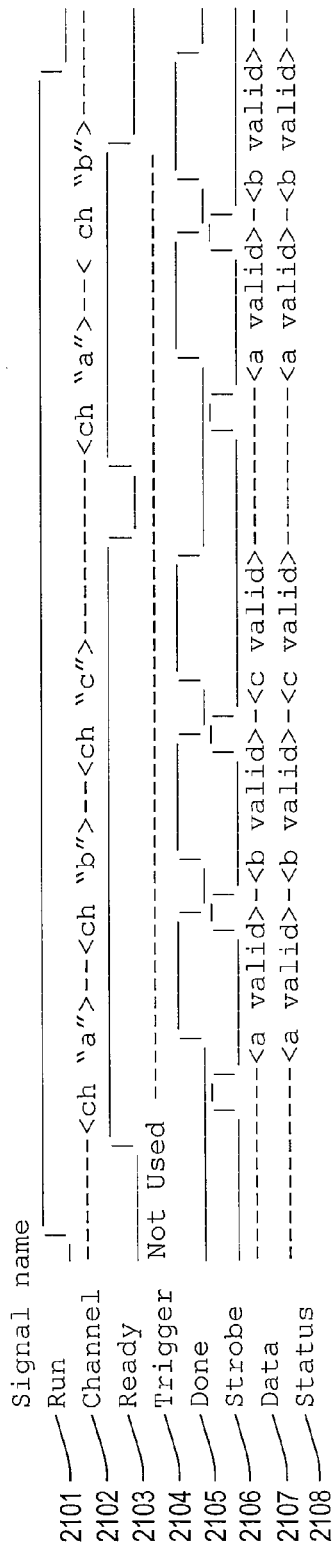

FIG. 27—Acquire Self-Timed Synchronous Channels

FIG. 27 is a timing diagram for the Acquire Self-Timed Synchronous Channels method, according to one embodiment. If a module 108 supports this method it may be used for waveform acquisition of a single channel or waveform scanning across multiple channels of a self-timed ADC (e.g., a D-S ADC running off of the Oversample Clock) that has previously been started with the Synchronize Self-Timed Channels method. The ready line 2103 may indicate that the ADC has completed a scan, and the strobe line 2106 may be used to read out each channel's data.

After the method select lines are set to select the Acquire Self-Timed Synchronous Channels method the run line 2101 may be asserted. The method may perform any setup steps required, then the ready line 2103 may be asserted after the ADC indicates that it has a new set of data sampled. After the ready line 2103 is asserted, channel lines 2102 may be set to the first channel to be read out and the strobe line 2106 may be asserted to start reading that channel. When the channel has been read and the data are valid for the first channel, the done line 2105 may be asserted, after which the data 2107 and status 2108 lines may be read. After reading the data 2107 and status 2108 lines, the strobe 2106 and channel lines 2102 may be asserted to read another channel. To end the method, the run line 2101 may be de-asserted. It may be important to strobe and read all the channels to be scanned before the next ADC sampling. A de-assertion of the ready line 2103 (indicating that the ADC's are re-sampling) before the done line 2105 indicates that the last channel has been read may indicate that the data are not being read out fast enough to keep up with the ADC.

Note: The Acquire Self-Timed Synchronous Channels and the Synchronize Self-Timed Channels methods could be combined in one method, where the trigger line 2104 is used to synchronize all the channels and the strobe line 2106 is used to read out the channels. However, in the preferred embodiment, two methods are used, primarily because the synchronization of multiple D-S ADCs may take a long time, and thus may preferably be performed separately from the acquisition method.

Figure 28:
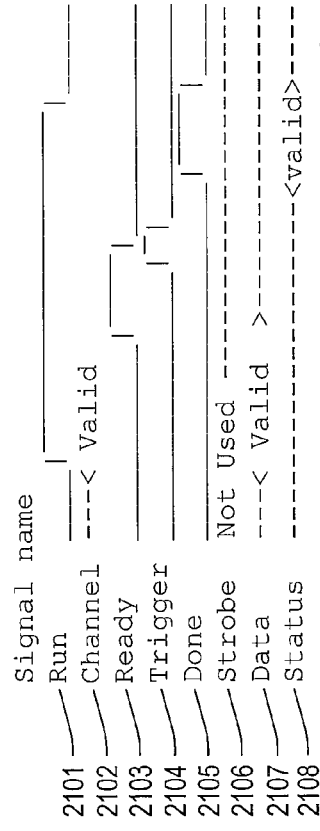

FIG. 28—Write Single Point

FIG. 28 is a timing diagram for the Write Single Point method, according to one embodiment. If a module 108 supports this method for one or more channels, it may be used for single point update of a single channel, with one trigger to update that sample. For multiple updates in a single method (waveform updates of a single channel, single point updates across multiple channels, or waveform updates across multiple channels) the Write Multiple Points method or the Write Simultaneous Channels method may be more efficient.

After the method select lines are set to select the Write Single Point method the run line 2101 may be asserted. The channel lines 2102 may be set to the channel to be updated and the data lines 2107 may be set to the value to update with. The method may perform any setup steps required before asserting the ready line 2103. After the ready line 2103 is asserted, the trigger line 2104 may be asserted to trigger the D/A update. Simultaneously asserting the trigger line 2104 on multiple modules may synchronize the sampling of a channel on each of the modules. When the conversion is complete and any returning status is valid the done line 2105 may be asserted, after which the status lines may be read. To end the method, the run line 2101 may be de-asserted.

FIG. 29—Write Multiple Points

FIG. 29 is a timing diagram for the Initialize method, according to one embodiment. If a module 108 supports this method for one or more channels, it may be used for single point updates of multiple channels or waveform generation across one or multiple channels, with one trigger per data point. Single point updates on one channel may of course be accomplished by applying this method to only one channel, however the Write Single Point method, if supported, may be better suited to that task.

After the method select lines are set to select the Write Multiple Points method the run line 2101 may be asserted. The channel lines 2102 may be set to the first channel to be updated, and the data lines 2107 may be set to the new value for that channel. The method may perform any setup steps required before asserting the ready line 2103. After the ready line 2103 is asserted, the trigger line 2104 may be asserted to trigger the D/A conversion on the first channel. The channel and data lines 2107 may preferably be set for the next channel to be converted by the time the trigger line 2104 is asserted. Simultaneously asserting the trigger line 2104 on multiple modules may synchronize the updating of a channel on each of the modules. When the conversion is complete and the status is valid the done line 2105 may be asserted, after which the status lines may be read. When the method is ready for the next trigger, the ready line 2103 may be asserted again and the cycle repeated. Driving the trigger line 2104 with a timer may allow for waveform updates, but the timer period is preferably long enough to allow the ready and done line 2105 to be reasserted, for the status to be read, and for the next channel and data value to be generated between triggers. A de-asserted level on the ready line 2103 when the timer attempts to assert the trigger line 2104 may detect a timer rate which is too fast to for the module to keep up with. To end the method, the run line 2101 may be de-asserted.

FIG. 30—Write Simultaneous Channels

FIG. 30 is a timing diagram for the Initialize method, according to one embodiment. If a module 108 supports this method, it may be used for single point or waveform updates of multiple simultaneously updated channels, with one trigger per update. Single point or waveform updates on one channel may of course be accomplished by applying this method to only one channel—however the Write Single Point or Write Multiple Point methods, if supported, may be better suited to that task.

After the method select lines are set to select the Write Simultaneous Channels method the run line 2101 may be asserted. The channel lines 2102 may be set to the first channel to be updated, and the data lines 2107 may be set to the new value for that channel. The method may perform any setup steps required before asserting the ready and done line 2105. After the done line 2105 is asserted, the status lines may be read for that channel and more channel and data pairs may be written with the strobe line. After the ready line 2103 is asserted, the trigger line 2104 may be asserted to trigger the D/A conversion on all of the channels. Simultaneously asserting the trigger line 2104 on multiple modules may synchronize the updating of all the channels on all of the modules. When the conversion is complete and the method is ready for more data to be strobed in the done line 2105 may be asserted again and the cycle repeated. Driving the trigger line 2104 with a timer may allow for waveform updates, but the timer period is preferably long enough to allow the ready 2103 and done 2105 lines to-be reasserted, for the statuses to be read, and for the channel and data values to be generated between triggers. If the ready line 2103 is de-asserted or if not all the data/channel pairs have been written when the timer attempts to assert the trigger line 2104, then the timer rate may be too fast to for the module to keep up with. To end the method, the run line 2101 may be de-asserted.

Module Interface

As mentioned above, measurement modules 108 may have an interface that defines an SPI mode (with an SPI port, control signals, and triggering signals); an ID mode (to identify the module 108 and sensors attached to it); and a pass-through digital mode (for direct control of digital lines). The signals for these modes (as well as power and ground signals) may be contained in a 15-pin connector, 13 pins of which may be defined. Although the specific use of the lines and the data transferred on them may be dependent on the particular measurement module, the general purpose of the each of the lines may be defined.

FIG. 31—Module Interface: Pinout

FIG. 31 illustrates one embodiment of a measurement module pinout specification, including 11 signal lines, of which 8 are available in DIO mode. It is noted that the pinout specification is exemplary only, and is not intended to limit the pinout specification to any particular form or feature set.

Signal Descriptions

GND: Ground reference for the power and all SPI mode and ID mode signals.

Power: 4.75 to 5.25 VDC, £100 mA peak current. Inrush current may preferably be limited to an equivalent circuit of 10 mF or less.

Sleep: Active high signal may preferably be driven low by carriers to ensure normal operation on measurement modules supporting a sleep mode. When driven high, measurement modules that support a sleep mode may go into this low power mode. In sleep mode, all signals may be ignored. The ID select pin may continue to be pulled up by the measurement module 108 to indicate the presence or absence of a measurement module ID Select: Detects presence of modules with a strong (1.5 to 3.3 kOhm) pull-up on measurement system and weak pull-down on the carrier. It may be used as a select and frame synch line with SPI_FUNC, SPI_CLK, MISO, and MOSI to determine the type of measurement system by reading from an identification EEPROM or to access plug-and-play sensor information. The EEPROM may contain information about calibration, communication, and identification of the measurement module. Plug and play information may be stored in the sensor through a microLAN 1-wire interface.

SPI_CS: SPI Chip Select line that operates as frame sync for the SPI port. When a measurement module 108 is in SPI mode it may ignore SPI_CLK and MOSI and may not drive MISO when the SPI_CS is held high, but may respond to these signals when SPI_CS is low. Measurement modules may require SPI_CS to go low during each byte or to stay low for groups of bytes. SPI_CS may stay high in ID mode, as the ID Select line provides the select and frame sync functions in this mode.

SPI_FUNC: Qualifies the SPI_CS or ID select to indicate which SPI function is being communicated with on the measurement module. In SPI mode, these functions may be a data port (SPI_FUNC=0) and a configuration port (SPI_FUNC=1), but in general they are two arbitrary ports that the SPI port can point to. In the ID mode, these interfaces may be the configuration EEPROM (SPI_FUNC=1) or the smart sensor/microLAN interface (SPI_FUNC=0).

SPI_CLK: Idle high clock, data are sent on the falling edge and sampled on the rising edge.

MOSI: Master-Out, Slave-In SPI data line.

MISO: Master-In, Slave-Out SPI data line.

Convert: Triggers a converter. Starts an acquisition of an ADC or loads a DAC or latches a shift register. The polarity and edge/level sensitivity of this signal is not predefined, nor is it an absolute requirement that it be used. The command set for an individual module 108 may indicate the usage of this line.

Busy: Indicates the progress of an acquisition, or holds off communication for other purposes (such as powering up from sleep mode or waiting for an amplifier to settle). The polarity and edge/level sensitivity of this signal is not predefined, nor is it an absolute requirement that it be used. The command set for an individual module 108 may indicate the usage of this line.

Trig_Out: A signal generated by the measurement module 108 to act as a trigger for the rest of the system. Examples include a digital input channel or a comparator on an analog input channel.

Oversample Clock: An over-sampling clock for synchronizing continuously clocked data converters, such as D-S converters. Modules may be able selectively clock their converters from either an internal clock or from this line, and they may be able to selectively drive this line with the internal clock. In a multi-module system, one module 108 may drive this line with its internal clock, while the carrier routes that signal to all the other modules to be synchronized with the first.

Reserved: Lines not specified yet for measurement modules. One possible line that could be defined is a SPI_CLK_OUT line, which the measurement module drives as a copy of the clock, but a copy that source-synchronous with respect to the MISO line. Defining such an SPI_CLK_OUT line may allow for faster SPI rates. It may impact the cost of isolation by allowing slower isolators to be used on the SPI port, but it may also require an additional isolator for the return clock. Other uses for this line could be as additional power supplies (such as 3.3 V, ±10 V, 24 V) or additional select lines for added functionality, or as local communications between modules.

ID, SPI, and DIO Modes

All measurement modules according to the present invention preferably support the ID mode. The ID mode is entered whenever the ID Select line is driven low. In the ID mode, the SPI_FUNC, SPI_CLK, MOSI, and MISO lines of the measurement module may all behave as specified for ID mode operation. The carrier may avoid driving the SPI_CS line low during ID mode to prevent the SPI lines from attempting to access data or configuration interfaces.

If the configuration EEPROM indicates that the type of the interface is generic DIO, then (whenever the ID Select line is high) 8 lines may be made available as generic digital I/O. If the configuration EEPROM indicates that the type of the interface is SPI, the lines may operate as indicated above.

Signal Levels, Pull-Ups, and Pull-Downs

In one embodiment, all of the module interface signals may be defined as 3.3 V LVTTL compatible and 5 V tolerant. The carrier may be able to keep it's signals in a tri-state mode with no module present, and if it uses pull-ups/-downs or keeper circuits they may be weak enough to be overdriven to valid levels by module pull-ups/downs of up to 10 kOhms (pulled to either 5 V or Ground). The module 108 may use such pull-up/-down resistors, in particular to establish proper power-up behavior and to prevent recognition of the SPI_CS as being driven to a valid active low while the carrier holds it as a tri-state with a week keeper circuit or pull-up. Further information on the defined mechanisms and responsibilities for power-up behavior is provided below in the sections titled Power-Up and Hot-Swap Behavior.

Figure 32A:
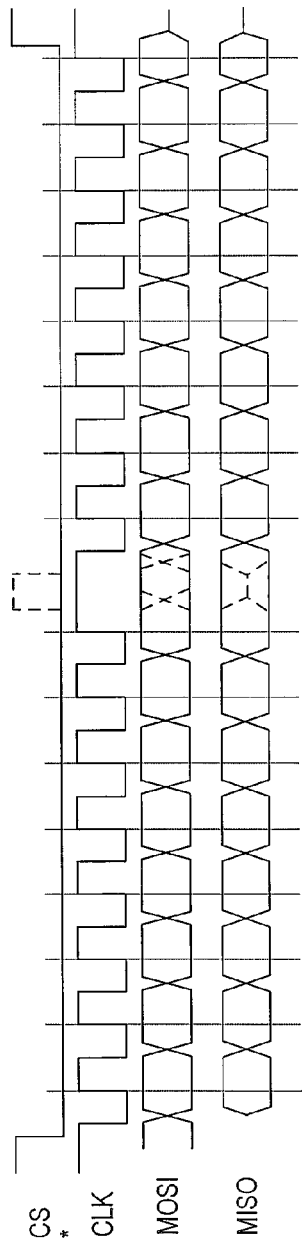
FIGS. 32A and 32B illustrate SPI signal timing, according to one embodiment.
Figure 32B:
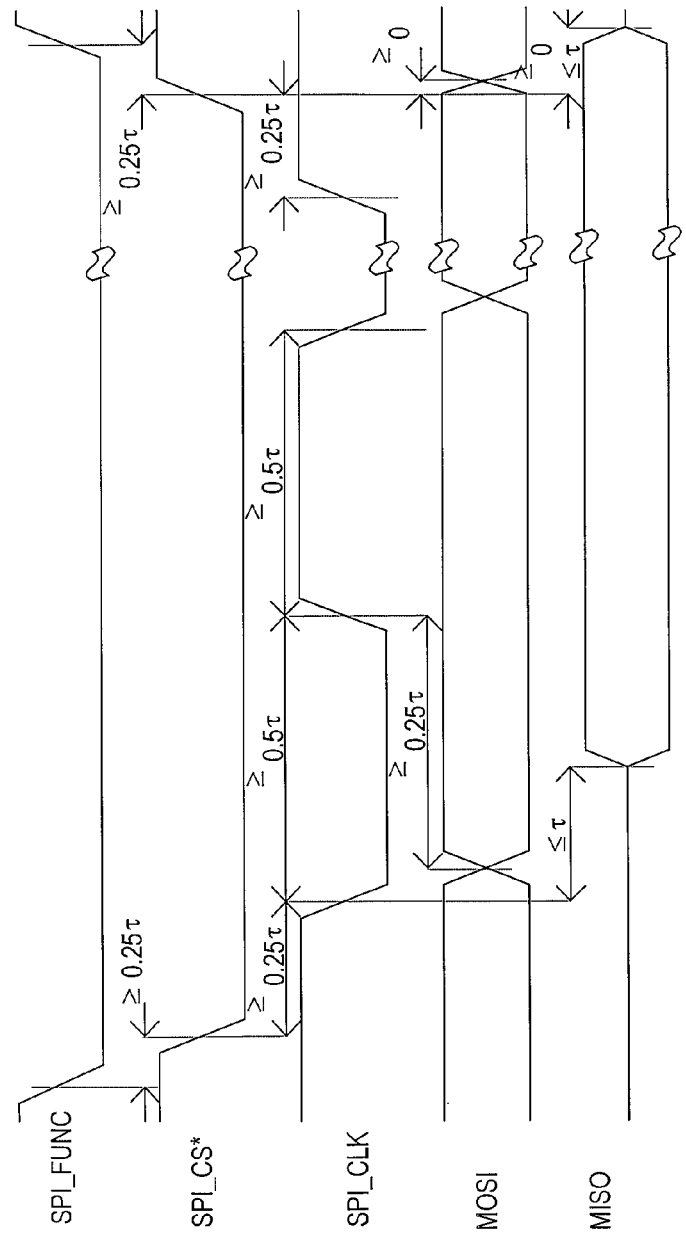

FIGS. 32A and 32B—SPI Signal Timing Relationships

FIGS. 32A and 32B illustrate SPI signal timing relationships, according to one embodiment of the invention.

FIG. 32A—SPI Timing Relationships

FIG. 32A illustrates SPI timing relationships, according to one embodiment. More specifically, FIG. 32A illustrates the timing relationships between the CS, CLK, MOSI, and MISO signals, as shown.

FIG. 32B—SPI Timing

FIG. 32B illustrates SPI timing, according to one embodiment. More specifically, FIG. 32B illustrates SPI timing for SPI_FUNC, SPI_CS, SPI_CLK, MOSI, and MISO signals, as shown. In this embodiment, t (tau)=a time constant defined in the module's configuration EEPROM 307. A module 108 may meet or require the timing constraints above for the given t. The SPI_CLK falling to MISO valid is usually the limiting factor, so normally a carrier may add it's SPI_CLK and MISO delays to t to determine a new time, t'. This t' may be used as either the clock half-period (if the carrier samples MISO on the rising edge) or as the full clock period (if the carrier samples MISO on the next falling edge). Sampling MISO on the falling edge may allow for double the clock rate, but may require the carrier to generate an internal extra falling clock edge.

Figure 33A:
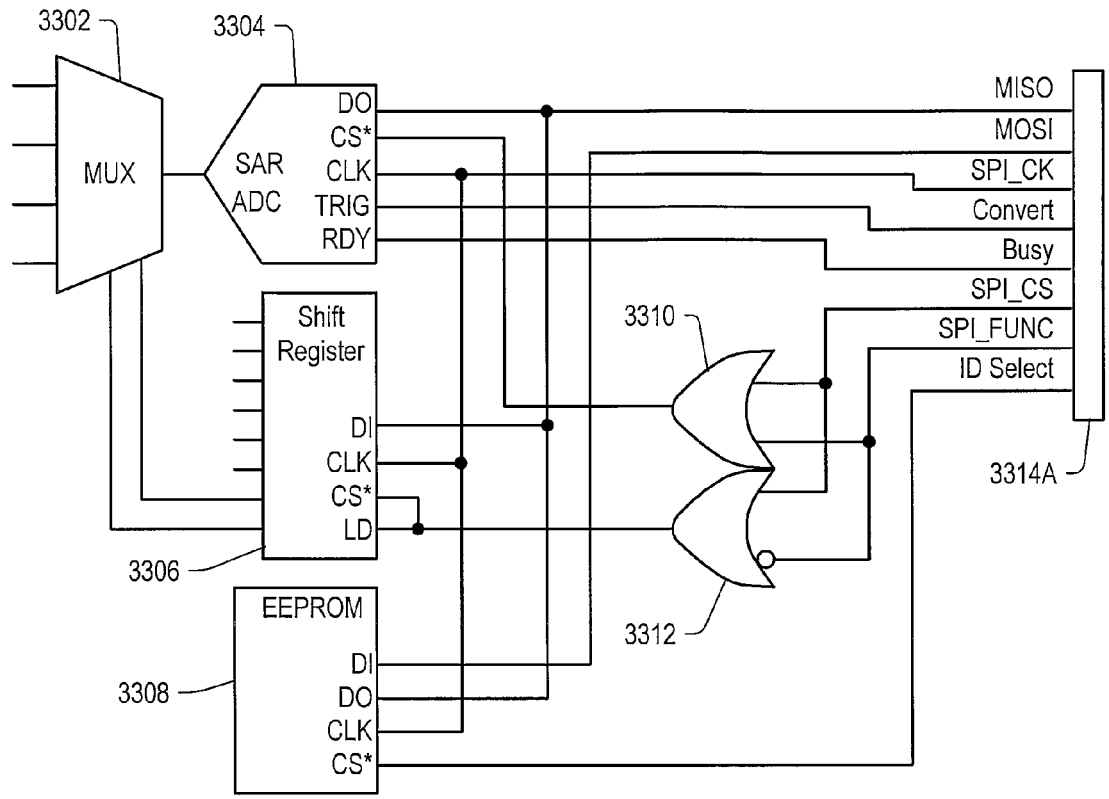
FIGS. 33A-33C are example circuit diagrams for various measurement modules, according to one embodiment.
Figure 33B:
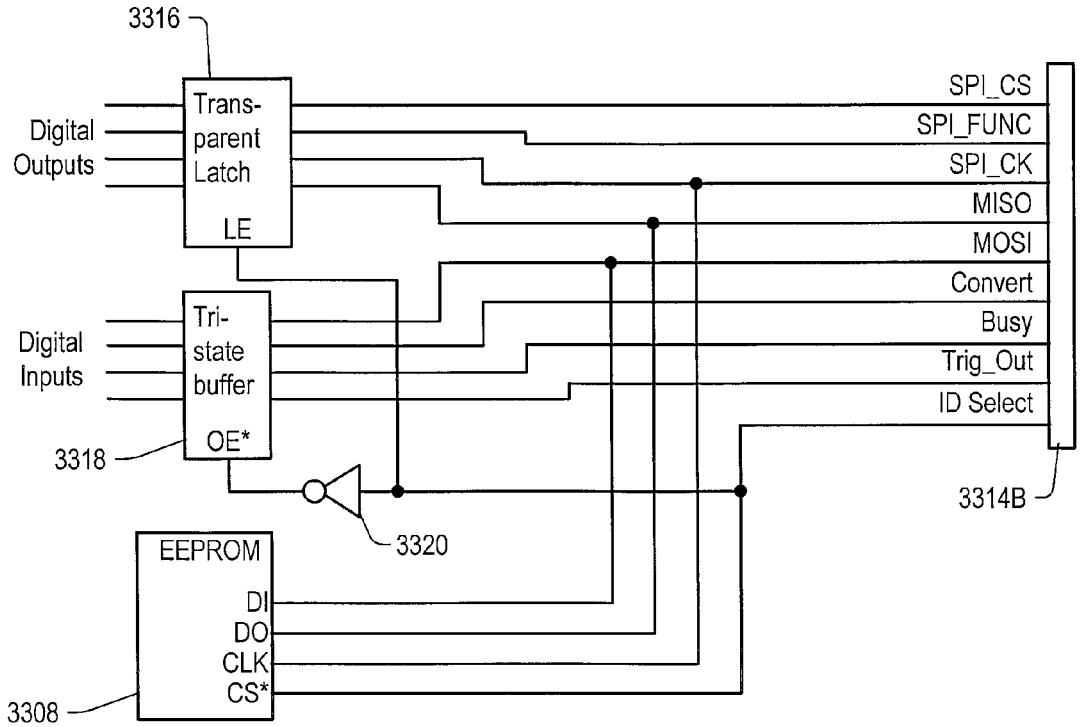
Figure 33C:
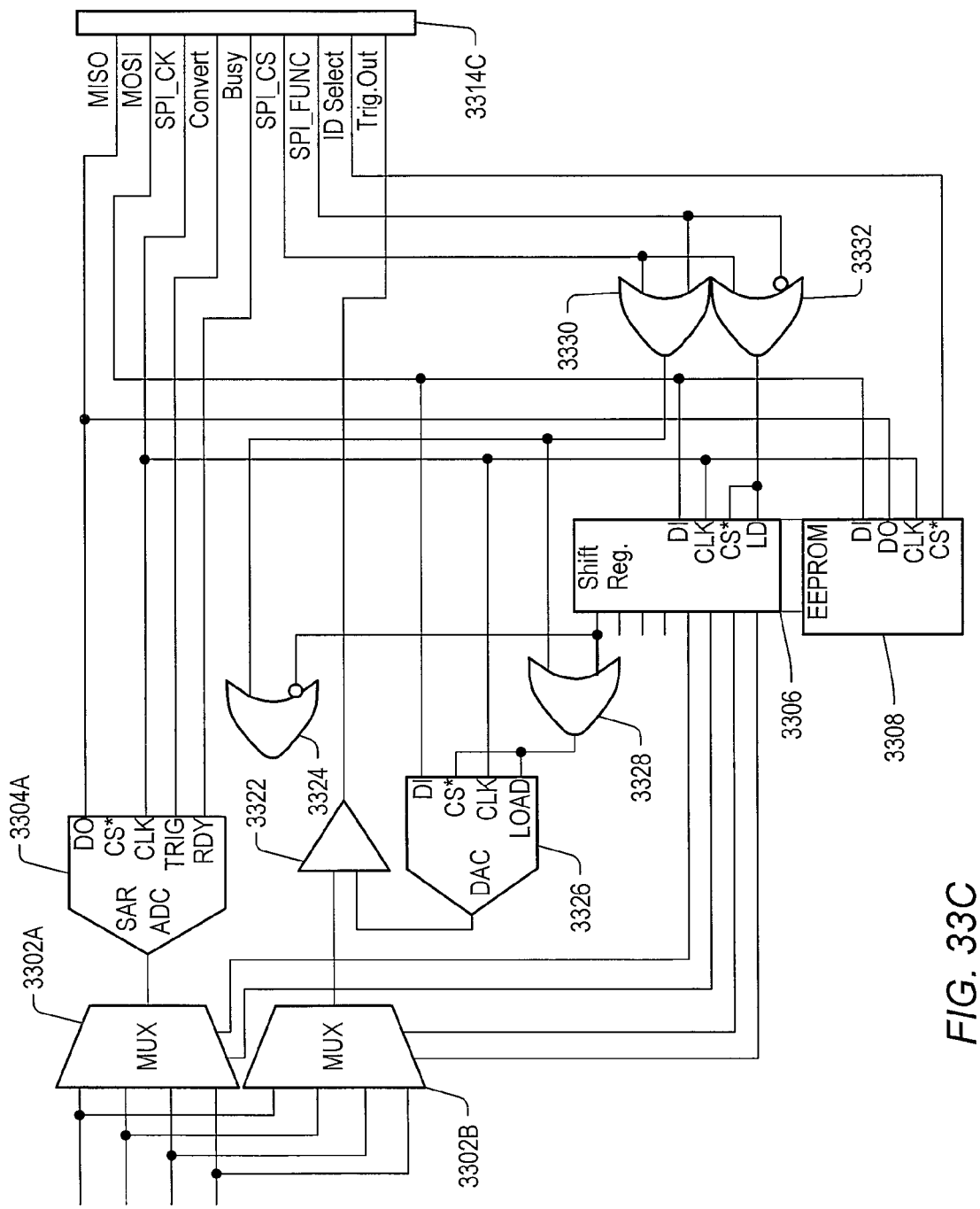

FIGS. 33A-33C—Circuit Examples: Measurement Modules

FIGS. 33A-33C are diagrams of example circuits of measurement modules, according to one embodiment. It is noted that these circuits are intended to be illustrative only, and are not intended to limit the circuitry of measurement modules to any particular form or architecture. FIG. 33A is a circuit diagram for a 4-Channel MUxed Analog Input module, according to one embodiment. FIG. 33B is a circuit diagram for an 8-Channel (4 in, 4 out) Pass-Through Digital module, according to one embodiment. FIG. 33C is a circuit diagram for a 4-Channel MUXed Analog Input w/Analog Trigger, according to one embodiment.

FIGS. 33D-33G—Circuit Examples: Measurement Modules with RIO FPGA

FIGS. 33D-33G are diagrams of example circuits of measurement modules 108 coupled to RIO FPGAs 308, according to one embodiment. In these embodiments, RIO provides back-end functionality for the measurement module, providing one or more functions for control, communication, and/or processing for the module 108. It is noted that these circuits are intended to be illustrative only, and are not intended to limit the circuitry of measurement modules 108 and/or RIO FPGAs 308 to any particular form or architecture.

Figure 33D:
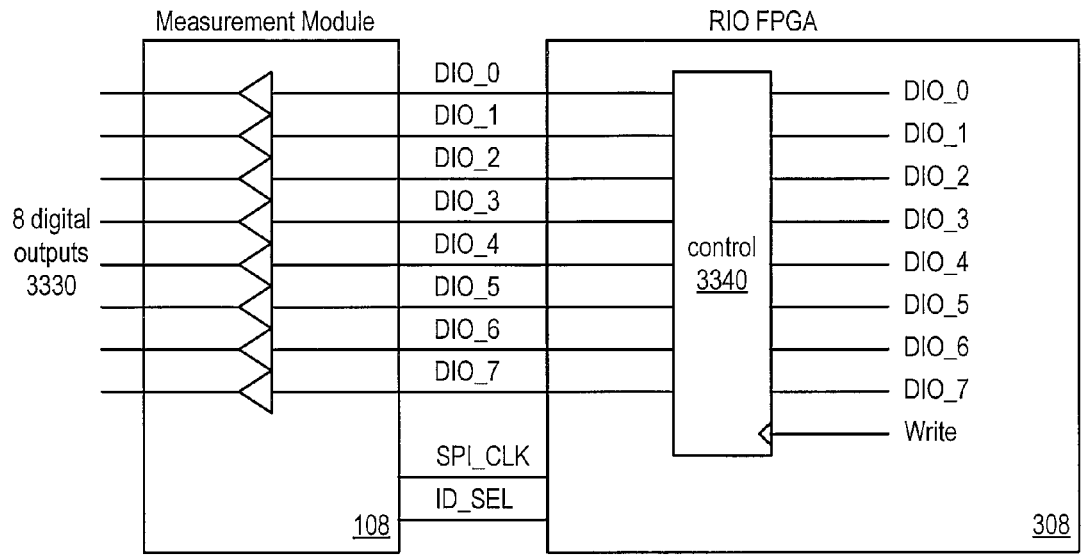
FIGS. 33D-33G are example circuit diagrams for various measurement module/RIO FPGA configurations, according to one embodiment.

FIG. 33D is a circuit diagram for a simple 8-channel digital output, according to one embodiment. In this embodiment, the RIO FPGA 308 operates to send digital signals via control 3340, over 8 digital lines (DIO_0-DIO_7) to the measurement module 108, which may then provide the signals as output through 8 respective digital outputs 3330, as shown.

Figure 33E:
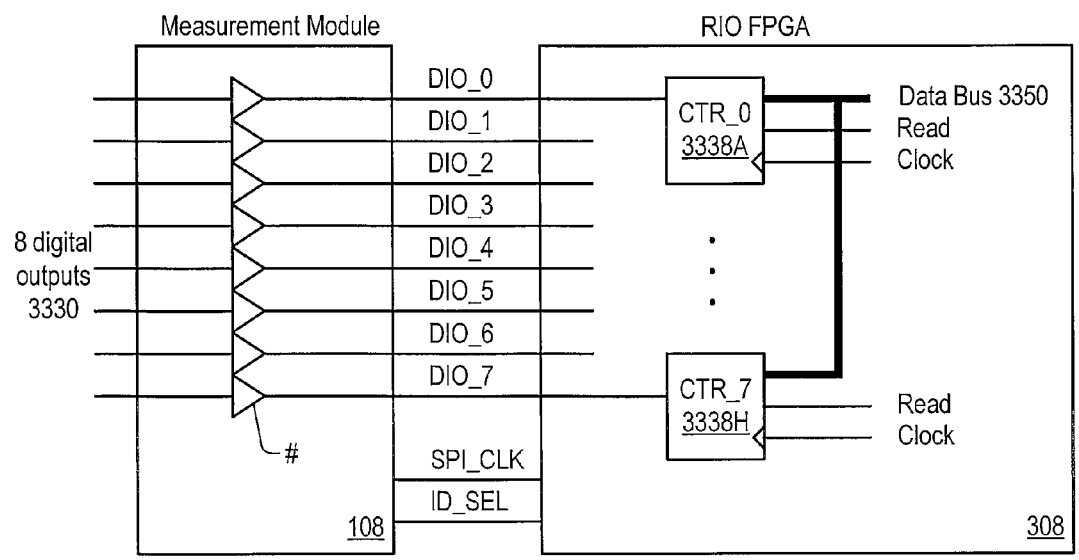

FIG. 33E is a circuit diagram for an 8-channel event counter, according to one embodiment. In this embodiment, the RIO FPGA 308 is configured with 8 counters 3308A-3308H which may operate to receive event signals from a data bus 3350, and send count signals to the measurement module 108.

Figure 33F:
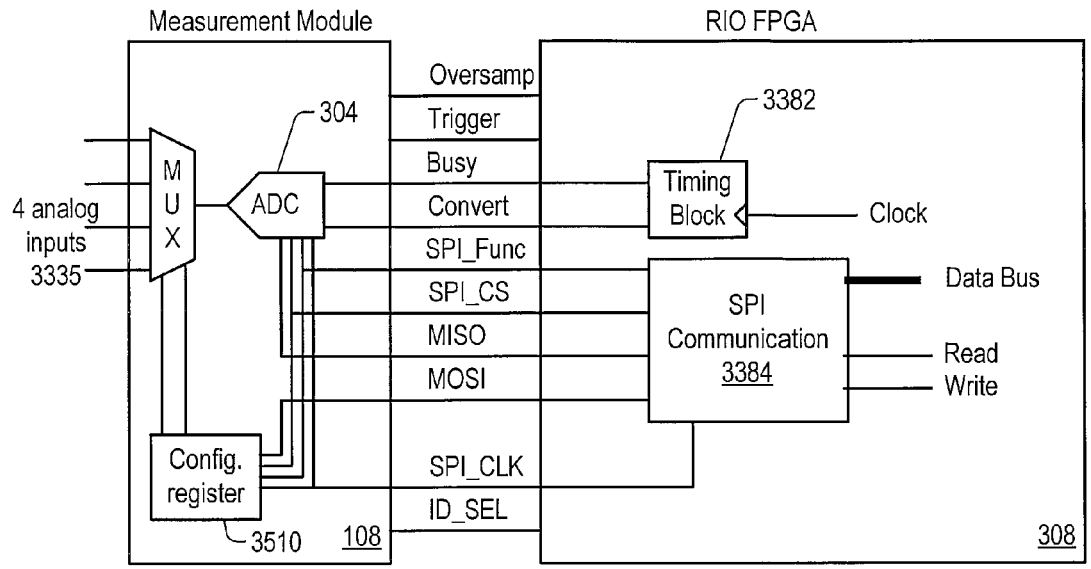

FIG. 33F is a circuit diagram for a 4-channel analog input, according to one embodiment. In this embodiment, the measurement module 108 may receive analog signals through any of 4 analog inputs 3335 which may be converted to digital signals and transmitted to the RIO FPGA. As FIG. 33F also shows, the RIO FPGA 308 is configured with a timing block 3382 to control communications with the module 108, and SPI communication logic 3384 to receive digital signals from the measurement module 108. The received digital signals may then be transmitted to external systems (or other components of the measurement system) via the data bus, as shown.

Figure 33G:
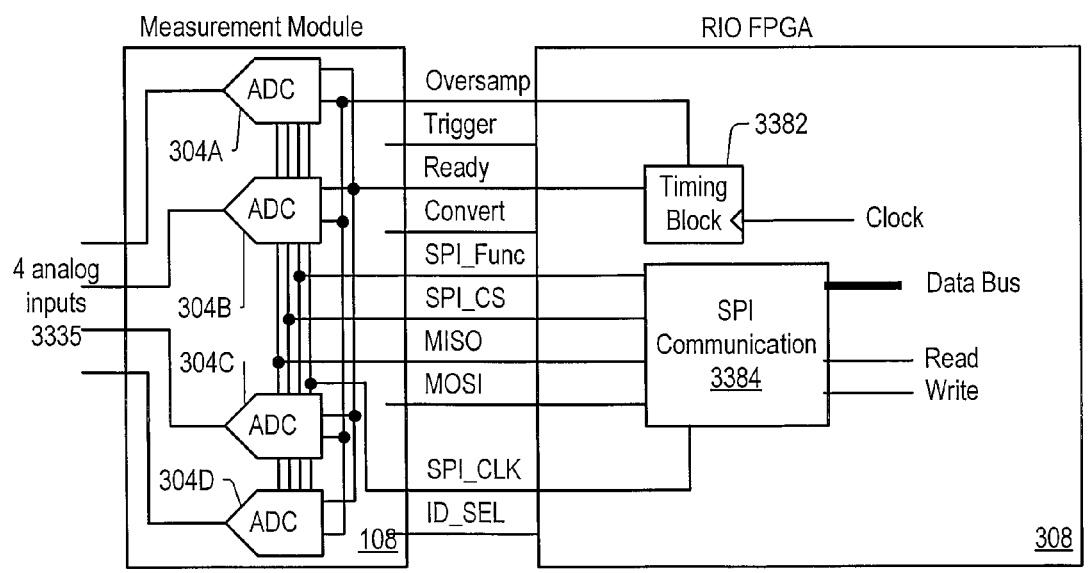

FIG. 33G is a circuit diagram for a 4-channel delta-sigma analog input, according to one embodiment. In this embodiment, the measurement module 108 may receive analog signals through any of 4 analog inputs 3335 which may be converted to digital signals and transmitted to the RIO FPGA. In contrast to the circuit of FIG. 33F, rather than MUXing the analog input signals, each analog input has it's own AD Converter 304, allowing delta-sigma operations to be performed on the plurality of input signals. As FIG. 33G also shows, the RIO FPGA 308 is configured with a timing block 3382 to control communications with the module 108, and SPI communication logic 3384 to receive digital signals from the measurement module 108. The received digital signals may then be transmitted to external systems (or other components of the measurement system) via the data bus, as shown.

FIGS. 34A-34E—Communications over SPI

In general, communications with a measurement module 108 may include sending setup information (e.g., a channel number or, in the case of an output module, data) sending a trigger, waiting for a busy line, sending commands (e.g., to read data) and reading the response. Some representative examples are presented in FIGS. 34A-34E.

FIG. 34A illustrates setup information for a simple one-channel at a time example: one trigger per channel.

FIG. 34B illustrates setup information for simultaneously sampled channels: one trigger for all channels FIG. 34C illustrates setup information for simultaneously sampled channels with data and status.

FIG. 34D illustrates setup information for very simple DAC output.

FIG. 34D illustrates setup information for fast, simple ADC input.

Serial Communication Block

As mentioned above, the Serial Communication Block 1907 is the mechanism for mapping the functions and registers of the Standard Measurement System Interface 1906 to the bit streams, control lines, and trigger lines of the Module Interface. This mechanism may be implemented as FPGA logic or as microcontroller assembly code. In general, an implementation may consist of a firm (VHDL or compiled assembly) framework that presents the Standard Measurement System Interface and which can be soft configured (for example, with configuration registers or instruction files) to support a specific module.

A format for describing this soft configuration may be provided (and defined in the next section of this document) and may be kept simple and generic enough to allow for configuration of the Serial Communication Block 1907 independent of the implementation. To allow for such flexibility some amount of structure is needed to provide a framework for this description.

Phases of a Method in the Serial Communication Block

A method may internally have three independently defined phases (or states) in its operation. First is the setup phase, followed by repetitions of the triggered and strobed phases. In one embodiment, any of these phases may null—having no action.

Setup Phase

After the method is run (i.e., invoked), it may first execute its setup phase. This phase may be executed just once in a method. It may or may not make use of channel or data information available at the time the method is started. After the setup phase completes, the Serial Communication Block may wait for either a trigger (in which case an instance of the trigger phase may be run) or for a strobe (in which case an instance of the strobe phase may be run).

Trigger Phase

After the setup phase has been run, in one embodiment, the trigger phase may be executed every time the trigger line 2104 of the Standard Measurement System Interface is asserted. In general, the ready line 2103 may be used to indicate whether the trigger phase is ready to be run. The trigger phase may be run repeatedly in a method. The trigger phase is intended to be used to control timed functions that are likely to be controlled by a timer or other trigger source connected to the trigger line 2104.

Strobed Phase

Like the trigger phase, the strobed phase may be first run after the setup phase has finished. The strobed phase may execute after each assertion of the strobe line and may be run repeatedly in a method. In general, the done line 2105 may indicate whether the strobed phase is ready to run. The intention of the strobed phase is to control non-timing sensitive functions (like reading in or reading out data) that are unlikely to be connected to timers or other trigger sources.

Each phase may consist of a series of commands that read bytes in and/or out of the SPI port; that set the levels of the control, trigger, and flow lines of the Module Interface 1908; that wait for events on the Busy line of the Module Interface 1908; that set the states of the done and ready lines of the Standard Measurement System Interface 1906; and that map the done, ready, trigger, and strobe lines of the Standard Measurement System Interface 1906 to the Convert and Busy lines of the Module Interface 1908. This series of commands may be referred to as a sequence. A module 108 may have defined several sets of these sequences. For every defined method, each phase and channel combination may be mapped to one of these sequences. Thus, every time a method is run the sequence which is mapped to the setup phase for the selected method and the selected channel may be executed. When the strobe or trigger lines are subsequently asserted the sequence that is mapped to the respective phase for the channel value set at the time of the assertion may be executed.

Components of the Serial Communication Block

Figure 35:
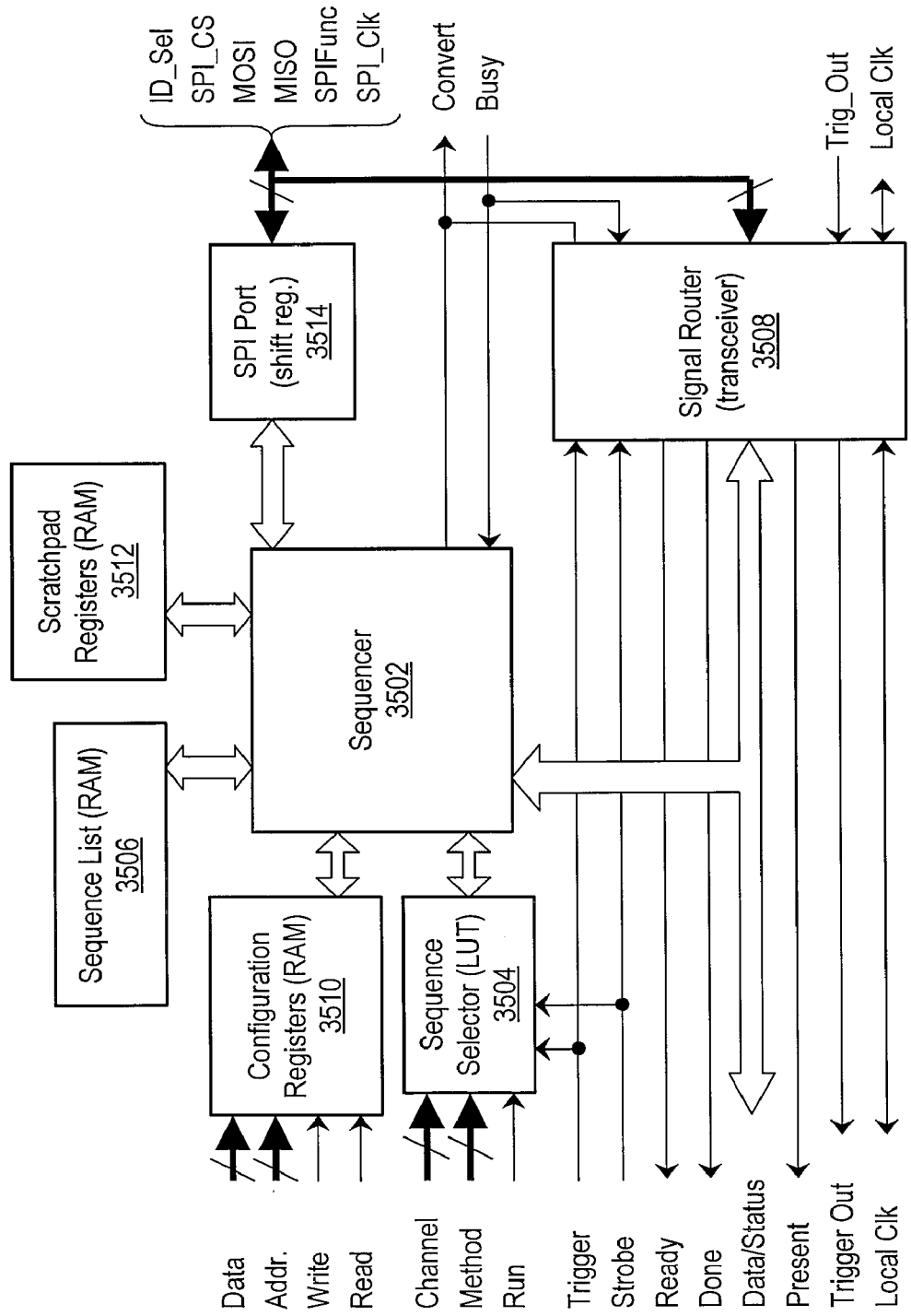
FIG. 35 is a block diagram for a serial communication block, according to one embodiment.

The firm implementation of a Serial Communication Block 1907 may consist of the following components; sequencer 3502, sequence selector 3504, sequence list 3506, signal router 3508, configuration registers 3510, scratchpad registers 3512, and pass-through mechanism 3514, described in more detail below. A block diagram of one embodiment of the Serial Communication Block 1907 is shown in FIG. 35, described below. The soft configuration of a Serial Communication Block 1907 may comprise the look-up table loaded in the sequence selector 3504, the set of commands loaded in the sequence list 3506, and the configuration of the signal router 3508 in either DIO or SPI modes.

In various embodiments, the actual implementation of the Serial Communication Block 1907 can be as VHDL or microcontroller code, and does not even need to strictly adhere to any particular format. However, the description format used to describe the operation of a module 108 may do so in terms of these components of the Serial Communication Block 1907 and in terms of the signals defined herein (or elsewhere) for the Standard Measurement System Interface 1906. Other implementations of both the Serial Communication Block 1907 and the Standard Measurement System Interface 1906 may be valid as long as suitable mappings to the described implementations are developed, thereby allowing the description format to still be properly interpreted.

Sequencer

In one embodiment, the sequencer 3502 may comprise a state machine or interpreter that runs through the sequences of commands for the phases of the methods. This component may run through the list of sequence commands for the selected method/phase/channel combination, and interpret and implement each of the commands in this list, sending out or reading in SPI data, setting or monitoring the states of the SPI control lines and the done and ready lines of the Standard Measurement System Interface 1906, and controlling the signal router 3508.

Sequence Selector

The sequence selector 3504 may hold a mapping of method/channel/phase combinations and sequence lists. Each time a phase of a method is initiated (by running the phase or by asserting the trigger or strobe lines of the Standard Measurement System Interface 1906) the sequence selector 3504 may select the appropriate list of commands from the sequence list 3506, point the sequencer 3502 to the first command in the selected list, and start the sequencer 3502.

Sequence List

The sequence list 3506 may comprise a set of registers (or other implementation specific memory file mechanism) that stores the lists of commands for each of the defined sequences. The sequence selector 3504 may index this list using its lookup table and point the sequencer 3502 to the appropriate starting position for a given phase/channel/method combination. Then the sequencer 3502 may step through the commands in this sequence list.

SPI Port

In one embodiment, the Serial Communication Block 1907 may include an SPI Port 3514 that may include a shift register that sends and receives data through the SPI lines of the Module Interface 1908. The SPI Port 3514 may control the chip selects and function select lines, and may have a programmable clock rate. The sequencer 3502 may control the SPI Port 3514.

Signal Router

The signal router 3508, under control of the sequencer 3502, may be operable to map the trigger and/or strobe lines of the Standard Measurement System Interface 1906 to the strobe line of the Module Interface 1908, and may map the Busy line of the Module Interface 1908 to the ready and/or done lines of the Standard Measurement System Interface 1906. The signal router may also map the ID-Select, Trig_Out, and Oversample Clock lines of the Module Interface 1908 to the Module Present, Trigger Out, and Oversample Clock lines of the Standard Measurement System Interface 1906. Finally, the router 3508 may map the data lines of the two interfaces (3506 and 3508) for modules that operate in DIO mode.

Configuration Registers

In one embodiment, the configuration registers 3510 may accept and store configuration data from the standard Serial Communication Block 1907 and make this data available to the sequencer 3502 for use in generating the appropriate SPI data to send to the module 108. These registers may be implemented as read/write registers from the Standard Measurement System Interface 1906 to allow for read-modify-write functions. They may preferably be read-only from the perspective of the sequencer 3502.

Scratchpad Registers

In one embodiment, the scratchpad registers 3512 may be available as internal, general purpose registers available to the sequencer for use in read-modify-write or transfer functions on the SPI port Note: Reasonable size limits for the configuration registers 3510 and the scratchpad registers 3512 need to be set. Larger configuration registers allow for data that maps directly to bytes sent out the SPI port, which can minimize the list of commands for a sequence by allowing the use of byte-, rather than bit-, oriented commands. On the other hand, using bit-oriented commands can minimize the configuration registers 3510 and make them more human-comprehensible.

Pass-Through Mechanism

In one embodiment, a mechanism to provide direct access to the Module Interface 1908 may be needed to allow for reading of the ID information of the module 108. This mechanism may also be used for low-level control of modules for special applications like testing and calibration. This mechanism may be implementation specific, and may even be implemented by loading special sequence commands in the sequence list 3506.

FIG. 35—Serial Communication Block Diagram (FPGA Implementation)

A block diagram of the Serial Communication Block 1907 is shown in FIG. 35 for an FPGA implementation. The sequence list 3502, configuration register 3510, and scratchpad registers 3512 may be simply RAM blocks, the sequence selector 3504 may be a lookup table (with logic to tell the sequencer 3502 to start), the SPI Port 3514 may be a shift register (it may have a programmable bit rate) and the signal router 3508 may be a bidirectional transceiver. The sequencer block 3502 may be the most complex of the function blocks, in that it may read and implement the commands of the sequence list 3506.

Serial Communication Block Description Format

In one embodiment, the implementation of the Serial Communication Block 1907 for a particular measurement module 108 may be realized through the soft configuration of the sequence list 3506, the sequence selector 3504, and the signal router 3508. A description format of the Serial Communication Block 1907 may only need to describe the configuration of these three components of the Serial Communication Block 1907. In one embodiment, the configuration of the sequence list 3506 may simply comprise the listing of the command codes; the configuration of the sequence selector 3504 may simply be the set of lookup values that map channel/phase/method combinations to indexes in the array of the sequence list 3506; and the configuration of the signal router 3508 may only need to be an indication of whether the Module Interface 1908 is used in SPI mode or DIO mode, and if it is in DIO mode it may need to indicate the directionality of the DIO lines.

FIG. 36—Sequence List Configuration

The sequence list component 3506 may comprise an array of commands for the sequence to carry out. Examples of supported commands are listed in FIG. 36. These commands are presented as they are used in the description format. A given implementation may modify these commands before loading them into the sequence list 3506 to better match with the specific implementation of the sequencer component 3502.

Bits vs. Bytes

SPI generally only defines byte transfers, but a variant (QSPI) does allow sub-bytes to be sent, possibly providing slightly higher performance in some cases. However, even though some SPI devices may work with QPSI non-byte length values, most SPI hardware implementations in microcontrollers may be unable to send sub-bytes. Also, the SPI Port component 3514 of the Serial Communication Block 1907 may be a little simpler to implement if it only needs to support 8-bit transfers. Thus, using byte access at the Module Interface level is probably advisable, as it may prevent possible compatibility conflicts.

Defining Communication Timing

With some care in logic and cable delays, most intended devices may work with 1 Mbit/s SPI. However, some devices may run at 10 to 20 Mbit/s so restricting the SPI communications to be defined at only 1 Mbit/s may significantly limit the potential performances of some measurement system designs. Therefore, there may be sequence commands in the description to indicate the maximum SPI rate allowed. One other potential problem is that some SPI devices actually have minimum SPI rates supported. Running the SPI clock too slowly may cause the device to reset or exhibit some other unwanted behavior. Since there is little reason to expect that the Serial Communication Block 1907 and its SPI Port component 3514 may have problems running at the SPI clock to least a couple of hundred kHz, this is probably not a problem. However, running through the sequence too slowly (i.e., taking too long between bytes) may cause self-timed ADCs (like D-S ADCs) to overwrite the data with new data before the old data can be read.

FIG. 37—SPI Rate Description Format

FIG. 32B, described above, illustrates a method of defining the maximum timing requirements for a measurement module, where a single value $\tau$ may define the timing for the module. FIG. 37 defines a set of 32 possible values for $\tau$ on an approximately logarithmic scale, according to one embodiment. This set of values may allow for rates from 20 MHz to 100 kHz, with a resolution of 15-20%. The carrier may lookup the value $\tau$, add its own timing delays, and then set the Serial Communication Block 1907 to run at the next slower rate that it is capable of generating.

Note: In one embodiment, the selected value or $\tau$ may be used not only to set the SPI clock, but to also set the convert pulse time.

FIG. 38—Creating the Description File

The format for storing the set of sequence command lists may simply comprise a listing of the commands with a header that describes which ones are used with which methods. FIG. 38 shows how this file may be constructed, according to one embodiment. The first entry is a byte indicating the number of methods supported. This is followed by a set of information for each method. The first element in this set is an ID byte that identifies the method as one of the defined methods described earlier in this document. The next element is a byte indicating the number of channels that support this method. This element is followed by a set of 4 numbers for each of those channels—the channel number and the index of the sequence list to run for each of the three phases of a method. (The first sequence list described in this file has an index of 0, the second an index of 1, and so on . . . ).

In the embodiment shown in FIG. 38, after the indexes for each phase of each channel of each method are listed, the next element in the structure is a revision identifier that indicates what revision level of the standard the sequence commands follows. This may be followed by a byte indicating the number of unique sequence lists defined by the module. For each of these sequence lists there may be a length field indicating the number of bytes of the sequence followed by those bytes of the sequence itself. After all of the sequence lists are listed, the structure may be completed with a checksum, CRC (Cyclic Redundancy Code), or other verification mechanism.

Module Description Format

Separate from defining the Serial Communication Block 1907 (which in effect describes the syntax of the communications interface), there may be a Module Description Format that defines the semantics of the Standard Measurement System Interface 1906. This may include the meanings of the methods, the interpretation of the data/status fields for each channel, and/or the interpretation of the configuration registers. These semantics may be needed for both user-level information and for the use of the system or software.

In one embodiment, the Module Description Format may provide some or all of the following information:

1. Partitioning of the configuration registers among the various channels (which bytes are associated with which channels);
2. Scaling of Data values to engineering units, and any dependencies this may have on configuration register values (such as gain settings);
3. Severity of status register values;
4. Identification of supported methods;
5. Valid values for configuration registers;
6. Meaning of configuration register values; and
7. Meaning of status register values.

The first 5 of these may be needed by the system; the last two may be used for presentation at the user-level API.

FieldPoint provides an example of the use of a standard description format for describing the semantics of a register set. One area in which the FieldPoint system is deficient is in defining relationships between channels. For example, there is no provision for indicating to the system software that one channel is meant to be the cold junction reading for the other (thermocouple) channels, or that odd channels are remote sense inputs for the even (bridge) channels, or that a one channel is the voltage and another is the current for a power input, etc.

Identification and Description EEPROM

In one embodiment, the Module Description Format and module identification information may be stored in an SPI EEPROM on each module 108. The EEPROMs may be the 25xxx family of SPI EEPROMs, as made by ST Microelectronics under the part numbers M95xxx-6, in densities from 128 bytes to 32 Kbytes, by Atmel under the part numbers AT25xxx-10I in densities from 128 bytes to 128 Kbytes, by Fairchild under the part numbers FM25CxxxE in densities from 256 bytes to 8 Kbytes, by ISSI under the IS25C family in densities from 4 Kbytes to 32 Kbytes, by Microchip under the 25C and 25LC families in densities from 512 bytes to 8 Kbytes, or by Xicor with part numbers X25xxxI in densities from 256 bytes to 32 Kbytes, although Xicor is replacing them with the X5000 family of system management parts.

EEPROM Variations

There are some variations between the different EEPROM parts that may need consideration. These variations may be in the maximum SPI speeds, the addressing modes, and the page sizes for writing.

EEPROM SPI Port Electrical Levels

Most EEPROM vendors use CMOS, rather than TTL, voltage input specs. The minimum VinH of VCC×0.7 may not be compatible with the LVTTL requirement adopted for measurement system when the EEPROMs use 5.0 Volt power. Either these EEPROMs may use 3 Volt power; or the Data In, Clock, and Chip Selects may be buffered; or a part may be chosen with LVTTL-compatible inputs (e.g., the Microchip parts).

EEPROM SPI Rates

ST makes its M95 family with versions at that run at 5 MHz and 2 MHz, Atmel's AT25 family runs at max speeds from 2.1 to 20 MHz depending on the part, Fairchild's FM25C and ISSI's IS25C families run at 2.1 MHz, Microchip's 25C family runs at 3 MHz, and Xicor's X25 family runs at either 1 or 2 MHz, with a few parts available in 5 MHz versions. Since the ID functions of the EEPROM may not be very time critical, the safest option may be to support the 1 MHz version of the Xicor line (for example, the X25040).

EEPROM Addressing Modes

All the parts in these families generally use one byte for a command followed by an address. The 128, 256, and 512 byte parts in these families use one byte for the address (in the case of the 512 byte part, the most significant address bit is placed in the command byte) while the 1024 byte and larger parts use a two byte addressing scheme, with the most significant byte first. To identify the type of EEPROM used, all parts using one byte addressing should have their first byte programmed with a dummy value of FF, and the second byte with an identifier to indicate the size of the part (see the section on the EEPROM identification byte for the format of this byte). Parts with 2-byte addressing should have this identifier in the first byte.

To determine the size and addressing mode of the EEPROM, the carrier may send the read command, followed by two address bytes of all zeros, then read the next data byte. If the EEPROM uses a single address byte, then the dummy byte may be clocked out while the second address byte is being sent and the identification byte may be clocked out next. If the EEPROM uses two address bytes, then just the identification byte may be clocked out after the second address byte. Either way, the byte read by the carrier is the identification byte, which indicates the size and therefore the addressing mode of the EEPROM.

Knowing the addressing mode is generally only important to the carrier when writing data, or when reading from somewhere in the EEPROM other than the beginning. For simply reading out the description format from the beginning, the carrier may ignore the identification byte and continue clocking out data until it reaches the end of the description fields.

Note: Any 1 kByte or larger parts using one-byte addressing, and any 512 byte or smaller parts using two-byte addressing, should be avoided to prevent compatibility issues.

EEPROM Page Sizes

The EEPROMs in these families generally support writes to a single byte at a time or writes to a whole page at a time. Writing to the EEPROMs can be relatively slow, as much as 10 ms per write. (Ramtron has an FM25C family of SPI FRAM memory parts that may be compatible with these EEPROM parts but does not have the slow write speed limitation.) It can take a long time to write very much data a byte at a time, and so page writes may often be preferred. However, the page size may vary depending on both the density and manufacturer of the part. For example, the page size of the 512 byte part is 16 bytes from ST and Xicor, but only 8 bytes from Atmel; the 1024 byte part has 32 byte pages from ST and Atmel, but only 16 from Xicor. All parts support byte mode operation, and all parts may have at least 8 byte pages, and all of these parts allow partial page writes; therefore a carrier may simply assume that all parts may have 8 byte pages. However, if it ever becomes necessary to program an entire 32 Kbyte part using 8 byte pages it may take as long as 40 seconds (and nearly 3 minutes for a 128 Kbyte part). For this reason, it may be desirable to know the actual page size for a part to speed up programming. This can be accomplished by use the first three bytes of the EEPROM identification byte to indicate the page size.

Note: there may be some EEPROMs available (the HP series from Atmel, for example) that ONLY support full-page writes. Since these parts require a carrier to know the page size they should not be used. Likewise, any part with smaller than 8 byte pages should not be used, such as some of the smaller Fairchild parts.

EEPROM Identification Byte

The identification byte may be the first byte read from the EEPROM as described in the section on EEPROM Addressing Modes. The first three bytes may indicate the page size, and the last five bytes may indicate the EEPROM size. The page size may be represented as a 0 for 8-byte pages, 1 for 16-byte pages, 2 for 32-byte pages, up to 7 for 2048-byte pages. The EEPROM size may be represented as 7 for 128 bytes, 8 for 256 bytes, 9 for 512 bytes, and so on. Thus, a 4 Kbyte part with 32 byte pages may be represented as 0x4C.

The values 0x00 and 0xFF may be reserved as invalid values to give a quick indication of an un-programmed part or an invalid read attempt.

Delta-Sigma Converters

The following section describes delta-sigma converters, as used in various embodiments of the present invention.

Delta-Sigma Converter Overview

Delta-Sigma (D-S) converters typically require a continuously running oversample clock, to which all conversions are synchronous. Although this may cause problems with multiplexing and synchronizing, D-S converters' inherently high linearity and built-in DSP functionality make them particularly useful for a number of applications. Some D-S ADCs trade off speed for low-noise and high resolution for use with DC analog inputs, often with the DSP set to filter out harmonics of 50 or 60 Hz line noise. Other D-S ADCs use their high linearity and their ability to set the DSP for linear, brick wall filtering to be ideal for high resolution, low distortion audio and dynamic measurements. It is common in audio applications for outputs to use D-S DACs, which provide high resolution and low distortion outputs with quantization noise at an easily filterable high frequency.

In the case of an analog-to-digital delta-sigma converter, the oversample clock may be some multiple of the desired update rate. This multiple varies depending on the type of converter, and different filtering options for a given converter may require different multiples. A typical D-S ADC may require a continuously running oversample clock at a multiple n of the desired update rate, and after every n of these clocks it may assert a signal to indicate that a new sample is ready. The ADC may have its data read out before the next conversion is complete.

In the case of a digital-to-analog delta-sigma converter, the oversample clock may again be some multiple of the desired data rate. As with D-S ADCs, this multiple can vary between part types, and some parts may support different multiples. A typical stereo D-S audio DAC requires both the high frequency oversample clock and a data update clock. The oversample clock may be synchronous to and at a multiple n of the data update clock, although the phase relationship between these clocks can generally be arbitrary. The DAC may receive new data after each data update clock and before the next one.

Note: Other converter types requiring special clocking do exist. For example, some SAR ADCs require a clock to go through the internal steps of a conversion. However, this clock generally does not need to have any synchronization relationship to any other system clock, and so a measurement module 108 may be able to provide the clock internally without regard for system timing issues. In common practice, however, ADCs that used with measurement system either may have an internal oscillator providing the clock or may use the SPI clock for this function.

Problems with Delta-Sigma Converters and Measurement System

Delta-sigma converters may have three unique properties that can cause problem areas in a measurement system. They may require oversample clocks to be generated and synchronized with the system; data from these converters may be solely generated or consumed synchronously to these clocks; and data may take time running through the DSP filters on the way through the converter.

Figure 39:
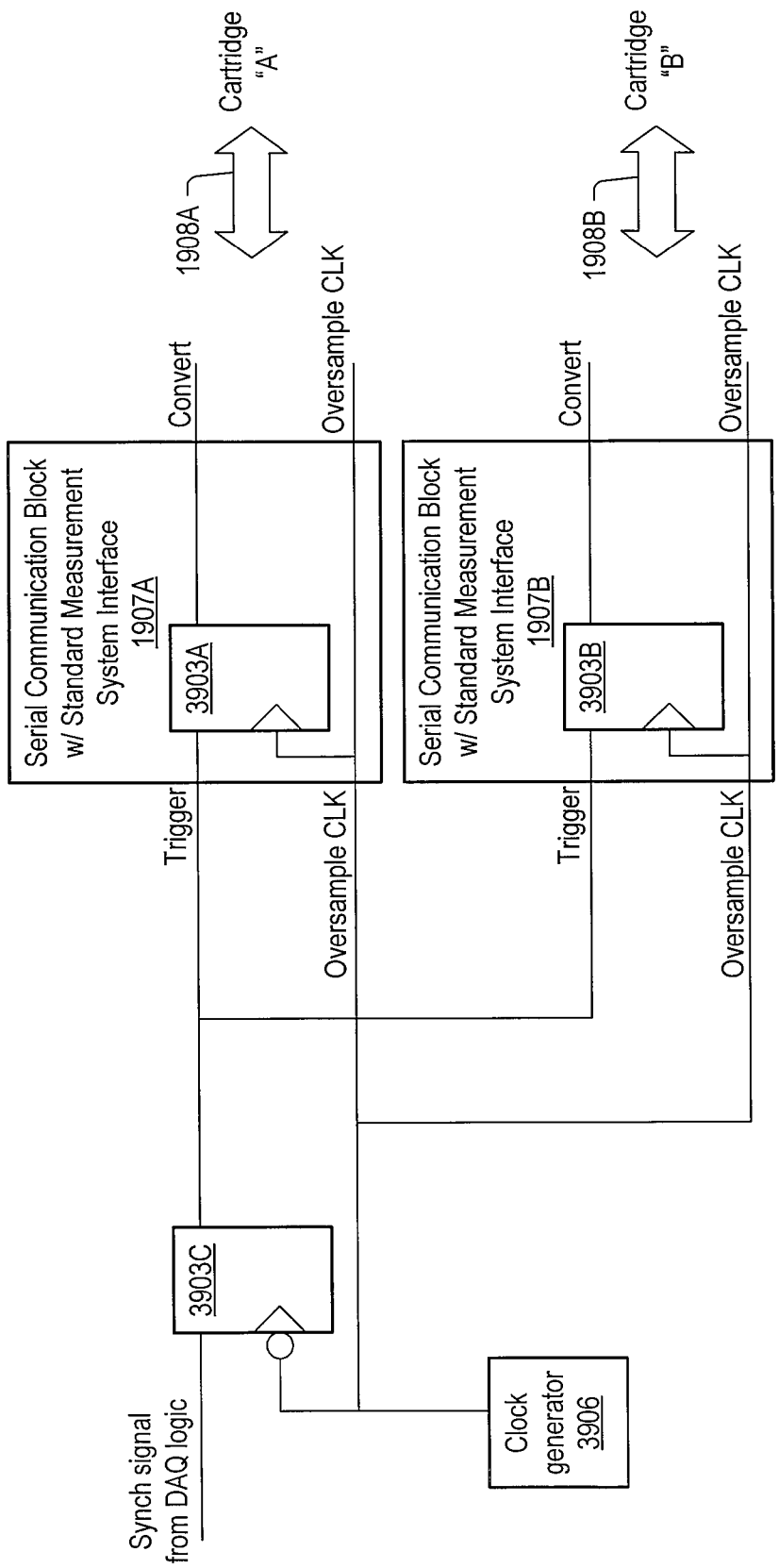
FIG. 39 illustrates one embodiment of a carrier logic configuration for synchronizing multiple delta-sigma converters.

FIG. 39—Oversample Clock Generation and Synchronization

Different D-S DACs and ADCs may require different clock frequencies from each other and for different clock rates. Typical oversample rates can be 64×, 128×, 192×, 256×, 384×, or 512×. Some converters require a fixed frequency clock, such as 32.768 kHz or 2.4576 MHz, and internally generate the proper divisions and filter settings through software settings. Other converters require variation of the oversample clock frequency to obtain different sample rates, and still others require variation of both the oversample clock rate and internal converter registers to obtain different sample rates or filter functions. The various modules and target applications may require generation of a wide variety of clocks. A typical audio DAC running at a standard 44.1 kHz frequency may need a clock of 11.2896 MHz, while a typical DC ADC may require a clock of 2.4576 MHz to internally set it's filter to reject 60 Hz harmonics, and a general purpose D-S ADC may need a clock at 7.680 MHz for an update rate of 20 kHz. Requiring all carriers to be responsible for generating appropriate frequencies for each module 108 and each application is a substantial burden, and virtually impossible for simple microcontrollers and even for many FPGAs. It may be possible for an FPGA to generate a clock that is "close enough" using a DLL or maybe a simple divider, and then implement a digital interpolation filter to resample the data at the desired rate. However, this method may consume FPGA resources, and may effectively introduce jitter that adversely affects the filter characteristics and measurements of the converter. One way to solve the problem of generating clocks specific to a particular module's target application is to put the burden on the module 108 to provide an appropriate clock source.

The oversample clock may require synchronization with other system functions, particularly with other converters. Even if two identical modules each use their internal oversample clocks at the "same" frequency, these clocks may drift and the modules may lose synchronization over time. This may require that modules be able to drive their converters from either their internal clock or from an external clock. The carriers may be able to either drive all of the modules that need to be synchronized with a single clock that the carrier generates, or the carrier may route the clock from one module 108 to the others. Using a single clock generated by the carrier has the disadvantage mentioned above of limited frequency choices, but using one module 108 as a clock master has the disadvantage of effectively advancing the clock of that module 108 in time relative to the other modules. A logic implementation that delays this clock by 300 ns would cause phase matching errors of 1° at 10 kHz. This level of phase error may or may not be significant compared to the normal module-to-module phase matching errors due to pre-filter characteristics and isolator delays. A fundamental application-level tradeoff may remain between having some amount of phase delay between modules and having available certain specific sample rates.

The implementation of the carrier logic, particularly in cases where a module 108 generates the oversample clock, may likely involve state machines that have clocks that are asynchronous to the oversample clock. This may create the potential for logic synchronization problems within the state machine. When the carrier attempts to synchronize multiple modules to a single oversample clock, there may exist the very real possibility that the state machines in the FPGA may be clocked so closely to the oversample clock that some modules may get their synchronization command before the oversample clock edge while others may get the command after that clock edge. The result of this may be that different modules may end up synchronized a whole oversample clock period apart, resulting in an apparent phase delay of one oversample clock period.

To allow for correct synchronization of multiple D-S converter, at least in the tightly timed case where the carrier is generating all the oversample clocks, the rising edge of the Trigger signal on the Standard Measurement System Interface 1906 may be defined as being valid on the falling edge of the Module Interface Oversample Clock line. This can be accomplished by having the Trigger line [of? and?] all the measurement system interfaces be latched on a falling edge of Oversample Clock, then having each measurement system interface latch it with the next rising edge of the Oversample Clock. This then means that D-S modules that would benefit from synchronization may use their Convert line as a signal to start sampling the converters with the Oversample Clock. The Signal Router function may then connect the Trigger line on the Standard Measurement System Interface 1906 to the Convert line on the Module Interface 1908 with low delays. FIG. 39 illustrates one embodiment of a mechanism the carrier's logic may use to synchronize multiple D-S converters. It should be noted that the embodiment of FIG. 39 is illustrative only, and is not intended to limit the mechanism to any particular form or architecture.

Note: By requiring the Signal Router function in the Serial Communications Block 1907 to allow routing or gating of the SPI_CS and/or SPI_FUNC, there may be more flexibility in the design of D-S modules by removing the restriction of using the Convert line to control converter start-up and synchronization.

Data Synchronization

Delta-Sigma modulators typically generate or consume data strictly according to the oversample clock. This may make it difficult to synchronize data with other converters, which sample data whenever they receive a convert or load signal. It may be possible to resynchronize data from a delta-sigma to another clock source by using a digital interpolation filter as mentioned above, but the most practical method to keeping synchronization between delta-sigmas and traditional converters is to generate the oversample clock for the delta-sigmas and the conversion clock for the other converters from the same source. This may involve the tradeoffs mentioned above regarding clock generation and choosing specific sample frequencies. Once possible consequence is that there may exist a limited number of frequencies at which data can be read/written synchronously from both delta-sigmas and conventional converters.

Synchronizing delta-sigmas to each other may be much more important. This may require not only driving them from the same clock source, but also forcing them to start their conversions at the same time. This may be necessary both for synchronizing the converters within a module 108 and for synchronizing converters in different modules. The Synchronize Self-Timed Channels method may provide a consistent mechanism for accomplishing this. However, the previously discussed problems stemming from a lack of synchronization between the oversample clock and the state machine logic can cause the different converters to be off from each other by one oversample clock period, at least in the case where one module 108 generates a clock that other modules consume. The fixed (and small) delay between modules stemming from this skew may not be significant in most cases, but this problem may be preventable using the strategy shown in FIG. 39, where the carrier generates the master oversample clock. A potentially more significant issue is that when these (almost) synchronized modules are given the command to start acquiring data, some of the modules may have just finished a sample while others are just about to, so the first sample from different modules may now be a whole sample clock period off. This may be a problem for some applications. This problem could be solved by waiting until all the modules provide a new data point before sampling any of them. The root problem of synchronizing the oversample clock with the state machine logic is more difficult to eliminate. Even if the oversample clock and state machine clocks were perfectly synchronized, the phase relationship between the oversample clock and any other signals on the module 108 (particularly the Busy signal which indicates that new data are available) could be arbitrary, especially given the potentials for propagation delays through logic and isolators. In other words, even if one knew exactly when the oversample clock was occurring, one would not necessarily know at what time relative to that clock it was safe to start conversions or to start waiting for conversions. Therefore, it may need to be left to the DAQ personality 1905 after the Serial Communication Block 1907 to handle the transfer of data, perhaps by using the suggested method of waiting for all modules to indicate that data are ready.

Filter Settling Time

Even when the oversample clocks of the delta-sigmas in a system are derived from the same clock that creates the conversion clocks of the conventional converters in a system, the most that can be said of the various conversions is that they are synchronous—they are still not necessarily simultaneous. With most conventional converters, a conversion signal indicates the time at which the analog signal matches the digital data. Delta-sigmas, however, may be constantly sampling their signals with the oversample clock and their digital data may be representative of the digitally filtered integration of that signal over time. The concept of the data being valid at a given time may only apply with the resolution of that time described being considered on the order of the data rate (or slower). This filtering aspect may be simply inherent in delta-sigmas and may be one of the factors that need to be taken into consideration when choosing a delta-sigma for an application. This fact may also mitigate the need for particularly tight timing relationships between delta-sigmas and conventional converters.

Power-Up and Hot-Swap Behavior

In one embodiment, carriers 110 may maintain the module interface in a tri-stated mode until they detect (from the ID_Select line) the attachment of a module 108. The carrier 110 may then identify the module 108 using the ID mode of the Module Interface 1908. After a successful identification, the carrier 110 may then configure the module 108 using settings that are stored in the carrier 110 or using factory default settings that are stored in the module 108. During the period between the module 108 having power applied and the carrier 110 configuring it to its power up state, the modules 108 may have the responsibility to power up (glitch free) in as "innocuous" a state as possible—usually a high impedance state or the power-off state (which preferably may be identical).

Module Detection Using ID Select

In one embodiment, the carrier 110 may use the pull-up (1.5 kW to 3.3 kW) on the ID_Select line of each module 108 to detect the presence or absence of a module 108. The carrier 110 preferably has a weak pull-down on the line. If the carrier 110 detects a low value on the line (no module), then it may tri-state all of its other signal lines to that module. When a carrier 110 detects the line changing from a low to a high (a module insertion) it may begin reading the ID EEPROM of the module 108 by first driving the SPI-_CLK line to the idle state, then asserting the ID_Select line, then enabling the SPI_Func and SPI_MOSI lines. The carrier 110 may then read the EEPROM in the normal manner.

If the EEPROM read fails (either a 0x00 or 0xFF is read in the EEPROM identification byte or an invalid checksum is encountered) then the carrier may tri-state SPI_Func and SPI_MOSI lines while still holding the ID_Select line low, then tri-state the ID_Select line. If the ID_Select line is pulled high by the module 108 then the carrier may re-attempt an EEPROM read by asserting the ID_Select line, enabling the SPI_Func and SPI_MOSI lines, and read the EEPROM from the beginning again. If instead the ID_Select line remains low then the carrier may also tri-state SPI_CLK and remain in this idle state until it detects that the ID_Select line is high again.

Powering Up a Module after Identification

After successfully reading the EEPROM, the carrier 110 may return the interface 1908 from the ID mode to the normal operating mode, either SPI mode or DIO mode. If the module 108 uses the DIO interface, then the SPI_Func and SPI_MOSI lines may first be tri-stated (while the ID_Select line is still held low), then the ID_Select line may be driven high. Then the carrier 110 may drive any output lines to the desired power-up states for that module 108. During the period where the carrier 110 tri-states the signal lines and drives ID_Select high (or tri-states ID_Select during the Module Detection procedure) it may be the responsibility of the module 108 to keep all of the outputs in the "innocuous" or power-down state. In one embodiment, the responsibility of the carrier is to never drive the 8 DIO lines as SPI mode values unless it is driving ID_Select low. The modules 108 may pull up or down these eight lines with resistors as large as 10 kOhm; therefore, the carriers 110 may use keeper circuits or weak pull-ups that can be overcome by resistances as high as 10 kOhm to either 5V or Ground.

If the module 108 uses the SPI interface rather than the DIO interface, then the carrier 110 may exit ID mode by simply driving the ID_Select line high. The carrier 110 may continue to drive SPI_Func, SPI_MOSI, and SPI_CLK; and it may drive the SPI_CS line to the idle (high) state. The module 108 may be responsible for ignoring the SPI_CS line during the ID mode when the carrier 110 is not driving SPI_CS. If the module 108 does this with a pull-up resistor, this resistor may be no larger than 10 kOhm to allow it to overcome the weak pull-ups or keeper circuits that the carrier 110 may use while it tri-states the line.

After a carrier 110 takes a module 108 that uses the SPI mode interface out of the ID mode, the carrier 110 may load the configuration registers of the Serial Communications Block 1907 with the desired power up settings, and then run the Initialize Method (if supported by the module).

Power-Up Settings

The context in which a module 108 powers up may affect the settings that the carrier should apply to the output values and configuration register values. The first priority is the Hot-Swap case: if a module 108B is detected as being inserted into a location that had previously held another module 108A with which it is hot-swap compatible (matching Hot-Swap IDs), then the new module 108B may be powered up with the settings of the previous module. If the new module 108 is not hot-swap compatible, or if there was no previous module, the next priority for assigning power up settings are user-defined values. If the carrier 110 has been programmed with specific power up settings or sequences for a module 108 of a type that matches that of the new module 108B, then that new module 108B may be powered up with those programmed settings or sequences. If the new module's type does not match with any user-defined power up settings, then the option of last resort is to power up the module 108B with the factory default settings as stored in the module's identification EEPROM.

Factory Defaults

A set of factory default power-up settings may be stored in the identification EEPROM of each measurement module. These settings may include the static default values (0 or 1) of a DIO mode digital module or the configuration register settings, default output data values, and/or an initialization method for an SPI mode module. In the absence of any other power-up setting information, the carrier 110 may use these factory default values as indicated in the previous section.

Hot-Swapping

When a carrier 110 detects the removal of a module, the carrier 110 may disable the module interface 1908 by tri-stating the interface lines. However, the carrier 110 may remember the last state (configuration register settings and output values) of the module. If the carrier 110 later detects in that location a module 108 with the same Hot-Swap identifier in its Identification EEPROM, then the carrier 110 may reconfigure this module 108 with the settings of the previous module, rather than with the factory default settings. This may allow replacement of module 108 without requiring user intervention to reconfigure the module. Depending on the intended use and design of the carrier 110, the carrier 110 may allow modification of the module's settings (output values and configuration register settings) while the module 108 is missing, so that on its replacement the power-up state of the module 108 may reflect any modifications that have occurred during its absence.

User-Definable Power-Up Settings

It may be possible to program a carrier with user-definable power-up settings that override the pre-defined factory default settings. At a minimum, these settings may be associated with a particular Hot-Swap identifier and may include configuration register settings and output values. If a carrier 110 detects that a new module's Hot-Swap identifier matches with a hot-swap identifier for which user-defined power-up settings have been stored then the carrier 110 may apply those settings to the new module. It may even be possible for a carrier 110 to allow, in addition to static output values, programming of a power-up sequence. This may include a timed sequencing digital module or a waveform output of an analog module. The existence and complexity of power up sequencing depends on the needs and capabilities of the particular carrier 110.

Power-Up Delays

Between the time that the carrier 110 receives power from the module interface 1908 and the time that the carrier 110 has completed its power-up configuration of that module 108, the module 108 may have the responsibility to maintain its outputs in as innocuous a state as possible. In addition, it may be the responsibility of these modules 108 to maintain the states of their outputs in an innocuous state whenever they are not receiving power from the module interface 1908—even if the module's output stages are receiving field power from the front connector. In addition to being innocuous, both this power-off state and the interim power-up state may be the same state if possible, such that the delay time until the carrier can properly configure the module 108 may manifest itself only as a lengthening of the powered-down state, rather than as an interim alternate state. Keeping the state innocuous means that the outputs are in what may be a relatively safe state during the powered-off or powering-up states.

In general, an innocuous state is a high impedance state in which the outputs are neither driven nor clamped to each other or to any particular voltage. (Clamping to voltages outside the specified operating ranges may be acceptable both in powered-off states as well as powered-on.) There may be some cases, particularly with analog voltage output designs, where it may add significant cost to guarantee that the outputs present a high impedance across the operating voltage range. In these cases, a second-best choice of an innocuous state may be a clamping or driving to ground.

There may be exceptions to these rules for specific modules. For example, it may be beneficial to offer versions of modules with normally closed (Form B) relays or discrete outputs, or even latching relays/discrete outputs that maintain their last states. Certain specialty modules, e.g., bus-powered communication designs, may have an innocuous state that is defined as being driven or clamped to particular levels.

Thus, various embodiments of the systems and methods disclosed herein may provide means for a measurement module to communicate interface protocol information to a carrier unit (or computer system), and for the carrier unit to be programmed to implement the communicated interface protocol. This "adaptive interface" approach allows measurement modules to include only those components necessary for providing the required functionality, i.e., the measurement module does not have to include hardware and software implementing standard interfaces for communication with external systems. Additionally, the carrier unit may support multiple different interface protocols for communication with respective measurement modules, either sequentially, or in parallel. Finally, a plurality of interface protocols may be stored on a server computer system and made available for downloading to client computer systems.

Although the system and method of the present invention has been described in connection with the preferred embodiment, it is not intended to be limited to the specific form set forth herein, but on the contrary, it is intended to cover such alternatives, modifications, and equivalents, as can be reasonably included within the spirit and scope of the invention as defined by the appended claims.

The invention claimed is:

1. A programmable hardware element (PHE), comprising:
   a first one or more portions, each configured to implement a respective interface protocol of a plurality of interface protocols for communicating with one or more cartridges; and
   a second one or more portions, coupled to the first one or more portions, and each configured to implement a cartridge controller operable to provide an interface between controlling software and a respective cartridge;
   wherein each cartridge controller is operable to:
      detect coupling of the respective cartridge to the PHE;
      query the respective cartridge for configuration information of the respective cartridge;
      determine a first respective interface protocol based on the determined configuration information; and
      establish communication with the respective cartridge via a respective portion of the first one or more portions according to the first respective interface protocol implemented by the respective portion; and
   wherein the PHE is operable to control one or more cartridges coupled to the PHE for industrial operations.

2. The PHE of claim 1, further comprising:
   one or more modular blocks usable by each cartridge controller for providing the interface between the controlling software and the respective cartridge.

3. The PHE of claim 2, wherein the one or more modular blocks comprise one or more of:
   one or more timers;
   one or more triggers;
   one or more interfaces;
   one or more ports;
   one or more controllers;
   one or more queues; or
   one or more digital input/output (DIO) support blocks.

4. The PHE of claim 1,
   wherein each cartridge controller comprises, is coupled to, and/or is controlled by, at least one configurable portion, and wherein the at least one configurable portion is configurable to implement user defined functionality.

5. The PHE of claim 4,
   wherein the at least one configurable portion is configurable in accordance with a graphical program.

6. The PHE of claim 1,
   wherein each cartridge controller is coupled to the respective cartridge via a respective serial peripheral interface (SPI) port, and wherein the respective SPI port is operable to provide serial-to-parallel and/or parallel-to-serial signal conversion for each cartridge controller and/or the respective cartridge.

7. The PHE of claim 6, wherein the respective SPI port comprises one or more of:
   one or more data queues, wherein the one or more data queues are operable to store data corresponding to operations performed by the respective cartridge, and wherein the one or more data queues are operable to buffer data to compensate for latency between reception of data from the respective cartridge and transmission of data to the respective portion of the first one or more portions and/or between reception of data from the respective portion of the first one or more portions and transmission of data to the respective cartridge; or
   hardware flow control logic, wherein the hardware flow control logic is operable to decrease processing load during operation.

8. The PHE of claim 7, wherein the respective SPI port is operable to assist in controlling the respective cartridge, and wherein to assist in controlling the respective cartridge, the respective SPI port is operable to transmit commands regarding operation of the respective cartridge to the respective cartridge via an output queue of the one or more data queues.

9. The PHE of claim 7, wherein the respective SPI port is operable to repeat transmission of data via an output queue of the one or more data queues without instruction from the controlling software.

10. The PHE of claim 6, wherein to query the respective cartridge, the respective SPI port is operable to:
    query EEPROM memory of the respective cartridge to retrieve cartridge identification information.

11. The PHE of claim 6, wherein the respective SPI port is operable to operate in a plurality of modes, wherein the plurality of modes comprise one or more of:
    an identification mode, for identifying the respective cartridge;
    a basic SPI mode, wherein during operation in the basic SPI mode, the SPI port is operable to convert data, indicate a busy state, and/or exchange timing and triggering information between the cartridge controller and the respective cartridge; or
    a digital mode, for transferring digital data between the cartridge controller and the respective cartridge.

12. The PHE of claim 6, wherein each cartridge controller comprises:
    a respective SPI rate and serializer component, operable to provide clock signal communication to the respective cartridge; and wherein the respective SPI rate and serializer component is configurable to change the rate used by the SPI port during operation.

13. The PHE of claim 12, wherein the respective SPI rate and serializer component is configurable by one or more of:
    a respective portion of the first one or more portions;
    the controlling software;
    the cartridge controller, wherein the cartridge controller comprises the respective SPI rate and serializer component; or
    the respective cartridge.

14. The PHE of claim 1, wherein each cartridge controller comprises:
    a timing module, operable to provide timing signals to the respective cartridge.

15. The PHE of claim 14,
    wherein the timing module independently generates timing signals for the cartridge controller.

16. The PHE of claim 14,
    wherein the timing module generates timing signals that are coordinated with timing signals of other components comprised in the PHE.

17. The PHE of claim 1,
    wherein each cartridge controller comprises a pin multiplexer for coupling to the respective cartridge, and wherein the pin multiplexer is operable to route clock and triggering signals to and from the cartridge controller and the respective cartridge.

18. The PHE of claim 1, wherein each cartridge controller comprises:
    a cartridge detection module, operable to identify coupling and/or decoupling of the respective cartridge during operation and initiate corresponding configuration detection and/or clean-up operations based on the coupling and/or decoupling, respectively.

19. The PHE of claim 1, wherein each cartridge controller comprises:
a processor interface, operable to provide information regarding configuration, status, interrupts, and/or direct memory access (DMA) to a processor coupled to the PHE.

20. The PHE of claim of 19,
wherein the processor is operable to program each cartridge controller via the processor interface.

21. The PHE of claim 1, wherein the one or more cartridges comprise one or more of:
integrated conditioning logic;
integrated isolation logic;
signal conditioning logic;
signal conversion logic;
communication logic;
controlling logic;
networking logic; or
power supply logic.

22. The PHE of claim 1, wherein the one or more cartridges are operable to implement one or more of:
one or more data-acquisition (DAQ) operations;
one or more control operations;
one or more analysis operations;
one or more user interface operations;
one or more measurement operations;
one or more image-acquisition operations; or
one or more automation operations.

23. The PHE of claim 1, wherein the first one or more portions are operable to control the one or more cartridges via the cartridge controllers.

24. A method for utilizing a programmable hardware element (PHE) to control one or more cartridges to perform one or more industrial operations, comprising:
detecting coupling of one or more cartridges to one or more respective cartridge controllers, wherein the one or more cartridge controllers are comprised in the PHE;
querying the one or more cartridges for respective configuration information of the one or more cartridges;
determining one or more respective interface protocols based on the respective configuration information; and
establishing communication between the one or more cartridges and a controlling portion of the PHE via the one or more respective cartridge controllers using the determined one or more respective interface protocols;
the controlling portion of the PHE performing one or more industrial operations using at least a subset of the one or more cartridges and a corresponding subset of the one or more cartridge controllers.

25. A system, comprising:
means for detecting coupling of one or more cartridges to one or more respective cartridge controllers, wherein the one or more cartridge controllers are comprised in the PHE;
means for querying the one or more cartridges for respective configuration information of the one or more cartridges;
means for determining one or more respective interface protocols based on the respective configuration information; and
means for establishing communication between the one or more cartridges and a controlling portion of the PHE via the one or more respective cartridge controllers using the determined one or more respective interface protocols;
wherein the controlling portion of the PHE is operable to perform one or more industrial operations using at least a subset of the one or more cartridges and a corresponding subset of the one or more cartridge controllers.

* * * * *